United States Patent
Noursadeghi et al.

(10) Patent No.: US 11,840,742 B2
(45) Date of Patent: Dec. 12, 2023

(54) METHOD FOR DETECTING ACTIVE TUBERCULOSIS

(71) Applicant: UCL Business LTD, London (GB)

(72) Inventors: Mahdad Noursadeghi, London (GB); Jennifer Roe, London (GB); Adrian Martineau, London (GB)

(73) Assignee: UCL BUSINESS LTD, London (GB)

( * ) Notice: Subject to any disclaimer, the term of this patent is extended or adjusted under 35 U.S.C. 154(b) by 382 days.

(21) Appl. No.: 16/079,450

(22) PCT Filed: Feb. 24, 2017

(86) PCT No.: PCT/GB2017/050483
§ 371 (c)(1),
(2) Date: Aug. 23, 2018

(87) PCT Pub. No.: WO2017/144894
PCT Pub. Date: Aug. 31, 2017

(65) Prior Publication Data
US 2019/0194725 A1   Jun. 27, 2019

(30) Foreign Application Priority Data
Feb. 26, 2016 (GB) ..................... 1603367

(51) Int. Cl.
*C12Q 1/689* (2018.01)
*C12Q 1/6883* (2018.01)
*G01N 33/68* (2006.01)

(52) U.S. Cl.
CPC .......... *C12Q 1/689* (2013.01); *C12Q 1/6883* (2013.01); *G01N 33/6893* (2013.01); *C12Q 2600/112* (2013.01); *C12Q 2600/158* (2013.01); *G01N 2800/12* (2013.01); *G01N 2800/26* (2013.01); *G01N 2800/56* (2013.01)

(58) Field of Classification Search
None
See application file for complete search history.

(56) References Cited

U.S. PATENT DOCUMENTS

| 4,275,149 A | 6/1981 | Litman et al. | |
| 2015/0315643 A1* | 11/2015 | O'Garra | C12Q 1/6886 506/2 |

FOREIGN PATENT DOCUMENTS

| WO | WO 2013/190321 A1 | 12/2013 |
| WO | WO 2014/067943 A1 | 5/2014 |
| WO | WO 2014/093872 | * 6/2014 |
| WO | WO 2014/093872 A1 | 6/2014 |
| WO | WO 2015/040377 | * 3/2015 |
| WO | WO 2015/170108 A1 | 11/2015 |
| WO | WO 2017/081618 | * 5/2017 |
| WO | WO 2017/134455 | * 8/2017 |
| WO | WO 2017/144894 A1 | 8/2017 |

OTHER PUBLICATIONS

Whitehead (Genome Biology 2005 vol. 6 Issue 2 Article R13).*
Chan (G&P magazine 2006 vol. 6 No. 3 pp. 20-26).*
Hoshikawa et al (Physical Genomics 2003 vol. 12 pp. 209-219).*
Coleman (Drug Discovery Today. 2003. 8: 233-235).*
Maertzdorf, J., "Common patterns and disease-related signatures in tuberculosis and sarcoidosis," PNAS, 109(20):7853-7858 (2012).
Roe, J., "Blood transcriptomic diagnosis of pulmonary and extrapulmonary tuberculosis," JCI Insight, 1(16):e87238 (2016).
International Search Report and Written Opinion received in PCT Application No. PCT/GB2017/050483 dated May 22, 2017.
Altschul, S.F., et al., "Basic Local Alignment Search Tool," J. Mol. Biol., 215:403-410 (1990).
Anderson, S.T., et al., "Diagnosis of Childhood Tuberculosis and Host RNA Expression in Africa," N Engl J Med, 370(18):1712-1723 (2014).
Ausubel, F.M., et al., "Short Protocols In Molecular Biology," Current Protocols in Molecular Biology, 4th Ed., Chapter 18 (Bioinformatics) (1999).
Ausubel, F.M., et al., "Short Protocols In Molecular Biology," Current Protocols in Molecular Biology, 4th Ed., Unit 7.7, pp. 7-58 to 7-60 (1999).
Berry, M.P.R., et al., "An Interferon-Inducible Neutrophil-Driven Blood Transcriptional Signature in Human Tuberculosis," Nature, 466(7309):973-977 (2010).
Blankley, S., et al., "A 380-gene meta-signature of active tuberculosis compared with healthy controls," Eur Respir J, 47(6):1873-1876 (2016).
Bloom, C.I., et al., "Transcriptional Blood Signatures Distinguish Pulmonary Tuberculosis, Pulmonary Sarcoidosis, Pneumonias and Lung Cancers," PLOS ONE, 8(8):e70630, 17 pgs. (2013).
Bloom, C.I., et al., "Detectable Changes in The Blood Transcriptome Are Present After Two Weeks of Antituberculosis Therapy," PLOS ONE, 7(10):e46191, 13 pgs. (2012).
Boehme, C.C., et al., "The Changing Landscape of Diagnostic Services for Tuberculosis," Semin Respir Crit Care Med, 34:17-31 (2013).
Breuer, K., et al., "InnateDB: systems biology of innate immunity and beyond—recent updates and continuing curation," Nucleic Acids Research, 41:D1228-D1233 (2013).
Chain, B., "Agilent expression array processing package," http://www.bioconductor.org/packages/release/bioc/html/agilp.html, 3 pages, downloaded on Oct. 20, 2020.

(Continued)

*Primary Examiner* — Amanda Haney
(74) *Attorney, Agent, or Firm* — Crowell & Moring LLP

(57) ABSTRACT

The present invention relates to a method of determining the presence or absence of active tuberculosis in a sample, in particular, comprising determining the levels of one or more biomarkers selected from basic leucine zipper transcription factor ATF-like 2 (BATF2), cluster of differentiation 177 (CD177), haptoglobin (HP), immunoglobulin J chain (IGJ) and galectin 10 (CLC), in said sample. Uses of biomarkers of the invention and kits for performing the method of the invention are also described.

7 Claims, 15 Drawing Sheets

Specification includes a Sequence Listing.

(56) References Cited

OTHER PUBLICATIONS

Chain, B., et al., "Error, reproducibility and sensitivity: a pipeline for data processing of Agilent oligonucleotide expression arrays," *BMC Bioinformatics*, 11:344, 15 pgs. (2010).
Chee, M., et al., "Accessing Genetic Information with High-Density DNA Arrays," *Science*, 274(5287):610-614 (1996).
Chua, J.C., et al., "Galectin-10, a Potential Biomarker of Eosinophilic Airway Inflammation," *PLOS ONE*, 7(8):e42549, 6 pgs. (2012).
Cliff, J.M., et al., "Distinct Phases of Blood Gene Expression Pattern Through Tuberculosis Treatment Reflect Modulation of the Humoral Immune Response," *J. Inject Dis.*, 207:18-29 (2013).
Denkinger, C.M., et al., "Xpert MTB/RIF assay for the diagnosis of extrapulmonary tuberculosis: a systematic review and meta-analysis," *Eur Respir J*, 44:435-446 (2014).
DeRisi, J., et al., "Use of a cDNA microarray to analyse gene expression patterns in human cancer," *Nature Genetics*, 14:457-460 (1996).
Devereux, Jr., et al., "A comprehensive set of sequence analysis programs for the VAX," *Nucleic Acids Research*, 12(1):387-395 (1984).
Dinnes, J., et al., "A systematic review of rapid diagnostic tests for the detection of tuberculosis infection," *Health Technology Assessment*, 11(3):1-196 (2007).
Fan, J-B., et al., "Parallel Genotyping of Human SNPs Using Generic High-density Oligonucleotide Tag Arrays," *Genome Res*, 10:853-860 (2000).
Göhring, K., et al., "Neutrophil CD177 (NB1 gp, NHA-2a) expression is increased in severe bacterial infections and polycythaemia vera," *BR J Haematol.*,126:252-254 (2004).
Hacia, J.G., et al., "Detection of heterozygous mutations in BRCA1 using high density oligonucleotide arrays and two-colour fluorescence analysis," *Nature Genetics*, 4:441-447 (1996).
Kaforou, M., et al., "Detection of Tuberculosis in HIV-Infected and -Uninfected African Adults Using Whole Blood RNA Expression Signatures: A Case-Control Study," *PLOS MED*, 10(10):e1001538, 17 pgs. (2013).
Maertzdorf, J., et al., "Concise gene signature for point-of-care classification of tuberculosis," *EMBO Molecular Med*, 8(2):86-95 (2016).
Maertzdorf, J., et al., "Enabling biomarkers for tuberculosis control," *Int J Tuberc Lung Dis*, 16(9):1140-1148 (2012).
Maertzdorf J., et al., "Common patterns and disease-related signatures in tuberculosis and sarcoidosis", *Proc Nat Acad Sci*, 19(20): 7853-7858 (2012).
Martineau, A., et al., "High-dose vitamin $D_3$ during intensive phase treatment of pulmonary tuberculosis: a double-blind randomised controlled trial," *Lancet*, 377(9761):242-250 (2011).
Matsuo, K., et al., "Variations in the expression of granulocyte antigen NB1," *Transfusion*, 40:654-662 (2000).
McHugh, L., et al., "A Molecular Host Response Assay to Discriminate Between Sepsis and Infection-Negative Systemic Inflammation in Critically Ill Patients: Discovery and Validation in Independent Cohorts," *PLOS MED*, 12:e1001916, 35 pgs. (2015).
Murphy, T.L., et al., "Specificity through cooperation: BATF-IRL interactions control immune-regulatory networks," *Nature Reviews Immunol*, 13:499-509 (2013).
Norbis, L., et al., "Challenges and perspectives in the diagnosis of extrapulmonary tuberculosis," *Expert Rev. Anti Infect. Ther.*, 12(5):633-647 (2014).
Noursadeghi, M., et al., "Genome-wide innate immune responses in HIV-1 infected macrophages are preserved despite attenuation of the NF-kB activation pathway," *J Immunol*, 182(1):319-328 (2009).
Platt, J.C., et al., "Probabilistic Outputs for Support Vector Machines and Comparisons to Regularized Likelihood Methods," *Adv Large Margin Classif*, 10, 11 pgs. (1999).
Remington's Pharmaceutical Sciences, 17th Ed., *Mack Publishing Company*, 9 pgs. of Title, Publisher and Table of Contents (1985).
Roe, J.K., "Blood transcriptomic diagnosis of pulmonary and extrapulmonary tuberculosis," *JCI Insight*, 1(16):e87238, 14 pgs. (2016).
Roy, S., et al., "Batf2/Irf1 Induces Inflammatory Responses in Classically Activated Macrophages, Lipopolysaccharides, and Mycobacterial Infection," *J Immunol*, 194:6035-6044 (2015).
Sambrook, J., et al., "Molecular Cloning: A Laboratory Manual," 2nd Ed., *Cold Spring Harbor Laboratory Press, New York*, 30 pgs. of Title, Publisher and Table of Contents (1989).
Shoemaker, D.D., et al., "Quantitative phenotypic analysis of yeast deletion mutants using a highly parallel molecular bar-coding strategy," *Nature Genetics*, 14:450-456 (1996).
Silver, N., et al., "Selection of housekeeping genes for gene expression studies in human reticulocytes using real-time PCR," *BMC Mol Biol*, 7(33):9 pgs. (2006).
Stroncek, D.F., et al., "Analysis of the expression of NB1 antigen using two monoclonal antibodies," *Transfusion*, 36:168-174 (1996).
Tatusova, T.A., et al., "BLAST 2 Sequences, a new tool for comparing protein and nucleotide seguences," *FEMS Microbiology Letters*, 174:247-250 (1999).
Tatusova, T.A., et al., Erratum to "BLAST 2 Sequences, a new tool for comparing protein and nucleotide sequences," [*FEMS Microbiol Letters*, 174 (1999)(247-250], *FEMS Microbiology Letters*, 177:187-188 (1999).
Tomlinson, G.S., et al., "HIV-1 Infection of Macrophages Dysregulates Innate Immune Responses to *Mycobacterium tuberculosis* by Inhibition of Interleukin-10," *J Infect Dis*, 4(209):1055-1065 (2014).
Towers, G.J., et al., "Interactions between HIV-1 and the Cell-Autonomous Innate Immune System," *Cell Host & Microbe*, 16:10-18 (2014).
Walter, N.D., et al., "Blood Transcriptional Biomarkers for Active Tuberculosis among Patients in the United States: a Case-Control Study with Systematic Cross-Classifier Evaluation," *J Clin Microbiol*, 54(2):274-282 (2016).
Zak, D.E., et al., "A prospective blood RNA signature for tuberculosis disease risk," *Lancet*, 387(10035):2312-2322, 21 pgs. (2016).
WHO Global Tuberculosis Report 2015, 20th Edition, 204 pgs. (2015).
A letter dated Oct. 2, 2018 received in connection with the corresponding PCT application No. PCT/GB2017/050483 enclosing the International Preliminary Report on Patentability (Chapter 1) dated Aug. 28, 2018 and dated Sep. 7, 2018.

\* cited by examiner

SEQUENCE LISTING

<160> NUMBER OF SEQ ID NOS: 14

<210> SEQ ID NO 1
<211> LENGTH: 1413
<212> TYPE: DNA
<213> ORGANISM: Homo sapiens

<400> SEQUENCE: 1

| | | | | | |
|---|---|---|---|---|---|
| ttgtgattgt | ttttagtttg | ttagctgcct | ggagtgttat | tttaagaaag | cagaagcacc | 60 |
| atcatttgca | cactccttat | agatcacaca | ccttaacccct | gacttttttt | gctccagttt | 120 |
| ttcagaagaa | gtgaagtcaa | gatgaagaac | catttgcttt | tctggggagt | cctggcggtt | 180 |
| tttattaagg | ctgttcatgt | gaaagcccaa | gaagatgaaa | ggattgttct | tgttgacaac | 240 |
| aaatgtaagt | gtgcccggat | tacttccagg | atcatccgtt | cttccgaaga | tcctaatgag | 300 |
| gacattgtgg | agagaaacat | ccgaattatt | gttcctctga | caacaggga | gaatatctct | 360 |
| gatcccacct | caccattgag | aaccagattt | gtgtaccatt | tgtctgacct | ctgtaaaaaa | 420 |
| tgtgatccta | cagaagtgga | gctggataat | cagatagtta | ctgctaccca | gagcaatatc | 480 |
| tgtgatgaag | acagtgctac | agagacctgc | tacacttatg | acagaaacaa | gtgctacaca | 540 |
| gctgtggtcc | cactcgtata | tggtggtgag | accaaaatgg | tggaaacagc | cttaacccca | 600 |
| gatgcctgct | atcctgacta | atttaagtca | ttgctgactg | catagctctt | tttcttgaga | 660 |
| ggctctccat | tttgattcag | aaagttagca | tatttattac | caatgaattt | gaaaccaggg | 720 |
| ctttttttt | tttttgggtg | atgtaaaacc | aactccctgc | caccaaaata | attaaaatag | 780 |
| tcacattgtt | atctttatta | ggtaatcact | tcttaattat | atgttcatac | tctaagtatc | 840 |
| aaaatcttcc | aattatcatg | ctcacctgaa | agaggtatgc | tctcttagga | atacagtttc | 900 |
| tagcattaaa | caaataaaca | aggggagaaa | ataaaactca | aggactgaaa | atcaggaggt | 960 |
| gtaataaaat | gttcctcgca | ttcccccccg | cttttttttt | tttttttgac | tttgccttgg | 1020 |
| agagccagag | cttccgcatt | ttctttacta | ttctttttaa | aaaaagtttc | actgtgtaga | 1080 |
| gaacatatat | gcataaacat | aggtcaatta | tatgtctcca | ttagaaaaat | aataattgga | 1140 |
| aaacatgttc | tagaactagt | tacaaaaata | atttaaggtg | aaatctctaa | tatttataaa | 1200 |
| agtagcaaaa | taaatgcata | attaaaatat | atttggacat | aacagacttg | gaagcagatg | 1260 |
| atacagactt | ctttttttca | taatcaggtt | agtgtaagaa | attgccatt | gaaacaatcc | 1320 |
| attttgtaac | tgaaccttat | gaaatatatg | tatttcatgg | tacgtattct | ctagcacagt | 1380 |
| ctgagcaatt | aaatagattc | ataagcataa | aaa | | | 1413 |

<210> SEQ ID NO 2
<211> LENGTH: 1478
<212> TYPE: DNA
<213> ORGANISM: Homo sapiens

<400> SEQUENCE: 2

| | | | | | |
|---|---|---|---|---|---|
| agcataaaaa | gaccagcaga | tgccccacag | cactgctctt | ccagaggcaa | gaccaaccaa | 60 |
| gatgagtgcc | ctgggagctg | tcattgccct | cctgctctgg | ggacagcttt | ttgcagtgga | 120 |
| ctcaggcaat | gatgtcacgg | atatcgcaga | tgacggctgc | ccgaagcccc | ccgagattgc | 180 |
| acatggctat | gtggagcact | cggttcgcta | ccagtgtaag | aactactaca | aactgcgcac | 240 |
| agaaggagat | ggagtataca | ccttaaatga | taagaagcag | tggataaata | aggctgttgg | 300 |
| agataaactt | cctgaatgtg | aagcagatga | cggctgcccg | aagcccccg | agattgcaca | 360 |
| tggctatgtg | gagcactcgg | ttcgctacca | gtgtaagaac | tactacaaac | tgcgcacaga | 420 |

-continued

```
aggagatgga gtgtacacct taaacaatga gaagcagtgg ataaataagg ctgttggaga    480
taaacttcct gaatgtgaag cagtatgtgg gaagcccaag aatccggcaa acccagtgca    540
gcggatcctg ggtggacacc tggatgccaa aggcagcttt ccctggcagg ctaagatggt    600
ttcccaccat aatctcacca caggtgccac gctgatcaat gaacaatggc tgctgaccac    660
ggctaaaaat ctcttcctga accattcaga aaatgcaaca gcgaaagaca ttgcccctac    720
tttaacactc tatgtgggga aaaagcagct tgtagagatt gagaaggttg ttctacaccc    780
taactactcc caggtagata ttgggctcat caaactcaaa cagaaggtgt ctgttaatga    840
gagagtgatg cccatctgcc taccttcaaa ggattatgca gaagtagggc gtgtgggtta    900
tgtttctggc tgggggcgaa atgccaattt taaatttact gaccatctga agtatgtcat    960
gctgcctgtg gctgaccaag accaatgcat aaggcattat gaaggcagca cagtccccga    1020
aaagaagaca ccgaagagcc ctgtaggggt gcagcccata ctgaatgaac acaccttctg    1080
tgctggcatg tctaagtacc aagaagacac ctgctatggc gatgcgggca gtgcctttgc    1140
cgttcacgac ctggaggagg acacctggta tgcgactggg atcttaagct tgataagag    1200 ctgtgctgtg gctgagtatg gtgtgtatgt gaaggtgact tccatccagg actgggttca    1260
gaagaccata gctgagaact aatgcaaggc tggccggaag cccttgcctg aaagcaagat    1320
ttcagcctgg aagagggcaa agtggacggg agtggacagg agtggatgcg ataagatgtg    1380
gtttgaagct gatgggtgcc agccctgcat tgctgagtca atcaataaag gctttctttt    1440
tgacccataa aaaaaaaaaa aaaaaaaaaa aaaaaaa                            1478
```

<210> SEQ ID NO 3
<211> LENGTH: 1301
<212> TYPE: DNA
<213> ORGANISM: Homo sapiens

<400> SEQUENCE: 3

```
agcataaaaa gaccagcaga tgccccacag cactgctctt ccagaggcaa gaccaaccaa     60
gatgagtgcc ctgggagctg tcattgccct cctgctctgg ggacagcttt ttgcagtgga    120
ctcaggcaat gatgtcacgg atatcgcaga tgacggctgc ccgaagcccc ccgagattgc    180
acatggctat gtggagcact cggttcgcta ccagtgtaag aactactaca aactgcgcac    240
agaaggagat ggagtgtaca ccttaaacaa tgagaagcag tggataaata aggctgttgg    300
agataaactt cctgaatgtg aagcagtatg tgggaagccc aagaatccgg caaacccagt    360
gcagcggatc ctgggtggac acctggatgc caaaggcagc tttccctggc aggctaagat    420
ggtttcccac cataatctca ccacaggtgc cacgctgatc aatgaacaat ggctgctgac    480
cacggctaaa aatctcttcc tgaaccattc agaaaatgca acagcgaaag acattgcccc    540
tactttaaca ctctatgtgg ggaaaaagca gcttgtagag attgagaagg ttgttctaca    600
ccctaactac tcccaggtag atattgggct catcaaactc aaacagaagg tgtctgttaa    660
tgagagagtg atgcccatct gcctaccttc aaaggattat gcagaagtag ggcgtgtggg    720
ttatgtttct ggctgggggc gaaatgccaa ttttaaattt actgaccatc tgaagtatgt    780
catgctgcct gtggctgacc aagaccaatg cataaggcat tatgaaggca gcacagtccc    840
cgaaaagaag acaccgaaga gccctgtagg ggtgcagccc atactgaatg aacacacctt    900
ctgtgctggc atgtctaagt accaagaaga cacctgctat ggcgatgcgg gcagtgcctt    960
tgccgttcac gacctggagg aggacacctg gtatgcgact gggatcttaa gctttgataa    1020
```

| | |
|---|---:|
| gagctgtgct gtggctgagt atggtgtgta tgtgaaggtg acttccatcc aggactgggt | 1080 |
| tcagaagacc atagctgaga actaatgcaa ggctggccgg aagcccttgc ctgaaagcaa | 1140 |
| gatttcagcc tggaagaggg caaagtggac gggagtggac aggagtggat gcgataagat | 1200 |
| gtggtttgaa gctgatgggt gccagccctg cattgctgag tcaatcaata aagagctttc | 1260 |
| ttttgaccca taaaaaaaaa aaaaaaaaaa aaaaaaaaa a | 1301 |

<210> SEQ ID NO 4
<211> LENGTH: 1301
<212> TYPE: DNA
<213> ORGANISM: Homo sapiens

<400> SEQUENCE: 4

| | |
|---|---:|
| agcataaaaa gaccagcaga tgccccacag cactgctctt ccagaggcaa gaccaaccaa | 60 |
| gatgagtgcc ctgggagctg tcattgccct cctgctctgg ggacagcttt ttgcagtgga | 120 |
| ctcaggcaat gatgtcacgg atatcgcaga tgacggctgc ccgaagcccc ccgagattgc | 180 |
| acatggctat gtgagcact cggttcgcta ccagtgtaag aactactaca aactgcgcac | 240 |
| agaaggagat ggagtataca ccttaaatga taagaagcag tggataaata aggctgttgg | 300 |
| agataaactt cctgaatgtg aagcagtatg tgggaagccc aagaatccgg caaacccagt | 360 |
| gcagcggatc ctgggtggac acctggatgc caaaggcagc tttccctggc aggctaagat | 420 |
| ggtttcccac cataatctca ccacaggtgc cacgctgatc aatgaacaat ggctgctgac | 480 |
| cacggctaaa aatctcttcc tgaaccattc agaaaatgca acagcgaaag acattgcccc | 540 |
| tactttaaca ctctatgtgg ggaaaaagca gcttgtagag attgagaagg ttgttctaca | 600 |
| ccctaactac tcccaggtag atattgggct catcaaactc aaacagaagg tgtctgttaa | 660 |
| tgagagagtg atgcccatct gcctaccttc aaaggattat gcagaagtag ggcgtgtggg | 720 |
| ttatgttct ggctggggc gaaatgccaa ttttaaattt actgaccatc tgaagtatgt | 780 |
| catgctgcct gtggctgacc aagaccaatg cataaggcat tatgaaggca gcacagtccc | 840 |
| cgaaaagaag acaccgaaga gccctgtagg ggtgcagccc atactgaatg aacacacctt | 900 |
| ctgtgctggc atgtctaagt accaagaaga cacctgctat ggcgatgcgg gcagtgcctt | 960 |
| tgccgttcac gacctggagg aggacacctg gtatgcgact gggatcttaa gctttgataa | 1020 |
| gagctgtgct gtggctgagt atggtgtgta tgtgaaggtg acttccatcc aggactgggt | 1080 |
| tcagaagacc atagctgaga actaatgcaa ggctggccgg aagcccttgc ctgaaagcaa | 1140 |
| gatttcagcc tggaagaggg caaagtggac gggagtggac aggagtggat gcgataagat | 1200 |
| gtggtttgaa gctgatgggt gccagccctg cattgctgag tcaatcaata aagagctttc | 1260 |
| ttttgaccca taaaaaaaaa aaaaaaaaaa aaaaaaaaa a | 1301 |

<210> SEQ ID NO 5
<211> LENGTH: 649
<212> TYPE: DNA
<213> ORGANISM: Homo sapiens

<400> SEQUENCE: 5

| | |
|---|---:|
| catttaaatt ctgcagctca gagattcaca cagaagtctg gacacaattc agaagagcca | 60 |
| cccagaagga gacaacaatg tccctgctac ccgtgccata cacagaggct gcctctttgt | 120 |
| ctactggttc tactgtgaca atcaaagggc gaccacttgc ctgtttcttg aatgaaccat | 180 |
| atctgcaggt ggatttccac actgagatga aggaggaatc agacattgtc ttccatttcc | 240 |
| aagtgtgctt tggtcgtcgt gtggtcatga acagccgtga gtatgggggcc tggaagcagc | 300 |

```
aggtggaatc caagaatatg cccttcagg atggccaaga atttgaactg agcatctcag      360
tgctgccaga taagtaccag gtaatggtca atggccaatc tcttacacc ttgaccata       420 gaatcaagcc tgaggctgtg aagatggtgc aagtgtggag agatatctcc ctgaccaaat    480
ttaatgtcag ctatttaaag agataaccag acttcatgtt gccaaggaat ccctgtctct    540
acgtgaactt gggattccaa agccagctaa cagcatgatc ttttctcact tcaatcctta    600
ctcctgctca ttaaaactta atcaaacttc acaaaaaaaa aaaaaaaaa                 649

<210> SEQ ID NO 6
<211> LENGTH: 2238
<212> TYPE: DNA
<213> ORGANISM: Homo sapiens

<400> SEQUENCE: 6
aaaggacttg tttcctgctg aaaaagcaga aagagattac cagccacaga cgggtcatga    60
gcgcggtatt actgctggcc ctcctggggt tcatcctccc actgccagga gtgcaggcgc    120
tgctctgcca gtttgggaca gttcagcatg tgtggaaggt gtccgacctg ccccggcaat    180
ggacccctaa gaacaccagc tgcgacagcg gcttggggtg ccaggacacg ttgatgctca    240
ttgagagcgg acccaagtg agcctggtgc tctccaaggg ctgcacggag gccaaggacc    300
aggagccccg cgtcactgag caccggatgg gccccggcct ctccctgatc tcctacacct    360
tcgtgtgccg ccaggaggac ttctgcaaca acctcgttaa ctccctcccg ctttgggccc    420
cacagccccc agcagaccca ggatccttga ggtgcccagt ctgcttgtct atggaaggct    480
gtctggaggg gacaacagaa gagatctgcc ccaagggac cacacactgt tatgatggcc      540
tcctcaggct caggggagga ggcatcttct ccaatctgag agtccaggga tgcatgcccc    600
agccagtttg caacctgctc aatgggacac aggaaattgg gcccgtgggt atgactgaga    660
actgcgatat gaaagatttt ctgacctgtc atcgggggac caccattatg acacacggaa    720
acttggctca agaacccact gattggacca catcgaatac cgagatgtgc gaggtggggc    780
aggtgtgtca ggagacgctg ctgctcctag atgtaggact cacatcaacc ctggtgggga    840
caaaaggctg cagcactgtt ggggctcaaa attcccagaa gaccaccatc cactcagccc    900
ctcctggggt gcttgtggcc tcctataccc acttctgctc ctcggacctg tgcaatagtg    960
ccagcagcag cagcgttctg ctgaactccc tccctcctca agctgcccct gtcccaggag    1020
accggcagtg tcctacctgt gtgcagcccc ttggaacctg ttcaagtggc tccccccgaa    1080
tgacctgccc caggggcgcc actcattgtt atgatggta cattcatctc tcaggaggtg    1140
ggctgtccac caaaatgagc attcagggct gcgtggccca accttccagc ttcttgttga    1200
accacaccag acaaatcggg atcttctctg cgcgtgagaa gcgtgatgtg cagcctcctg    1260
cctctcagca tgagggaggt ggggctgagg gcctggagtc tctcacttgg ggggtggggc    1320
tggcactggc cccagcgctg tggtgggag tggtttgccc ttcctgctaa ctctattacc      1380
cccacgattc ttcaccgctg ctgaccaccc acactcaacc tccctctgac ctcataacct    1440
aatggccttg gacaccagat tctttcccat tctgtccatg aatcatcttc cccacacaca    1500
atcattcata tctactcacc taacagcaac actggggaga gcctgagca tccggacttg      1560 ccctatggga gaggggacgc tggaggagtg gctgcatgta tctgataata cagaccctgt    1620
cctttctccc agtgctggga tttctccatg tgagggggca gcaggacacc cagggatcta    1680
gcgtggggga ggagaggagc ctaatgagaa aatgaccatc taaagcctgc ccttcattgg    1740
```

| | |
|---|---:|
| tctggttcac gtctccaaac cagcttggat ggtagcagag acttcagggt gctccagcca | 1800 |
| aacgtatttg ggcatcacca tgacctggga ggggaagatg cactgagacg tatgaggctt | 1860 |
| ccagcctagc agccagggcc ctagcacaaa caggaggctc gccccatctg agcaactgca | 1920 |
| ggagaggtta gtacagtcat gcattgctta acgacaggga cgtgtcgtta gaaatgtgtc | 1980 |
| gttaggtgat tttatgacca taggaacatt gtagcgtgca cttacaccaa cccagatggt | 2040 |
| acagcccaat acacacccag gatggacgct agagtcgact gctcctaggc tacaagcctg | 2100 |
| cagtgcatgt tatggtgtga atactgcagg caatcttaac accacggcaa gtatttgtgc | 2160 |
| atctacacac atctaaacat agaaaaggta cagcataaat acactattgt catctcagca | 2220 |
| gaaaaaaaaa aaaaaaa | 2238 |

<210> SEQ ID NO 7
<211> LENGTH: 2142
<212> TYPE: DNA
<213> ORGANISM: Homo sapiens

<400> SEQUENCE: 7

| | |
|---|---:|
| gaaactgaaa cttggccctc tgggggcgga gtggccactg gggatttaaa gagctgccac | 60 |
| ttccttaggc ctccagaggg cactgggaag tcacagctgc tgaggacca ctctgctccc | 120 |
| ccgcctaagc catgcacctc tgtggggca atgggctgct gacccagaca gaccccaagg | 180 |
| agcaacaaag gcagctgaag aagcagaaga accgggcagc cgcccagcga agccggcaga | 240 |
| agcacacaga caaggcagac gccctgcacc agcagcacga gtctctggaa aaagacaacc | 300 |
| tcgccctgcg gaaggagatc cagtccctgc aggccgagct ggcgtggtgg agccggaccc | 360 |
| tgcacgtgca tgagcgcctg tgccccatgg attgtgcctc ctgctcagct ccagggctcc | 420 |
| tgggctgctg ggaccaggct gaggggctcc tgggccctgg cccacaggga caacatggct | 480 |
| gccgggagca gctggagctg ttccagaccc cgggttcctg ttacccagct cagccgctct | 540 |
| ctccaggtcc acagcctcat gattctccca gcctcctcca gtgccccctg ccctcactgt | 600 |
| cccttggccc cgctgtggtt gctgaacctc ctgtccagct gtcccccagc cctctcctgt | 660 |
| ttgcctcgca cactggttcc agcctgcagg ggtcttcctc taagctcagt gccctccagc | 720 |
| ccagcctcac ggcccaaact gcccctccac agcccctcga gctggagcat cccaccagag | 780 |
| ggaagctggg gtcctctccc gacaacccct tcctctgccct ggggcttgca cgtctgcaga | 840 |
| gcagggagca caaacctgct ctctcagcag ccacttggca agggctggtt gtggatccca | 900 |
| gccctcaccc tctcctggcc tttcctctgc tctcctctgc tcaagtccac ttctaacctg | 960 |
| gtcttcggag ctgggttggc cccttctttg ggctcaggaa gcagccttag cacacgggcc | 1020 |
| tctcctccct cactactggg tgctgccctg cgtggctgac cagctggccc aggatttcac | 1080 |
| agtcgaaaag gaagccacca ctgatgcctc ccactgtgac aggccctgtc accaccaata | 1140 |
| tcttatttca acctcacagt tgacctgaga aatcgagatt atcactccac tttttcagac | 1200 |
| aaggaaactg aggctcaggg aagccaagtg acaagtccaa ggtcacgaag actttcttgg | 1260 |
| agcccgaaac accaccctct gctcctcctt ctcctgtcct ggcccaggca tcctaggggc | 1320 |
| tgaaatcctg gaaccgtggg ctggtgtga aaggtttgc atgctcagag cagagaaggg | 1380 |
| ctctccccac tgcttcgtga ttccagggcc agagccatgc agtcccagaa accccaacct | 1440 |
| agctggggca ggtccagagt ccaagccctg tgggtagag ccaagcaga agccctgaag | 1500 |
| tggactcttg cttcccctag tagtgttttc agtgccaaga agctgaaact gtgagctgga | 1560 |
| gttggggaga ggtctggaag aggaccatct gggatttcta cagcctgggt acccatagcc | 1620 |

| | |
|---|---:|
| acaccaaggc ttctgggaga ttctgcaggg tcagctttcc aggctgttcc caaatagctc | 1680 |
| cctgcctccc cactgcccct aaagccacag cagaagagcc attcatctca taaacaaaaa | 1740 |
| ggaagaggaa agaatgagga aggaccctgt gcaaggttat ttgcaggcag ggatgggctt | 1800 |
| gtacctgaca gcaccacc ctgtgtggcc cccaggccct catcaccctc agaccctcc | 1860 |
| taagcagttc cctcattgct ctttggacta ggctgacagc aggaagagca gggcccatga | 1920 |
| ccgggtggaa gttcagtttt ggtgtctgct tcaagagggg gttttacact ctgattccag | 1980 |
| gacaagcact ctgaggcggg tgggggagag aaaccctggc tcttcaccca ggtttcacac | 2040 |
| acatgtaaat gaaacactat gttagtatct aacacactcc tggatacaga acacaagtct | 2100 |
| tggcacatat gtgatggaaa taaagtgttt tgcaatcttt aa | 2142 |

<210> SEQ ID NO 8
<211> LENGTH: 2074
<212> TYPE: DNA
<213> ORGANISM: Homo sapiens

<400> SEQUENCE: 8

| | |
|---|---:|
| agcaagaaag aaggcgagag agaggagacc ggaggtctga gctgcagcca ctacacaggc | 60 |
| ctggaattct accacaggga atttggtggg tgcctctaaa gggctttaac ctgcaattaa | 120 |
| tgacatggtt gctgaatggc tcctgtgggc aagagaatag gtggtttggg ggacacacgg | 180 |
| gttggaggcc cgtgcatatc ccagcagcac gagtctctgg aaaaagacaa cctcgccctg | 240 |
| cggaaggaga tccagtccct gcaggccgag ctggcgtggt ggagccggac cctgcacgtg | 300 |
| catgagcgcc tgtgccccat ggattgtgcc tcctgctcag ctccagggct cctgggctgc | 360 |
| tgggaccagg ctgaggggct cctgggcct ggcccacagg gacaacatgg ctgccgggag | 420 |
| cagctggagc tgttccagac cccgggttcc tgttacccag ctcagccgct ctctccaggt | 480 |
| ccacagcctc atgattctcc cagcctcctc cagtgccccc tgccctcact gtcccttggc | 540 |
| cccgctgtgg ttgctgaacc tcctgtccag ctgtccccca gccctctcct gtttgcctcg | 600 |
| cacactggtt ccagcctgca ggggtcttcc tctaagctca gtgccctcca gcccagcctc | 660 |
| acggcccaaa ctgcccctcc acagcccctc gagctggagc atcccaccag agggaagctg | 720 |
| gggtcctctc ccgacaaccc ttcctctgcc ctggggcttg cacgtctgca gagcagggag | 780 |
| cacaaacctg ctctctcagc agccacttgg caagggctgt tgtggatcc cagccctcac | 840 |
| cctctcctgg cctttcctct gctctcctct gctcaagtcc acttctaacc tggtcttcgg | 900 |
| agctggggttg gccccttctt tgggctcagg aagcagcctt agcacacggg cctctcctcc | 960 |
| ctcactactg ggtgctgccc tgcgtggctg accagctggc ccaggatttc acagtcgaaa | 1020 |
| aggaagccac cactgatgcc tcccactgtg acaggccctg tcaccaccaa tatcttattt | 1080 |
| caacctcaca gttgacctga aaatcgaga ttatcactcc acttttcag acaaggaaac | 1140 |
| tgaggctcag ggaagccaag tgacaagtcc aaggtcacga agactttctt ggagcccgaa | 1200 |
| acaccaccct ctgctcctcc ttctcctgtc ctggcccagg catcctaggg gctgaaatcc | 1260 |
| tggaaaccgt gggctggtgt gagaaggttt gcatgctcag agcagagaag ggctctcccc | 1320 |
| actgcttcgt gattccaggg ccagagccat gcagtcccaa aaaccccaac ctagctgggg | 1380 |
| caggtccaga gtccaagccc tggtgggtag aggccaagca gaagccctga agtggactct | 1440 |
| tgcttcccct agtagtgttt tcagtgccaa gaagctgaaa ctgtgagctg agttggggga | 1500 |
| gaggtctgga agaggaccat ctgggatttc tacagcctgg gtacccatag ccacaccaag | 1560 |

| | |
|---|---|
| gcttctggga gattctgcag ggtcagcttt ccaggctgtt cccaaatagc tccctgcctc | 1620 |
| cccactgccc ctaaagccac agcagaagag ccattcatct cataaacaaa aaggaagagg | 1680 |
| aaagaatgag gaaggaccct gtgcaaggtt atttgcaggc agggatgggc ttgtacctga | 1740 |
| cagcacccac ccctgtgtgg cccccaggcc ctcatcaccc tcagacccct cctaagcagt | 1800 |
| tccctcattg ctctttggac taggctgaca gcaggaagag cagggcccat gaccgggtgg | 1860 |
| aagttcagtt ttggtgtctg cttcaagagg gggttttaca ctctgattcc aggacaagca | 1920 |
| ctctgaggcg ggtgggggag agaaaccctg gctcttcacc caggtttcac acacatgtaa | 1980 |
| atgaaacact atgttagtat ctaacacact cctggataca gaacacaagt cttggcacat | 2040 |
| atgtgatgga aataaagtgt tttgcaatct ttaa | 2074 |

<210> SEQ ID NO 9
<211> LENGTH: 1955
<212> TYPE: DNA
<213> ORGANISM: Homo sapiens

<400> SEQUENCE: 9

| | |
|---|---|
| agcaagaaag aaggcgagag agaggagacc ggaggtctga gctgcagcca ctacacaggc | 60 |
| ctggaattct accacaggga atttgcagca cgagtctctg gaaaaagaca acctcgccct | 120 |
| gcggaaggag atccagtccc tgcaggccga gctggcgtgg tggagccgga ccctgcacgt | 180 |
| gcatgagcgc ctgtgcccca tggattgtgc ctcctgctca gctccagggc tcctgggctg | 240 |
| ctgggaccag gctgaggggc tcctgggccc tggcccacag gacaacatg ctgccggga | 300 |
| gcagctggag ctgttccaga ccccgggttc ctgttaccca gctcagccgc tctctccagg | 360 |
| tccacagcct catgattctc ccagcctcct ccagtgcccc ctgccctcac tgtcccttgg | 420 |
| ccccgctgtg gttgctgaac ctcctgtcca gctgtccccc agccctctcc tgtttgcctc | 480 |
| gcacactggt tccagcctgc aggggtcttc ctctaagctc agtgccctcc agcccagcct | 540 |
| cacggcccaa actgcccctc cacagcccct cgagctggag catcccacca gagggaagct | 600 |
| ggggtcctct cccgacaacc cttcctctgc cctggggctt gcacgtctgc agagcaggga | 660 |
| gcacaaacct gctctctcag cagccacttg gcaagggctg gttgtggatc ccagccctca | 720 |
| ccctctcctg gccttctcctc tgctctcctc tgctcaagtc cacttctaac ctggtcttcg | 780 |
| gagctgggtt ggccccttct ttgggctcag gaagcagcct tagcacacgg gcctctcctc | 840 |
| cctcactact gggtgctgcc ctgcgtggct gaccagctgg cccaggattt cacagtcgaa | 900 |
| aaggaagcca ccactgatgc ctcccactgt gacaggcccc gtcaccacca atatcttatt | 960 |
| tcaacctcac agttgacctg agaaatcgag attatcactc cactttttca gacaaggaaa | 1020 |
| ctgaggctca gggaagccaa gtgacaagtc caaggtcacg aagactttct tggagcccga | 1080 |
| aacaccaccc tctgctcctc cttctcctgt cctggcccag gcatcctagg ggctgaaatc | 1140 |
| ctggaaaccg tgggctggtg tgagaaggtt tgcatgctca gagcagagaa gggctctccc | 1200 |
| cactgcttcg tgattccagg gccagagcca tgcagtccca gaaaccccaa cctagctggg | 1260 |
| gcaggtccag agtccaagcc ctggtgggta gaggccaagc agaagccctg aagtggactc | 1320 |
| ttgcttcccc tagtagtgtt ttcagtgcca agaagctgaa actgtgagct ggagttgggg | 1380 |
| agaggtctgg aagaggacca tctgggattt ctacagcctg ggtacccata gccacaccaa | 1440 |
| ggcttctggg agattctgca gggtcagctt tccaggctgt tcccaaatag ctccctgcct | 1500 |
| ccccactgcc cctaaagcca cagcagaaga gccattcatc tcataaacaa aaaggaagag | 1560 |
| gaaagaatga ggaaggaccc tgtgcaaggt tatttgcagg cagggatggg cttgtacctg | 1620 |

```
acagcaccca cccctgtgtg gcccccaggc cctcatcacc ctcagacccc tcctaagcag    1680
ttccctcatt gctctttgga ctaggctgac agcaggaaga gcagggccca tgaccgggtg    1740
gaagttcagt tttggtgtct gcttcaagag ggggttttac actctgattc caggacaagc    1800
actctgaggc gggtggggga gagaaaccct ggctcttcac ccaggtttca cacacatgta    1860
aatgaaacac tatgttagta tctaacacac tcctggatac agaacacaag tcttggcaca    1920
tatgtgatgg aaataaagtg ttttgcaatc tttaa                               1955
```

<210> SEQ ID NO 10
<211> LENGTH: 60
<212> TYPE: DNA
<213> ORGANISM: Artificial Sequence
<220> FEATURE:
<223> OTHER INFORMATION: Primer or probe sequence, BATF2

<400> SEQUENCE: 10

```
tggaagttca gttttggtgt ctgcttcaag aggggttttt acactctgat tccaggacaa    60
```

<210> SEQ ID NO 11
<211> LENGTH: 60
<212> TYPE: DNA
<213> ORGANISM: Artificial Sequence
<220> FEATURE:
<223> OTHER INFORMATION: Primer or probe sequence, CD177

<400> SEQUENCE: 11

```
cttggacacc agattctttc ccattctgtc catgaatcat cttccccaca cacaatcatt    60
```

<210> SEQ ID NO 12
<211> LENGTH: 60
<212> TYPE: DNA
<213> ORGANISM: Artificial Sequence
<220> FEATURE:
<223> OTHER INFORMATION: Primer or probe sequence, HP

<400> SEQUENCE: 12

```
gataagatgt ggtttgaagc tgatgggtgc cagccctgca ttgctgagtc aatcaataaa    60
```

<210> SEQ ID NO 13
<211> LENGTH: 60
<212> TYPE: DNA
<213> ORGANISM: Artificial Sequence
<220> FEATURE:
<223> OTHER INFORMATION: Primer or probe sequence, IGJ

<400> SEQUENCE: 13

```
ttgggtgatg taaaccaac tccctgccac caaaataatt aaaatagtca cattgttatc     60
```

<210> SEQ ID NO 14
<211> LENGTH: 60
<212> TYPE: DNA
<213> ORGANISM: Artificial Sequence
<220> FEATURE:
<223> OTHER INFORMATION: Primer or probe sequence, CLC

<400> SEQUENCE: 14

```
tctccctgac caaatttaat gtcagctatt taaagagata accagacttc atgttgccaa    60
```

METHOD FOR DETECTING ACTIVE TUBERCULOSIS

RELATED APPLICATIONS

The present application is a § 371 national phase application of International Application No. PCT/GB2017/050483, filed Feb. 24, 2017, which claims priority to Great Britain Application No. 1603367.2, filed Feb. 26, 2016, contents of which are incorporated by reference in their entirety.

REFERENCE TO APPENDIX [CD ROM/SEQUENCE LISTING]

The instant application contains a Sequence Listing TXT which has been submitted electronically in TXT format and is hereby incorporated by reference in its entirety. Said TXT copy, created on Aug. 17, 2023, is named "pctgb2017050483-seql.txt" and is 21,031 bytes in size.

FIELD OF THE INVENTION

The present invention relates to the diagnosis of tuberculosis. In particular, the invention relates to a method for determining the presence or absence of active tuberculosis in a subject, by analysing one or more biomarkers in a sample from the subject.

BACKGROUND 10.5 million cases of active tuberculosis (TB) cause >1.5 million deaths per year. The laboratory diagnosis of active tuberculosis is only achieved in approximately 60% of patients. This depends on microbiological identification of *Mycobacterium tuberculosis* (Mtb), commonly undermined by the need to obtain poorly accessible samples from the site of the disease and by their poor sensitivity in extrapulmonary TB (Boehme et al., 2013; Norbis et al., 2014; Denkinger et al., 2014; WHO Global tuberculosis report, 2015). The fastest liquid culture systems can detect bacteria in 10-19 days and require six weeks to obtain a definitively negative result, thereby delaying clinical decisions (Dinnes et al., 2007).

Development of novel TB diagnostics is focussed on rapid tests on easily obtained clinical samples. These aim to give better negative predictive value than current tests, particularly when clinical sampling of the site of disease is difficult and in high transmission settings. They also seek to provide high positive predictive value in immunocompromised patients who are at risk of diverse infectious diseases and in regions of low TB incidence where alternative infections are more likely.

Whole blood transcriptomics have emerged ahead of proteomics and metabolomics for diagnostic biomarker discovery in TB as a result of well-established sample processing pathways (Maertzdorf et al., 2012a). This has led to the development of rapid "sample-in, answer-out", multiplex PCR platforms (McHugh et al., 2015). Several groups have described differential gene expression signatures in patients with active pulmonary TB compared to healthy uninfected individuals and those with latent TB infection (LTBI) (Berry et al., 2010; Bloom et al., 2012; Cliff et al., 2013; Maertzdorf et al., 2012b; Bloom et al., 2013; Kafourou et al., 2013; Walter et al., 2015; Maertzdorf et al., 2015).

However, transcriptional signatures associated with active TB in different studies show modest overlap, likely due to variation in technical and analytical methodologies used by different studies, or to differences in the patient cohorts in each study. There has been comparatively little assessment of blood transcriptomes in extra-pulmonary TB and limited evaluation of the specificity of TB-associated blood transcriptional signatures in comparison with other infectious or inflammatory diseases.

Novel rapid diagnostics for active tuberculosis (TB) are required to overcome the time delays and inadequate sensitivity of current microbiological tests that are critically dependent on sampling the site of disease. Multiparametric blood transcriptomic signatures associated with TB have been described, but the number of genes included remains a barrier to their development as a diagnostic tool.

The most recent studies have sought to reduce the number of genes in a diagnostic signature, achieving as few as 4-51 genes to discriminate active TB from healthy individuals with or without LTBI, or 44-119 genes to discriminate active TB from other diseases in adults (Kafourou et al., 2013; Walter et al., 2015; Maertzdorf et al., 2015). However, these numbers still represent a major barrier to translation.

A recent study identified a four gene blood transcriptional signature (GBP1, ID3, P2RY14 and IFITM3) associated with active TB (Maertzdorf et al., 2015). Only GBP1 and P2RY14 were included amongst the genes that showed statistically significant and more than two-fold differences between active TB and post recovery cases in the AdjuVIT study cohort.

The present invention seeks to provide an alternative blood transcriptional signature for diagnosing active tuberculosis using the minimum number of biomarkers possible (in some aspects using only a single gene), and preferably which is capable of diagnosing active tuberculosis with a greater degree of confidence than prior art blood transcriptional signatures. The present invention further seeks to provide a blood transcriptional signature with improved specificity over those known in the art, for example, in terms of the ability to distinguish between active tuberculosis and other febrile diseases.

SUMMARY OF THE INVENTION

The present inventors sought to elucidate the genes that—individually or in combination—discriminate patients with active tuberculosis (TB) from all healthy individuals in diverse study cohorts including asymptomatic individuals with no prior TB exposure, those with latent TB infection (LTBI) and those who have recovered from TB. The present inventors then proceeded to test the specificity of peripheral blood gene expression signatures associated with TB by comparison with a diverse repertoire of other infectious diseases presenting to hospital, and extended their assessment of these diagnostic transcriptional biomarkers to HIV-infected patients and those with extrapulmonary TB.

Accordingly, the present invention identifies a novel and robust five-gene biomarker signature for determining the presence or absence of active tuberculosis.

Thus, in one aspect, the present invention provides a method for determining the presence or absence of active tuberculosis in a sample, the method comprising the step of: determining a level of one or more biomarkers selected from:

(a) basic leucine zipper transcription factor ATF-like 2 (BATF2)
(b) cluster of differentiation 177 (CD177);
(c) haptoglobin (HP);

(d) immunoglobulin J chain (IGJ); and
(e) galectin 10 (CLC);
in said sample.

In another aspect, the present invention provides the use of one or more of:
(a) basic leucine zipper transcription factor ATF-like 2 (BATF2)
(b) cluster of differentiation 177 (CD177);
(c) haptoglobin (HP);
(d) immunoglobulin J chain (IGJ); and
(e) galectin 10 (CLC);
as a biomarker for determining the presence or absence of active tuberculosis in a sample.

Preferably, the methods and uses of the invention only require analysis of BATF2, CD177, HP, IGJ and/or CLC as biomarkers (i.e. preferably the methods and uses of the invention do not comprise determining levels of any protein or polynucleotide biomarkers other than BATF2, CD177, HP, IGJ and/or CLC). Although, for the avoidance of doubt, the levels of the biomarkers may be standardised by comparison to one or more housekeeping genes, proteins or markers, as described herein.

In particular, the present inventors have shown that a single host blood transcript, BATF2, is sufficient as a sensitive biomarker for active pulmonary and extrapulmonary TB across multiple study cohorts including diverse ethnicities and HIV infected patients.

In particular, the present inventors have identified and validated elevated blood BATF2 transcript levels as a single sensitive biomarker which discriminates active TB from healthy individuals, with receiver operating characteristic (ROC) area under the curve (AUC) scores of 0.93-0.99 in multiple cohorts of HIV-1 negative individuals, and 0.85 in HIV-1 infected individuals.

Furthermore, the present inventors have identified a novel four-gene blood transcriptional signature (which is a subset of the five-gene signature mentioned above), providing specificity to discriminate active TB from a diverse spectrum of other infectious diseases presenting to hospital with fever. The novel four gene blood signature comprising CD177, haptoglobin (HP), immunoglobin J chain (IGJ) and galectin 10 (CLC), give an ROC AUC of 0.94-1.

The above five-gene signature is therefore proposed as the best candidate for development of peripheral blood diagnostic biomarkers for active tuberculosis. Elevated blood BATF2 transcript levels provide a sensitive biomarker that discriminates active TB from healthy individuals, and a novel four gene transcriptional signature differentiates active TB and other infectious diseases in individuals presenting with fever.

In another aspect, the present invention provides a kit for determining the presence or absence of active tuberculosis in a sample, wherein the kit comprises one or more primer pairs or probes capable of determining a level of one or more biomarkers selected from the group consisting of:
(a) basic leucine zipper transcription factor ATF-like 2 (BATF2)
(b) cluster of differentiation 177 (CD177);
(c) haptoglobin (HP);
(d) immunoglobulin J chain (IGJ); and
(e) galectin 10 (CLC);
in said sample; wherein the kit optionally comprises a set of instructions.

In yet another aspect, the present invention provides a composition comprising a therapeutically effective amount of an anti-tuberculosis agent for use in the treatment of active tuberculosis in a subject identified as requiring treatment of active tuberculosis by the method of the present invention.

In still another aspect, the present invention provides a method of treating active tuberculosis in a subject identified as requiring treatment of active tuberculosis by the method of determining the presence or absence of active tuberculosis as described herein, comprising administering a therapeutically effective amount of an anti-tuberculosis agent to the subject.

DETAILED DESCRIPTION

Tuberculosis (Tb)

Tuberculosis (TB) is an infection caused by the bacterium *Mycobacterium tuberculosis* (Mtb), which is spread through inhaling tiny droplets from the coughs or sneezes of an infected subject.

TB mainly affects the lungs. However, it can affect any part of the body, including the glands, bones and nervous system.

Typical symptoms of TB include: a persistent cough that typically lasts more than three weeks and usually brings up phlegm, which may be bloody; weight loss; night sweats; high temperature (fever); tiredness and fatigue; loss of appetite; swellings.

By "active tuberculosis" it is meant that the subject infected with Mtb shows signs or symptoms of the disease.

A subject exposed to Mtb may not necessarily develop the disease. Most subjects are able to fight the infection using various components of their immune system. In fact, healthy subjects who are infected with TB only have a 10% chance of converting to active disease over their lifetime. Some are able to control the infection, but are unable to completely remove it from their bodies. In these cases, the infection remains, lying in an inactive or "latent" state.

Thus, by "latent tuberculosis infection (LTBI)" it is meant that a subject infected with Mtb does not show any signs or symptoms of the disease.

LTBI may develop into active disease at some point, often when the subject's immune system becomes weakened.

In another embodiment of the present invention, the tuberculosis is pulmonary tuberculosis or extrapulmonary tuberculosis.

"Pulmonary tuberculosis" is tuberculosis affecting the lungs. For example, pulmonary tuberculosis may cause signs or symptoms in the lungs.

"Extrapulmonary tuberculosis" is tuberculosis that occurs at an anatomical site which is not the lungs. For example, subjects suffering from extrapulmonary tuberculosis may show signs or symptoms in the brain or pericardium.

By "determining the presence or absence of active tuberculosis" it is meant the act of diagnosis of active tuberculosis in a subject or a sample obtained from a subject (i.e. positive prediction), or the act of ruling out a diagnosis of active tuberculosis in a subject or a sample obtained from a subject (i.e. negative prediction).

The level of one or more biomarkers of the invention may be indicative of the presence or absence of active tuberculosis. For example, the levels may be merely suggestive, or may definitively denote the presence or absence of active tuberculosis in a subject.

Thus, in one embodiment, the level of one or more biomarkers of the invention may be suggestive of the presence or absence of active tuberculosis. In another embodiment, the level of one or more biomarkers of the invention may denote the presence or absence of active tuberculosis.

A "febrile disease" is one characterised by a fever or a high body temperature. An "infectious disease" is one characterised by an infection, for example a microbial infection.

By "a non-tuberculosis febrile disease" or "non-tuberculosis infectious disease" it is meant a febrile or infectious disease other than tuberculosis.

In one embodiment, the subject suffering from a non-tuberculosis febrile or infectious disease presents himself or herself to hospital.

In another embodiment, the method or use of the present invention is for determining whether a subject is suffering from active tuberculosis or a non-tuberculosis infectious disease. In particular, the non-tuberculosis infectious disease may be non-tuberculosis pneumonia or non-tuberculosis febrile disease.

As used herein the term "microbiological technique" refers to a technique for detecting the presence or absence of, and/or measuring the levels of, a microorganism in a sample. Microorganisms include bacteria, protozoa, viruses, fungi and algae.

Biomarker

Methods and uses according to the present invention comprise determining the level of one or more biomarkers.

In one embodiment, the method or use of the present invention comprises determining the levels of one or more biomarkers selected from the group consisting of: BATF2, CD177, HP, IGJ and CLC.

In another embodiment, the method or use of the present invention comprises determining the levels of the group of biomarkers consisting of: BATF2, CD177, HP, IGJ and CLC.

Basic leucine zipper transcription factor ATF-like 2 (BATF2) belongs to the activator protein (AP) 1 transcription factor family, with IFN inducible expression in mononuclear phagocytic cells, also upregulated by innate immune stimulation with lipopolysaccharide or Mtb. BATF2 interacts with IFN regulatory factor (IRF) 1 to mediate downstream pro-inflammatory responses, some of which are also recognised as components of the host response to Mtb (Murphy et al., 2013; Roy et al., 2015). Given that systemic IFN activity is widely recognised in active TB (Berry et al., 2010), increased BATF2 expression is most likely due to IFN responses rather than direct Mtb stimulation of circulating blood cells.

Immunoglobulin J chain (IGJ) otherwise known as Joining chain of multimeric IgA and IgM (J-Chain) is a small polypeptide expressed by mucosal and glandular plasma cells, which regulates polymer formation of IgA and IgM. IGJ incorporation into polymeric IgA (pIgA, mainly dimers) and pentameric IgM endows these antibodies with a high valency of antigen-binding sites (making them suitable for agglutinating bacteria and viruses) and little or no complement-activating potential (which allows them to operate in a noninflammatory fashion). Only IGJ-containing polymers show high affinity for the polymeric Ig receptor (pIgR), also known as transmembrane secretory component (SC).

Haptoglobin (HP) is an acute phase haemoglobin scavenging plasma protein. The haptoglobin gene encodes a preproprotein, which is processed to yield both alpha and beta chains, which subsequently combine as a tetramer to produce haptoglobin. Haptoglobin functions to bind free plasma haemoglobin, which allows degradative enzymes to gain access to the haemoglobin, while at the same time preventing loss of iron through the kidneys and protecting the kidneys from damage by haemoglobin. This gene has been linked to diabetic nephropathy, the incidence of coronary artery disease in type 1 diabetes, Crohn's disease, inflammatory disease behaviour, primary sclerosing cholangitis, susceptibility to idiopathic Parkinson's disease, and a reduced incidence of *Plasmodium falciparum* malaria. The protein encoded also exhibits antimicrobial activity against bacteria.

Galectin 10 or Charcot-Leyden crystal galectin (CLC) is a glycan binding protein. The protein encoded by the CLC gene is a lysophospholipase expressed in eosinophils and basophils. It hydrolyzes lysophosphatidylcholine to glycerophosphocholine and a free fatty acid. This protein may possess carbohydrate or IgE-binding activities. It is both structurally and functionally related to the galectin family of beta-galactoside binding proteins. It may be associated with inflammation and some myeloid leukemias. CLC has previously been evaluated as a biomarker for eosinophilic lung inflammation (Chua et al., 2012).

Cluster of differentiation 177 (CD177) is a glycosyl-phosphatidylinositol (GPI)-linked cell surface glycoprotein that plays a role in neutrophil activation and is expressed by subpopulations of neutrophils (Göhring et al., 2004; Stroncek et al., 1996; Matsuo et al., 2000). CD177 can bind platelet endothelial cell adhesion molecule-1 (PECAM-1) and function in neutrophil transmigration. Mutations in the CD177 gene are associated with myeloproliferative diseases. Over-expression of CD177 has been found in patients with polycythemia *rubra* vera. Autoantibodies against the protein may result in pulmonary transfusion reactions, and it may be involved in Wegener's granulomatosis.

Amino acid and nucleotide sequences of human BATF2, CD177, HP, IGJ and CLC are available from publicly accessible databases, e.g. under the accession numbers as shown in the table below:

|  | IGJ | HP | CLC | CD177 | BATF2 |
|---|---|---|---|---|---|
| Entrez | 3512 | 3240 | 1178 | 57126 | 116071 |
| Ensembl | ENSG00000132465 | ENSG00000257017 | ENSG00000105205 | ENSG00000204936 | ENSG00000168062 |
| UniProt | P10591 | P00738 | Q05315 | Q8N6Q3 | Q8N1L9 |
| RefSeq (mRNA) | NM_144646 | NM_005143 NM_001126102 NM_001318138 | NM_001828 | NM_020406 | NM_138456 NM_001300807 NM_001300808 |
| RefSeq (protein) | EAX05626 | AAA88080 | NP_001819 | BAE93254 | NP_612465 NP_001287736 NP_001287737 |

Amino acid and nucleotide sequences corresponding to further variants and homologs of the above genes, as well as genes found in other species, may be found in similar publicly accessible databases or by identifying sequences showing homology to the above human sequences.

Messenger RNA (mRNA) sequences of biomarkers of the invention are shown herein as SEQ ID NOs: 1-9. SEQ ID NO: 1 is an mRNA sequence of human IGJ; SEQ ID NOs: 2-4 are three transcript variants of an mRNA sequence of human HP; SEQ ID NO: 5 is an mRNA sequence of human CLC; SEQ ID NO: 6 is an mRNA sequence of human CLC; SEQ ID NOs: 7-9 are three transcript variants of an mRNA sequence of human BATF2.

Biomarkers of the invention may comprise or consist of one or more of SEQ ID NOs: 1-9, or a derivative, fragment or variant thereof, or a sequence having at least 50%, at least 60%, at least 70%, at least 80%, at least 90%, at least 95% or at least 99% identity thereto.

Primers or probes of the invention may comprise or consist of one or more of SEQ ID NOs: 1-9, a derivative, fragment or variant thereof, a sequence having at least 50%, at least 60%, at least 70%, at least 80%, at least 90%, at least 95% or at least 99% identity thereto; or the reverse complement of SEQ ID NOs: 1-9, a derivative, fragment or variant thereof or a sequence having identity thereto.

In certain embodiments, thymidine base (T) of any of SEQ ID NOs: 1-9 may be replaced by uracil base (U).

Example primer or probe sequences for each of the biomarkers of the invention include:

```
BATF2:
                                    (SEQ ID NO: 10)
TGGAAGTTCAGTTTTGGTGTCTGCTTCAAGAGGGGGTTTTACACTCTGAT

TCCAGGACAA

CD177:
                                    (SEQ ID NO: 11)
CTTGGACACCAGATTCTTTCCCATTCTGTCCATGAATCATCTTCCCCACA

CACAATCATT

HP:
                                    (SEQ ID NO: 12)
GATAAGATGTGGTTTGAAGCTGATGGGTGCCAGCCCTGCATTGCTGAGT

CAATCAATAAA

IGJ:
                                    (SEQ ID NO: 13)
TTGGGTGATGTAAAACCAACTCCCTGCCACCAAAATAATTAAAATAGTC

ACATTGTTATC

CLC:
                                    (SEQ ID NO: 14)
TCTCCCTGACCAAATTTAATGTCAGCTATTTAAAGAGATAACCAGACTT

CATGTTGCCAA
```

Thus, the present invention provides the use of one or more of:
(a) basic leucine zipper transcription factor ATF-like 2 (BATF2)
(b) cluster of differentiation 177 (CD177);
(c) haptoglobin (HP);
(d) immunoglobulin J chain (IGJ); and
(e) galectin 10 (CLC);
as a biomarker for determining the presence or absence of active tuberculosis in a subject, or sample therefrom.

The present invention also provides the use of:
(a) basic leucine zipper transcription factor ATF-like 2 (BATF2)
(b) cluster of differentiation 177 (CD177);
(c) haptoglobin (HP);
(d) immunoglobulin J chain (IGJ); and
(e) galectin 10 (CLC);
as biomarkers for determining the presence or absence of active tuberculosis in a subject, or sample therefrom.

The present invention also provides the use of:
(a) cluster of differentiation 177 (CD177);
(b) haptoglobin (HP);
(c) immunoglobulin J chain (IGJ); and
(d) galectin 10 (CLC);
as biomarkers for determining the presence or absence of active tuberculosis in a subject, or sample therefrom.

Preferably, the sample is obtained from a subject.

The present invention also provides the use of basic leucine zipper transcription factor ATF-like 2 (BATF2) as a biomarker for determining the presence or absence of active tuberculosis in a subject or sample therefrom.

Accordingly, the method or use of the present invention may comprise determining the level of BATF2.

In a particular embodiment, a level of BATF2 is determined and none of IGJ, CLC, HP and CD177 is determined.

In a particular embodiment, a level of BATF2 is determined, to the exclusion of all other biomarkers. In other words, the method or use of the present invention consists of—or consists essentially of—determining the level of BATF2 in a sample obtained from a subject.

In another particular embodiment, levels of all of IGJ, CLC, HP and CD177 are determined, but BATF2 is not determined.

In another particular embodiment, levels of all of BATF2, CD177, HP, IGJ and CLC are determined, to the exclusion of all other biomarkers.

In accordance with the above, a particularly preferred combination of biomarkers of the invention is: BATF2 and one of IGJ, CLC, HP and CD177.

In accordance with the above, a particularly preferred combination of biomarkers of the invention is: BATF2 and CD177.

In accordance with the above, a particularly preferred combination of biomarkers of the invention is: BATF2 and any two of IGJ, CLC, HP and CD177.

In accordance with the above, a particularly preferred combination of biomarkers of the invention is: BATF2 and any three of IGJ, CLC, HP and CD177.

In one embodiment, the level of BATF2 is determined and an increased level of BATF2 in a sample obtained from the subject compared to a reference value is indicative of the presence of active tuberculosis.

In one embodiment, the level of BATF2 is determined and an increased level of BATF2 in a sample obtained from the subject compared to a reference value is suggestive of the presence of active tuberculosis.

In one embodiment, the level of BATF2 is determined and an increased level of BATF2 in a sample obtained from the subject compared to a reference value denotes the presence of active tuberculosis.

In one embodiment, the level of BATF2 is determined and an unchanged level of BATF2 in a sample obtained from the subject compared to a reference value is indicative of the absence of active tuberculosis.

In another embodiment, the present invention comprises determining the levels of the group consisting of: IGJ, HP, CLC and CD177.

In one embodiment, a level of IGJ is determined, and an increased level of IGJ in a sample obtained from the subject compared to a reference value is indicative of the presence of active tuberculosis.

In one embodiment, a level of CLC is determined, and an increased level of CLC in a sample obtained from the subject compared to a reference value is indicative of the presence of active tuberculosis.

In one embodiment, a level of HP is determined, and a decreased level of HP in a sample from the subject compared to a reference value is indicative of the presence of active tuberculosis.

In one embodiment, a level of HP is determined, and increased level of HP in a sample from the subject compared to a reference value is indicative of the presence of a non-tuberculosis disease.

In one embodiment, a level of CD177 is determined, and a decreased level of CD177 in a sample obtained from the subject compared to a reference value is indicative of the presence of active tuberculosis.

In one embodiment, a level of CD177 is determined, and an increased level of CD177 in a sample obtained from the subject compared to a reference value is indicative of the presence of a non-tuberculosis disease.

In one embodiment, a level of BATF2 and CD177 are determined, and an increased level of BATF2 in a sample obtained from the subject compared to a reference value coupled with a decreased level of CD177 in a sample obtained from the subject compared to a reference value is indicative of the presence of active tuberculosis.

In one embodiment, a level of BATF2 and HP are determined, and an increased level of BATF2 in the sample from the subject compared to a reference value coupled with a decreased level of HP in the sample from the subject compared to a reference value is indicative of the presence of active tuberculosis.

In one embodiment, a level of BATF2 and IGJ are determined, and an increased level of BATF2 in a sample obtained from the subject compared to a reference value coupled with an increased level of IGJ in a sample obtained from the subject compared to a reference value is indicative of the presence of active tuberculosis.

In one embodiment, a level of BATF2 and CLC are determined, and an increased level of BATF2 in a sample obtained from the subject compared to a reference value coupled with an increased level of CLC in a sample obtained from the subject compared to a reference value is indicative of the presence of active tuberculosis.

The method or use of the present invention therefore encompasses determining the level of any one of the following combinations of biomarkers:

IGJ and HP;
IGJ and CLC;
IGJ and CD177;
HP and CLC;
HP and CD177;
CLC and CD177;
BATF2, IGJ and HP;
BATF2, IGJ and CLC;
BATF2, IGJ and CD177;
BATF2, HP and CLC;
BATF2, HP and CD177;
BATF2, CLC and CD177;
IGJ, HP and CLC;
IGJ, HP and CD177;
HP, CLC and CD177;
BATF2, IGJ, HP and CLC;
BATF2, HP, CLC and CD177;
BATF2, IGJ, CLC and CD177;
BATF2, IGJ, HP and CD177;
IGJ, HP, CLC and CD177;
BATF2, IGJ, HP, CLC and CD177;

preferably wherein when a level of IGJ and/or CLC is determined, an increased level of IGJ and/or CLC compared to a reference value is indicative of the presence of active tuberculosis; preferably wherein when a level of HP and/or CD177 is determined, a decreased level of HP and/or CD177 compared to a reference value is indicative of the presence of active tuberculosis; preferably wherein when a level of BATF2 is determined, an increased level of BATF2 compared to a reference value is indicative of the presence of active tuberculosis; or an unchanged or decreased level of BATF2 compared to a reference value is indicative of the absence of active tuberculosis. The determination of the levels of each of the above biomarker sets may be to the exclusion of all other biomarkers.

The biomarker of the invention may be a protein or nucleic acid. The nucleic acid may be a ribonucleic acid (RNA) or deoxyribonucleic acid (DNA). The RNA may be a pre-mRNA or mRNA.

In a preferred embodiment, the biomarker is a mature mRNA.

Thus, in one embodiment, the method or use of the invention comprises determining the mRNA or protein level of one or more of IGJ, HP, CLC, CD177 and BATF2.

Diagnosis of tuberculosis is traditionally performed by determining the presence or absence of *Mycobacterium tuberculosis* in the subject. Accordingly, the method or use of the present invention may optionally comprise the step of confirming the presence or absence of *Mycobacterium tuberculosis* in the subject using a conventional microbiological technique. Conventional microbiological techniques for determining the presence or absence of *Mycobacterium tuberculosis* will be familiar to a person skilled in the art.

Advantageously, the use of the presently claimed biomarkers allows for a quick and easy preliminary diagnosis of active tuberculosis, which can be subsequently verified by a conventional microbiological technique for detecting *Mycobacterium tuberculosis*. A positive preliminary diagnosis of active tuberculosis using the presently claimed biomarkers allows the patient to begin immediate treatment without delay, thereby improving the prognosis whilst at the same time reducing the potential spread of the disease. On the other hand, a negative preliminary diagnosis using the presently claimed biomarkers avoids the unnecessary treatment of patients that do not have active tuberculosis, thereby avoiding possible adverse effects such as drug toxicity and/or resistance, and the otherwise inevitable waste of valuable resources.

Biomarker Level

The method of the present invention comprises the step of determining a level of one or more biomarkers selected from:

(a) basic leucine zipper transcription factor ATF-like 2 (BATF2)
(b) cluster of differentiation 177 (CD177);
(c) haptoglobin (HP);
(d) immunoglobulin J chain (IGJ); and
(e) galectin 10 (CLC);

in a sample. Preferably, the sample is obtained from a subject.

The method according to the present invention may further comprise the step of comparing the level of said one or more biomarkers in a sample to a reference value, wherein the level of the one or more biomarkers in the sample compared to the reference value is indicative of the presence or absence of active tuberculosis in the subject.

By "determining a level" it is meant measuring—either quantitatively or semi-quantitatively—the amount of a particular substance. Typically, the determination will reveal the absolute level of a substance in a sample from a subject, or the level of a substance relative to the level of a reference sample or value.

A level of a substance may be determined more than once in a given sample, for example for the purpose of statistical calculations. Alternatively or in addition, a level may be determined one or more times in more than one sample obtained from a subject.

In a preferred embodiment, the level of the biomarker of the invention is determined in the form of a mRNA transcript.

In one embodiment, the level of a mRNA transcript biomarker of the invention is measured or determined relative to the level of a reference mRNA transcript biomarker value.

Applicable techniques for determining the level of a biomarker in accordance with the present invention are known to the person skilled in the art.

Such techniques include, but are not limited to, Northern blot analysis, nuclease protection assays (NPA) e.g. RNAse protection assays, reverse transcriptase-PCR (RT-PCT), quantitative PCR (qPCR), array, microarray, DNA microchip, DNA sequencing including mini-sequencing, primer extension, hybridization with allele-specific oligonucleotides (ASO), oligonucleotide ligation assays (OLA), PCR using allele-specific primers (ARMS), dot blot analysis, flap probe cleavage approaches, restriction fragment length polymorphism (RFLP), kinetic PCR, and PCR-SSCP, in situ hybridisation, fluorescent in situ hybridisation (FISH), pulsed field gel electrophoresis (PFGE) analysis, Southern blot analysis, single stranded conformation analysis (SSCA), denaturing gradient gel electrophoresis (DGGE), temperature gradient gel electrophoresis (TGGE), denaturing HPLC (DHPLC), and combinations of the above, all of which are known to the person skilled in the art.

In a preferred embodiment, the mRNA level is determined by one or more of RT-PCR, qPCR, microarray or RNA sequencing.

As used herein, an "array" includes any two-dimensional or substantially two-dimensional (as well as a three-dimensional) arrangement of addressable regions bearing a particular chemical moiety or moieties (e.g., biopolymers—such as polynucleotide or oligonucleotide sequences (nucleic acids), polypeptides (e.g., proteins), carbohydrates, lipids, etc.). The array may be an array of polymeric binding agents—such as polypeptides, proteins, nucleic acids, polysaccharides or synthetic mimetics. Typically, the array is an array of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

An array or microchip for use with the present invention typically consists of thousands of distinct nucleotide probes which are built up in an array on a silicon chip. Nucleic acid to be analyzed is fluorescently labelled, and hybridized to the probes on the chip. This method is one of parallel processing of thousands of probes at once and can tremendously accelerate the analysis. In several publications the use of this method is described (*Nature Genetics,* 1996; 14: 441; *Nature Genetics,* 1996; 14: 450; *Science,* 1996; 274: 610; *Nature Genetics,* 1996; 14: 457; *Genome Res,* 2000; 10: 853).

Determination of mRNA biomarkers may be accomplished by reverse transcription, amplification, for instance by PCR, from the resulting cDNA and gel electrophoresis and/or optionally sequencing of the amplified nucleic acid using techniques well known in the art.

As such, mRNA biomarkers according to the present invention may be analysed using one or more primer pairs or probes. In one particularly preferred embodiment, the probe is selected from SEQ ID NOS: 10-14 as described herein.

In a preferred embodiment, the level of the biomarker of the invention is determined by detecting protein (polypeptide) levels.

The step of determining the level of the biomarker of the invention may involve detection of the polypeptide using a technique such as flow cytometry, antibody-based arrays, enzyme linked immunosorbent assay (ELISA), non-antibody protein scaffolds (e.g. fibronectin scaffolds), radioimmuno-assay (MA), western blotting, aptamers or mass spectrometry for example.

An ELISA may be performed according to general methods which are known in the art. For example, the ELISA may be a sandwich or competitive ELISA.

Various enzyme-substrate labels are available for use with such ELISAs, e.g. as disclosed in U.S. Pat. No. 4,275,149. The enzyme generally catalyses a chemical alteration of the chromogenic substrate that can be detected. For example, the enzyme may catalyse a colour change in a substrate, or may alter the fluorescence or chemiluminescence of the substrate. Examples of enzymatic labels include peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are well known.

Determination using aptamers is also known in the art. Aptamers can be single strand DNA or RNA sequences that fold in a unique 3D structure having a combination of stems, loops, quadruplexes, pseudoknots, bulges, or hairpins. The molecular recognition of aptamers results from intermolecular interactions such as the stacking of aromatic rings, electrostatic and van der Waals interactions, or hydrogen bonding with a target compound. In addition, the specific interaction between an aptamer and its target is complemented through an induced fit mechanism, which requires the aptamer to adopt a unique folded structure to its target. Aptamers can be modified to be linked with labeling molecules such as dyes, or immobilized on the surface of beads or substrates for different applications.

Aptamers can be paired with nanotechnology, microarray, microfluidics, mass spectrometry and other technologies for quantification in a given sample.

The timing of the determination of the biomarker level is not particularly restricted. Typically, the level will be determined in a sample from a subject who is showing signs or symptoms of active tuberculosis. In an advantageous embodiment, the biomarker level is able to predict the onset of active tuberculosis in a sample from a subject who is not already showing signs or symptoms of the disease. In another advantageous embodiment, the biomarker level is able to act as a surrogate endpoint of response to anti-tuberculosis treatment or therapy.

Thus the present invention also provides methods for predicting the onset of active tuberculosis in a sample from a subject who is not already showing signs or symptoms of the disease, the method comprising determining the level of one or more biomarkers of the invention. BATF2 is a particularly useful biomarker in this aspect of the invention.

Accordingly, in one embodiment of the invention, the step of determining a level of one or more of the biomarkers of the invention is carried out:

(a) before the onset of active tuberculosis in the subject; and/or (b) whilst the subject is showing symptoms of active tuberculosis; and/or (c) during and/or after the use of an anti-tuberculosis agent to treat the active tuberculosis.

For example, the level may be determined up to about 12 months, preferably about 3 months before the onset of disease e.g. the appearance of signs or symptoms of active tuberculosis. The level may also be determined at around 8 weeks or more after the start of treatment of the subject with an anti-tuberculosis agent.

By "increase in the level of a biomarker" or "increased level of a biomarker", it is meant that the relative or absolute level of the biomarker is of a substantially higher value compared to a reference (or baseline) value.

By "decrease in the level of a biomarker" or "decreased level of a biomarker" it is meant that the relative or absolute level of the biomarker is of a substantially lower value compared to a reference (or baseline) value.

In embodiments of the present invention, an increased level of a biomarker in the test sample compared to the reference value is indicative of the presence of active tuberculosis in the subject. In embodiments of the present invention, a decreased level of a biomarker in the test sample compared to the reference value is indicative of the presence of active tuberculosis in the subject. In such embodiments, preferably the level of biomarker in the test sample differs by at least 1%, at least 5%, at least 10%, at least 20%, at least 30%, at least 50%, at least 75% or at least 100% compared to the reference value or the reference value range, or the mean of the reference value range.

More preferably, the level of biomarker in the test sample differs by at least 2-fold, for example at least 3-fold, 4-fold, 5-fold, 6-fold, 8-fold or 10-fold compared to the reference value or the reference value range or the mean of the reference value range.

Most preferably, the level of biomarker in the test sample differs by at least 2-fold compared to the mean of the reference value range.

By "unchanged level of a biomarker" it is meant that the relative or absolute level of the biomarker is of substantially the same value compared to a reference value, or lies within the reference value range.

In one embodiment, an unchanged level means a level which differs by less than 2-fold, such as less than 1.5-fold, compared to the reference value, the reference value range or the mean of the reference value range.

As will be apparent to the person skilled in the art, the actual determination of whether a level is substantially increased, decreased or unchanged compared to a reference (or baseline) value may depend on the outcome of one or more statistical analyses, all of which are known and are routine to the person skilled in the art.

Reference Value

In certain embodiments of the present invention, biomarker levels are compared to reference values.

"Reference values" include but are not limited to, values obtained from reference subjects (and samples obtained therefrom), or pre-determined absolute values.

Typically, a reference value is derived from a healthy subject, a subject known to be suffering from a particular condition or disease, or a subject who has recovered from a particular condition or disease.

In the context of the present invention, the reference value may be derived from one or more of:

(a) a subject with no prior tuberculosis exposure;

(b) a subject having a latent tuberculosis infection (LTBI);

(c) a subject who has recovered from tuberculosis;

(d) a subject suffering from a non-tuberculosis disease or non-tuberculosis infectious disease;

(e) a subject suffering from non-tuberculosis pneumonia or non-tuberculosis febrile disease.

The reference value may be, for example, a predetermined measurement of a level of ICJ, HP, CLC, CD177 or BATF2 which is present in a sample from a normal subject, i.e. a subject who is not suffering from active tuberculosis or any of (a) to (e) above. The reference value may, for example, be based on a mean or median level of the biomarker in a control population of subjects, e.g. 5, 10, 100, 1000 or more subjects (who may either be age- and/or gender-matched or unmatched to the test subject) who show no symptoms of active tuberculosis.

The reference value may be determined using corresponding methods to the determination of biomarker level in the test sample, e.g. using one or more samples taken from a control population of subjects. For instance, in some embodiments biomarker levels in reference value samples may be determined in parallel assays to the test samples. In alternative embodiments, the reference value may have been previously determined, or may be calculated or extrapolated, without having to perform a corresponding determination on a reference value with respect to each test sample obtained.

In one embodiment, the reference value is derived from a subject suffering from active tuberculosis.

In one embodiment, the reference value is derived from the same subject, but at an earlier time. Thus, the invention may enable the status of a subject, such as disease progression in a subject, to be monitored over time. In particular, this embodiment finds utility when monitoring the response to anti-tuberculosis therapy over time.

Reference values of the present invention may also be derived from a HIV-negative subject.

In a preferred embodiment, the reference value is a range of values. For example, it may be determined that healthy subjects present levels of a biomarker of the invention within a particular "healthy" range. Equally, subjects suffering from active tuberculosis may present levels of a biomarker of the invention within a particular "disease" range. Reference values, and in particular ranges of values may be optimised over time as more data are obtained and analysed.

In one embodiment, a level of BATF2 is determined in a sample obtained from a subject, and a higher level of BATF2 in the sample from the subject compared to a subject with no prior tuberculosis exposure is indicative of the presence active tuberculosis, for example active pulmonary tuberculosis or active extrapulmonary tuberculosis.

In a related embodiment, a level of BATF2 is determined in a sample obtained from a subject, and a higher level of BATF2 in the sample from the subject compared to a subject who has recovered from tuberculosis is indicative of the presence active tuberculosis.

In a related embodiment, a level of BATF2 is determined in a sample obtained from a subject, and a higher level of BATF2 in the sample from the subject compared to a subject having a latent tuberculosis infection (LTBI) is indicative of the presence active tuberculosis. One or both of the subjects in this embodiment may be children. The subject, in particular the subject from which the sample is obtained, may be HIV-positive or HIV-negative. The active tuberculosis may be active pulmonary tuberculosis.

In a related embodiment, a level of BATF2 is determined in a sample obtained from a subject, and a higher level of BATF2 in the sample from the subject compared to an HIV-negative subject having a latent tuberculosis infection (LTBI) is indicative of the presence active tuberculosis.

In a related embodiment, a level of BATF2 is determined in a sample obtained from a subject, and an unchanged level of BATF2 in the sample from the subject compared to one or more of:
 (a) a subject with no prior tuberculosis exposure;
 (b) a subject having a latent tuberculosis infection (LTBI);
 (c) a subject who has recovered from tuberculosis;
 (d) a subject suffering from a non-tuberculosis infectious disease; and
 (e) a subject suffering from non-tuberculosis pneumonia or non-tuberculosis febrile disease
is indicative of the absence of active tuberculosis.

In some embodiments wherein a level of BATF2 is determined, the reference value is not derived from a subject suffering from a fever or non-tuberculosis febrile disease.

In one embodiment, the level of BATF2 is at least 1.5-fold or at least 2-fold higher in a sample obtained from a subject suffering from active tuberculosis, compared to a reference value derived from a subject with no prior tuberculosis exposure or a subject suffering from a non-tuberculosis infectious disease. More preferably, the level of BATF2 is at least 3-fold higher, or at least 4-fold, or at least 5-fold, or at least 6-fold, or at least 7-fold, or at least 8-fold or at least 9-fold or at least 10-fold higher compared to a reference value derived from a subject with no prior tuberculosis exposure or a subject suffering from a non-tuberculosis infectious disease.

In one embodiment, a level of IGJ is determined in a sample obtained from a subject, and a higher level of IGJ in the sample from the subject compared to a subject suffering from non-tuberculosis febrile disease is indicative of the presence of active tuberculosis.

In a related embodiment, a level of CLC is determined in a sample obtained from a subject, and a higher level of CLC in the sample from the subject compared to a subject suffering from non-tuberculosis febrile disease is indicative of the presence of active tuberculosis.

In a related embodiment, a level of HP is determined in a sample obtained from a subject, and a lower level of HP in the sample from the subject compared to a subject suffering from non-tuberculosis febrile disease is indicative of the presence of active tuberculosis.

In a related embodiment, a level of HP is determined in a sample obtained from a subject, and a lower level of HP in the sample from the subject compared to a subject suffering from non-tuberculosis febrile disease is indicative of the presence of a non-tuberculosis disease.

In a related embodiment, a level of CD177 is determined in a sample obtained from a subject, and a lower level of CD177 in the sample from the subject compared to a subject suffering from non-tuberculosis febrile disease is indicative of the presence of active tuberculosis.

In a related embodiment, a level of CD177 is determined in a sample obtained from a subject, and a higher level of CD177 in the sample from the subject compared to a subject suffering from non-tuberculosis febrile disease is indicative of the presence of a non-tuberculosis disease.

In a related embodiment, levels of BATF2 and CD177 are determined in a sample obtained from a subject, and a higher level of BATF2 coupled with a lower level of CD177 in the sample from the subject compared to a subject with no prior tuberculosis exposure or a subject suffering from a non-tuberculosis infectious disease is indicative of the presence of active tuberculosis, for example active pulmonary tuberculosis or active extrapulmonary tuberculosis.

In a related embodiment, levels of IGJ, HP, CLC and CD177 are determined in a sample obtained from a subject, and a higher level of IGJ and CLC coupled with a lower level of HP and CD177 in the sample from the subject compared to a subject suffering from non-tuberculosis febrile disease is indicative of the presence of active tuberculosis, for example active pulmonary tuberculosis or active extrapulmonary tuberculosis.

In a related embodiment, levels of BATF2, CD177, HP, IGJ and CLC are determined in a sample obtained from a subject, and a higher level of IGJ, CLC and BATF2 coupled with a lower level of HP and CD177 in the sample from the subject compared to a reference value—in particular a reference value derived from a subject suffering from non-tuberculosis febrile disease—is indicative of the presence of active tuberculosis, for example active pulmonary tuberculosis or active extrapulmonary tuberculosis.

In some embodiments, the change in level of the biomarker of the invention in the sample compared to the reference value is predictive of the onset of active tuberculosis, e.g. in a sample from a subject who is not already showing signs or symptoms of the disease.

In a preferred embodiment, a level of BATF2 is determined in a sample obtained from a subject, and a higher level of BATF2 in the sample from the subject compared to a reference value—in particular a reference value from a subject with no prior tuberculosis exposure—is predictive of the onset of active tuberculosis.

In this manner, the method or use of the present invention may be predictive of the onset of active tuberculosis for up to 12 months, for example up to 3, 6 or 9 months before the onset of disease.

In a preferred embodiment, the level of the biomarker of the invention and/or the reference value is standardised by comparison to one or more housekeeping genes, proteins or markers.

Levels of housekeeping genes, proteins or markers are known in the art not to fluctuate in response to varying experimental conditions. Suitable housekeeping genes are known in the art and are described in Silver N., et al (BMC Mol Biol. 2006 Oct. 6; 7:33; "Selection of housekeeping genes for gene expression studies in human reticulocytes using real-time PCR")

Suitable examples include, but are not limited to, GAPDH (glyceraldehyde 3-phosphate dehydrogenase), β-actin, SDHA (succinate dehydrogenase), HPRT1 (hypoxanthine phosphoribosyl transferase 1), HBS1L (HBS1-like protein), AHSP (alpha haemoglobin stabilising protein) and B2M (beta-2-microglobulin). GAPDH is particularly preferred. The skilled person would appreciate that any housekeeping gene, protein or marker could be used for the purposes of the invention.

Surrogate Endpoints

The biomarkers of the present invention may be advantageously used (e.g. in vitro) as surrogate endpoints of successful therapy with an anti-tuberculosis agent.

According to one embodiment of the method or use of the present invention, the level of one or more of BATF2, CD177, HP, IGJ and CLC is determined, and a decreased level of BATF2 and/or IGJ and/or CLC, and/or an increased level of HP and/or CD177 in a sample compared to a reference value is indicative of the absence of active tuberculosis and/or successful/effective therapy with an anti-tuberculosis agent.

In a particular embodiment, the level of BATF2 is determined, and a decreased level of BATF2 in the sample compared to a reference value is indicative of the absence of active tuberculosis and/or successful/effective therapy with an anti-tuberculosis agent.

The sample and the reference value may be derived from the same subject, for example at different time points. In this embodiment, the reference value may be derived from the subject at an earlier time point (time point "A") e.g. when the subject is suffering from active tuberculosis and/or is not undergoing anti-tuberculosis therapy and/or concurrent with the start of anti-tuberculosis therapy. The (test) sample may then be taken from the subject at a later time point (time point "B") e.g. when anti-tuberculosis therapy has begun, has completed and/or signs and symptoms of active tuberculosis have waned or are no longer present.

The period of time between time point "A" and time point "B" may be of any length. Advantageously, the time period is around 8 weeks or more than 8 weeks. For example, there may be around or more than 8 weeks between the start of anti-tuberculosis therapy (at which point the reference value is derived) and the taking of the (test) sample from the subject.

Kit

The present invention provides a kit for determining the presence or absence of active tuberculosis in a subject, wherein the kit comprises one or more primer pairs or probes capable of determining a level of one or more biomarkers selected from the group consisting of:
(a) basic leucine zipper transcription factor ATF-like 2 (BATF2)
(b) cluster of differentiation 177 (CD177);
(c) haptoglobin (HP);
(d) immunoglobulin J chain (IGJ); and
(e) galectin 10 (CLC);
in a sample obtained from the subject; wherein the kit optionally comprises a set of instructions.

In one embodiment, the one or more primer pairs or probes are immobilised on a solid support.

The kit of the invention may comprise a plurality of probes, each capable of hybridising specifically to one of the alternative biomarkers of the invention.

As used herein, the term "probe" refers to a nucleic acid (eg. an oligonucleotide or a polynucleotide sequence) that is complementary to a nucleic acid sequence present in a sample, such that the probe will specifically hybridize to the nucleic acid sequence present in the sample under appropriate conditions.

In one particularly preferred embodiment, the probe is selected from SEQ ID NOS: 10-14 as described herein.

The kit may also comprise means for detecting the presence of one or more hybridization products, corresponding to each probe/biomarker combination.

The probes may be gene probes, for example oligomeric DNA sequences of 15 to 50 bases which are synthesized to detect the presence of a biomarker. The probe may then be hybridized to the biomarker under stringent conditions.

Alternatively the kit may comprise one or more primer pairs, using which each biomarker may detected by:
a) amplifying the potential nucleic acid biomarker or biomarker-containing parts of the nucleic acid in said sample;
b) sequencing, e.g. mini-sequencing, the amplified nucleic acids; and
c) detecting the presence or absence of the biomarkers in said sample.

The kit may optionally comprise a reverse transcriptase enzyme.

The term "primer" as used herein refers to an oligonucleotide which is capable of acting as a point of initiation of synthesis when placed under conditions in which synthesis of a primer extension product which is complementary to a nucleic acid strand is induced, i.e. in the presence of nucleotides and an inducing agent—such as DNA polymerase and at a suitable temperature and pH.

The primers and/or probes may be labelled in order to facilitate their detection. Such labels (also known as reporters) include, but are not limited to, radioactive isotopes, fluorophores, chemiluminescent moieties, enzymes, enzyme substrates, enzyme cofactors, enzyme inhibitors, dyes, metal ions, metal sols, other suitable detectable markers—such as biotin or haptens and the like. Particular example of labels which may be used include, but are not limited to, fluorescein, 5(6)-carboxyfluorescein, Cyanine 3 (Cy3), Cyanine 5 (Cy5), rhodamine, dansyl, umbelliferone, Texas red, luminal, NADPH and horseradish peroxidase.

The probes and/or primers used in the kit hybridise specifically to their target nucleic acid sequence. They may, for example, hybridise under high-stringency conditions.

Stringency of hybridisation refers to conditions under which polynucleic acids hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature.

As used herein, high stringency refers to conditions that permit hybridisation of only those nucleic acid sequences that form stable hybrids in 1 M sodium at 65-68° C. High stringency conditions can be provided, for example, by hybridisation in an aqueous solution containing 6× SSC, 5× Denhardt's, 1% SDS (sodium dodecyl sulphate), 0.1% sodium pyrophosphate and 0.1 mg/ml denatured salmon sperm DNA as non specific competitor.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) *Molecular Cloning: A Laboratory Manual*, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the hybridising pair also play a role.

In the kit of the present invention, nucleic acid probes may be associated with a support or substrate to provide an array of nucleic acid probes to be used in an array assay. Suitably, the probe is pre-synthesized or obtained commercially, and then attached to the substrate or synthesized on the substrate, i.e., synthesized in situ on the substrate.

A specific method of nucleic acid hybridization that can be utilized is nucleic acid chip/array hybridization in which nucleic acids are present on a immobilized surface—such as a microarray and are subjected to hybridization techniques sensitive enough to detect minor changes in sequences.

Array technology and the various techniques and applications associated with it are generally known to the person skilled in the art.

Kits according to the present invention may additionally comprise an analysis device to determine the level of one or more biomarkers in the sample using the primer pairs or probes.

The kit may comprise a storage medium storing a program for controlling a data processing apparatus to classify the subject based on the level of the one or more biomarkers determined in the sample using the primer pairs or probes.

The program may comprise instructions for controlling the data processing apparatus to provide a risk indication for the subject.

In a further aspect, the present invention provides a method of preparing a kit according to the invention, comprising the step of immobilising the one or more primer pairs or probes of the invention on a solid support.

In yet a further aspect, the present invention provides the use of a kit of the invention for determining the presence or absence of active tuberculosis in a subject.
Sample The sample may be or may be derived from a biological sample, such as a blood sample, cheek swab, a biopsy specimen, a tissue extract, an organ culture or any other tissue or cell preparation from a subject.

In theory, the presence of an mRNA transcript biomarker according to the present invention can be determined by extracting mRNA from any tissue of the body.

The sample may be or may be derived from an ex vivo sample.

Preferably, the sample is, or is derived from blood, in particular peripheral blood.

Preferably, the sample is, or is derived from, whole blood or a fraction of whole blood.

In embodiments wherein the biomarker of the invention is a polypeptide (e.g. BATF2 polypeptide), the sample may be, or may be derived from, blood cells.
Subject The subject may be a human. The subject may be any age, gender or ethnicity. The subject may be a human adult or a human child. In the context of the present invention, a "human adult" is a human subject of 15 years of age or older at the time of sampling, and a "human child" is a human subject of less than 15 years of age at the time of sampling.

The subject may show one or more signs or symptoms of tuberculosis. The subject may have been previously characterised as having tuberculosis by other diagnostic methods. Where the results of previous tests are ambiguous or inconclusive, the method of the present invention may be used to confirm the diagnosis.

The subject may have a predisposition to develop active tuberculosis. For example, there may be an increased risk or likelihood that the subject will develop active tuberculosis at some point in the future. A predisposition may be due to a diagnosis of LTBI.

Methods for calculating a "risk indication" to provide a quantitative analysis of a subject's likelihood of having active tuberculosis are described herein.

The risk indication may be provided as a continuous quantitative measure, for example as a probability estimate from 0 to 1, where "0" represents an impossibility that a subject is suffering from active tuberculosis, and "1" represents an absolute certainty that a subject is suffering from active tuberculosis.

By "a subject who has recovered from tuberculosis", it is meant that the subject previously suffered from active tuberculosis, but at the time of sampling showed no signs or symptoms of tuberculosis. For example, the recovered subjected may be two years or more post-recovery, or may be two to four years post-completion of TB therapy.

By "healthy subject", it is meant, for example, that:
(i) the subject has had no prior exposure to Mtb or tuberculosis; or
(ii) the subject has LTBI; or
(iii) the subject has recovered from tuberculosis; or
(iv) the subject suffers from no illness whatsoever.

In some embodiments, the subject is HIV-negative.
Therapy of Tuberculosis

The present invention provides compositions comprising a therapeutically effective amount of an anti-tuberculosis agent for use in the treatment of active tuberculosis in a subject identified as requiring treatment of active tuberculosis by a method of the present invention.

The present invention also provides methods of treating active tuberculosis in a subject identified as requiring treatment of active tuberculosis by the method of determining the presence or absence of active tuberculosis as described herein, comprising administering a therapeutically effective amount of an anti-tuberculosis agent to the subject.

In particular, the present invention provides a method of treating active tuberculosis in a subject, comprising:
(a) determining the presence of active tuberculosis, by a method as described herein;
(b) administering a therapeutically effective amount of an anti-tuberculosis agent to the subject.

The method of treating active tuberculosis in a subject may further comprise (c) repeating step (a) after administration of the anti-tuberculosis agent. If the active tuberculosis is still present (as compared to that determined in step (a)), the method for treating active tuberculosis in a subject may further comprise a step (d) which comprises administering an alternative anti-tuberculosis agent to the subject, wherein the alternative anti-tuberculosis agent differs from the anti-tuberculosis agent administered in step (b).

The anti-tuberculosis agent may be any suitable agent that can treat or alleviate the signs and/or symptoms of active tuberculosis. The agent can be one or more anti-tuberculosis agents that may be administered over a time course and/or simultaneously or at different times.

In a preferred embodiment, the anti-tuberculosis agent is one or more selected from the group consisting of: an antibiotic, a corticosteroid, a chemotherapeutic agent and a TNF inhibitor.

The antibiotic or chemotherapeutic agent may be selected from the group consisting of: isoniazid, rifampicin, pyrazinamide, streptomycin, para-aminosalicylic acid (PAS), moxifloxacin, ciprofloxacin, ethambutol, and combinations thereof. The corticosteroid may be selected from the group consisting of: prednisolone, dexamethasone and combinations thereof. The TNF inhibitor may be selected from the group consisting of infliximab, adalimumbab, certolizumab, etanercept, and combinations thereof.

Suitable dosage amounts and regimens of anti-tuberculosis agents to be used in conjunction with the present invention may be adequately determined by the person skilled in the art.

For example, an anti-tuberculosis agent may be formulated and administered to a subject in any suitable composition for the treatment of active tuberculosis. In particular embodiments, an effective amount of the anti-tuberculosis agent is administered to the subject. In this context, the term "effective amount" means an amount effective, at dosages and for periods of time necessary to achieve the desired result, for example, to treat the active tuberculosis.

The anti-tuberculosis agent may be administered to a subject using a variety of techniques. For example, the agent may be administered systemically, which includes by injection including intramuscularly or intravenously, orally, sublingually, transdermally, subcutaneously, internasally. Alternatively, the agent may be administered directly at a site affected by the active tuberculosis.

The concentration and amount of the anti-tuberculosis agent to be administered will typically vary, depending on, for example, the severity of the active tuberculosis, the tissues associated with and affected by active tuberculosis, the type of agent that is administered, the mode of administration, the age and health of the subject, and the like.

The anti-tuberculosis agent may be formulated in a pharmaceutical composition together with a pharmaceutically acceptable carrier, vehicle, excipient or diluent. The compositions may routinely contain pharmaceutically acceptable concentrations of salt, buffering agents, preservatives and various compatible carriers. For instance the anti-tuberculosis agent may be formulated in a physiological buffer solution.

The proportion and identity of the pharmaceutically acceptable carrier, vehicle, excipient or diluent may be determined by the chosen route of administration, compatibility with live cells, and standard pharmaceutical practice. Generally, the pharmaceutical composition will be formulated with components that will not significantly impair the biological properties of the agent. Suitable carriers, vehicles, excipients and diluents are described, for example, in Remington's Pharmaceutical Sciences (Remington's Pharmaceutical Sciences, Mack Publishing Company, Easton, Pa., USA 1985).

In a related aspect, the present invention also provides a method of determining whether a subject will be susceptible to treatment with an anti-tuberculosis agent, said method comprising the step of determining a level of one or more of the following biomarkers:
(a) basic leucine zipper transcription factor ATF-like 2 (BATF2)
(b) cluster of differentiation 177 (CD177);
(c) haptoglobin (HP);
(d) immunoglobulin J chain (IGJ); and
(e) galectin 10 (CLC);
in a sample obtained from the subject; wherein the level of the one or more biomarkers in the sample compared to a reference value is indicative of the susceptibility of the subject to treatment with an anti-tuberculosis agent.

Additional Aspects

The present invention also provides the following additional aspects.

All embodiments and optional features described herein apply equally to the following additional aspects.

Accordingly, in a further aspect, the present invention provides a method for determining the presence or absence of active tuberculosis in a sample, said method comprising the steps of:
(i) determining a level of one or more of the following biomarkers in said sample:
 (a) basic leucine zipper transcription factor ATF-like 2 (BATF2)
 (b) cluster of differentiation 177 (CD177);
 (c) haptoglobin (HP);
 (d) immunoglobulin J chain (IGJ); and
 (e) galectin 10 (CLC);
(ii) optionally comparing the level of said one or more biomarkers in the sample to a reference value, wherein the level of the one or more biomarkers in the sample compared to the reference value is indicative of the presence or absence of active tuberculosis.

In a further aspect still, the present invention provides a method for determining whether a subject is suffering from active tuberculosis or a non-tuberculosis infectious disease, the method comprising the steps of:
(i) determining a level of BATF2 in a sample obtained from the subject;
(ii) comparing the level of BATF2 in the sample to a reference value;
 wherein an unchanged level of BATF2 in the sample from the subject compared to the reference value is indicative of the absence of active tuberculosis; or
 wherein an increased level of BATF2 in the sample from the subject compared to the reference value necessitates the execution of the following additional method steps:
(iii) determining the levels of the group of biomarkers consisting of: IGJ, HP, CLC, and CD177;
(iv) comparing the levels of IGJ, HP, CLC, and CD177 in the sample to reference values;
 wherein the levels of IGJ, HP, CLC, and CD177 in the sample compared to the reference values is indicative of either:
 (a) the presence of active tuberculosis and the absence of a non-tuberculosis infectious disease in the subject; or
 (b) the presence of a non-tuberculosis infectious disease and the absence of active tuberculosis in the subject.

In a further aspect still, the present invention provides method for determining the presence or absence of active tuberculosis in a subject, the method comprising the step of: determining a level of one or more biomarkers selected from:
(a) basic leucine zipper transcription factor ATF-like 2 (BATF2)
(b) cluster of differentiation 177 (CD177);
(c) haptoglobin (HP);
(d) immunoglobulin J chain (IGJ); and
(e) galectin 10 (CLC);
in a sample obtained from the subject.

Additional Advantages

The present inventors have identified the fewest possible blood transcripts that can discriminate patients with active TB from healthy individuals, and from those with other infectious diseases.

Identification of the fewest possible transcripts means that analysis and processing is less expensive and less time-consuming, which in turn leads to a reduced time to starting treatment of active tuberculosis, or excluding a diagnosis of active tuberculosis.

The present invention also reduces the need for unnecessary microbiological diagnostic tests for active tuberculosis, and reduces unnecessary anti-tuberculosis therapy. Unnecessary drug treatment of patients that do not have active tuberculosis can lead to possible toxicity and/or drug resistance problems, as well as considerable wasted costs/resources.

The present invention is particularly advantageous for distinguishing clinically between active TB and other febrile diseases.

The present invention shows that BATF2 is sufficient as a single biomarker to distinguish active TB from healthy individuals. This may be true regardless of HIV status. In HIV infected cases, BATF2 transcript levels offer negative predictive value as a biomarker for active TB.

The present invention also shows that a transcriptional signature comprising four genes (IGJ, HP, CLC and CD177) can be summarised into a single probability score to discriminate between active TB and patients presenting to hospital with non-tuberculosis infectious disease or non-tuberculosis febrile disease.

The present invention can be used to determine the presence or absence of active tuberculosis, regardless of subject age, gender or ethnicity.

The four gene signature performs equally well in discriminating extrapulmonary TB from non TB pneumonia cases in independent data sets, showing that the discriminating transcriptional signatures were not confounded by the site of disease.

The ability of the four gene signature to discriminate TB from other infections offers greatest clinical value in individuals who present with febrile illnesses in the setting of relative low TB incidence, but whose presentation is compatible with pulmonary or extrapulmonary TB.

Thus, the present invention is equally valid for diagnosing both pulmonary and extrapulmonary tuberculosis and does not distinguish between them.

The invention will now be further described by way of Examples, which are meant to serve to assist one of ordinary skill in the art in carrying out the invention and are not intended in any way to limit the scope of the invention.

Variants, Derivatives, Analogues, Homologues and Fragments

In addition to the specific proteins and nucleotides mentioned herein, the invention also encompasses the use of variants, derivatives, analogues, homologues and fragments thereof.

In the context of the invention, a variant of any given sequence is a sequence in which the specific sequence of residues (whether amino acid or nucleic acid residues) has been modified in such a manner that the polypeptide or polynucleotide in question substantially retains its function. A variant sequence can be obtained by addition, deletion, substitution, modification, replacement and/or variation of at least one residue present in the naturally-occurring protein or polynucleotide.

The term "derivative" as used herein, in relation to proteins or polypeptides of the invention includes any substitution of, variation of, modification of, replacement of, deletion of and/or addition of one (or more) amino acid residues from or to the sequence providing that the resultant protein or polypeptide substantially retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence substantially retains the required activity or ability. Amino acid substitutions may include the use of non-naturally occurring analogues.

Proteins used in the invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

Conservative substitutions may be made, for example according to the table below. Amino acids in the same block in the second column and preferably in the same line in the third column may be substituted for each other:

| | | |
|---|---|---|
| ALIPHATIC | Non - polar | G A P |
| | | I L V |
| | Polar - uncharged | C S T M |
| | | N Q |
| | Polar - charged | D E |
| | | K R H |
| AROMATIC | | F W Y |

The term "homologue" as used herein means an entity having a certain homology with the wild type amino acid sequence and the wild type nucleotide sequence. The term "homology" can be equated with "identity".

A homologous sequence may include an amino acid sequence which may be at least 50%, 55%, 60%, 65%, 70%, 75%, 80%, 85% or 90% identical, preferably at least 95% or 97% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the invention it is preferred to express homology in terms of sequence identity.

A homologous sequence may include a nucleotide sequence which may be at least 50%, 55%, 60%, 65%, 70%, 75%, 80%, 85% or 90% identical, preferably at least 95% or 97% or 99% identical to the subject sequence. Although homology can also be considered in terms of similarity, in the context of the invention it is preferred to express homology in terms of sequence identity.

Preferably, reference to a sequence which has a percent identity to any one of the SEQ ID NOs detailed herein refers to a sequence which has the stated percent identity over the entire length of the SEQ ID NO referred to.

Homology comparisons can be conducted by eye or, more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) Nucleic Acids Res. 12: 387). Examples of other software that can perform sequence comparisons include, but are not limited to, the BLAST package (see Ausubel et al. (1999) ibid—Ch. 18), FASTA (Atschul et al. (1990) J. Mol. Biol. 403-410) and the GENEWORKS suite of comparison tools. Both BLAST and FASTA are available for offline and online searching (see Ausubel et al. (1999) ibid, pages 7-58 to 7-60). However, for some applications, it is preferred to use the GCG Bestfit program. Another tool, called BLAST 2 Sequences is also available for comparing protein and nucleotide sequences (see FEMS Microbiol. Lett. (1999) 174: 247-50; FEMS Microbiol. Lett. (1999) 177: 187-8).

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percent homology, preferably percent sequence identity. The software typically does this as part of the sequence comparison and generates a numerical result.

"Fragments" of a full length protein or polynucleotide are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The present invention is further described by way of the following non-limiting examples, and with reference to the following figures.

EXAMPLES

Experimental Methods

Study Participants

Figure 1:
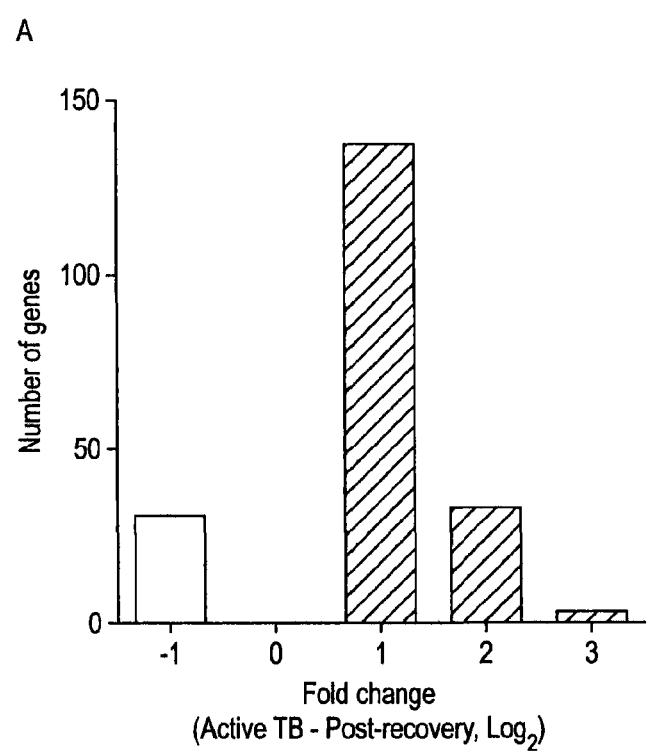
FIG. 1—Blood transcriptional signatures associated with active TB. (A) Statistically significant >2-fold differences in transcript abundance in genome-wide blood transcriptional profiles of patients with active TB compared to post-recovery samples in the AdjuVIT cohort. (B) Gene ontology analysis of the genes in A which were expressed at higher levels in AdjuVIT active TB samples than in the post-recovery samples. (C) Comparison of significant blood gene expression differences in active TB and different healthy states from three different studies—TB post-recovery (AdjuVIT), healthy volunteers (Berry) or people with latent TB (Bloom).
Figure 1:
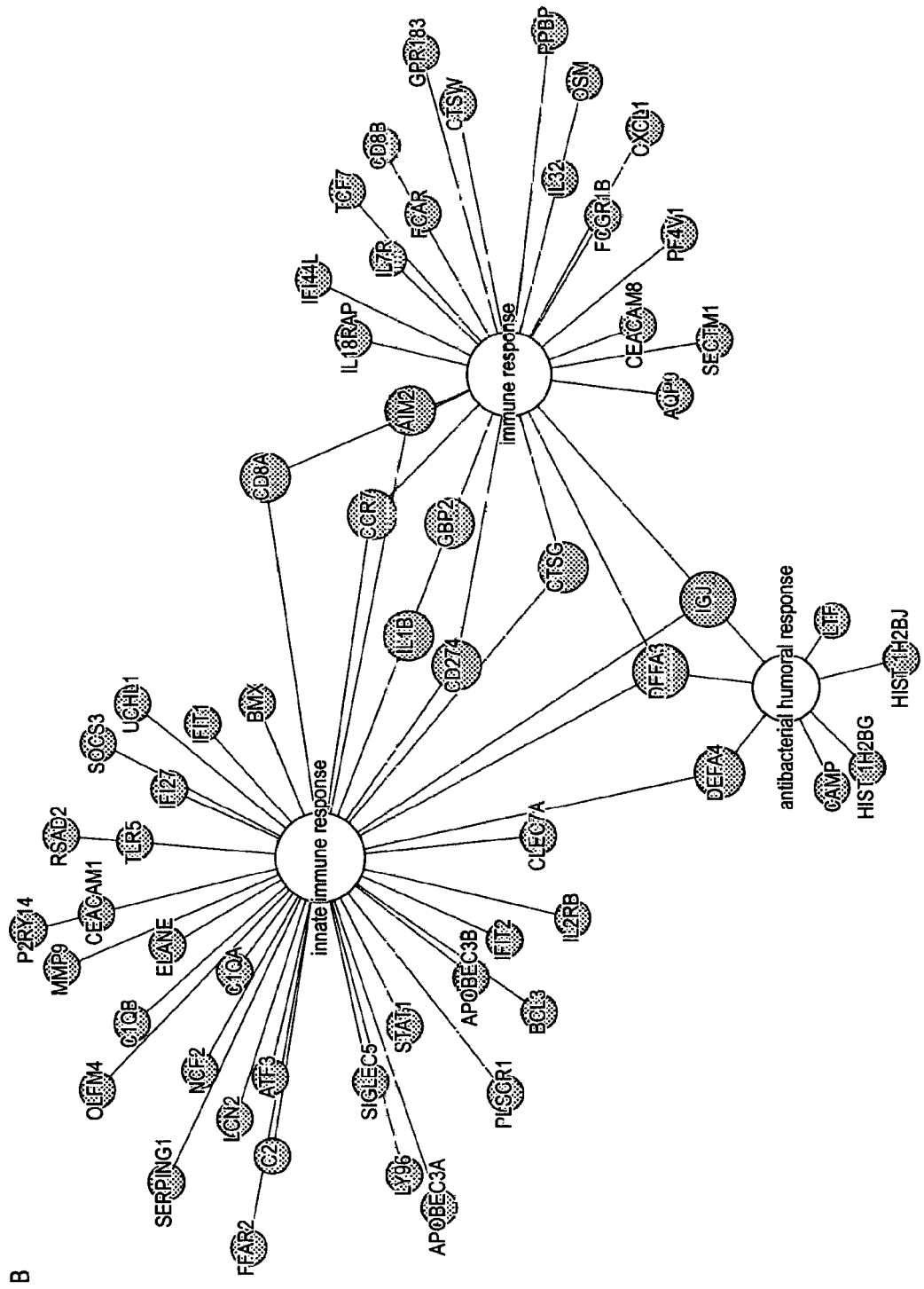
Figure 1:
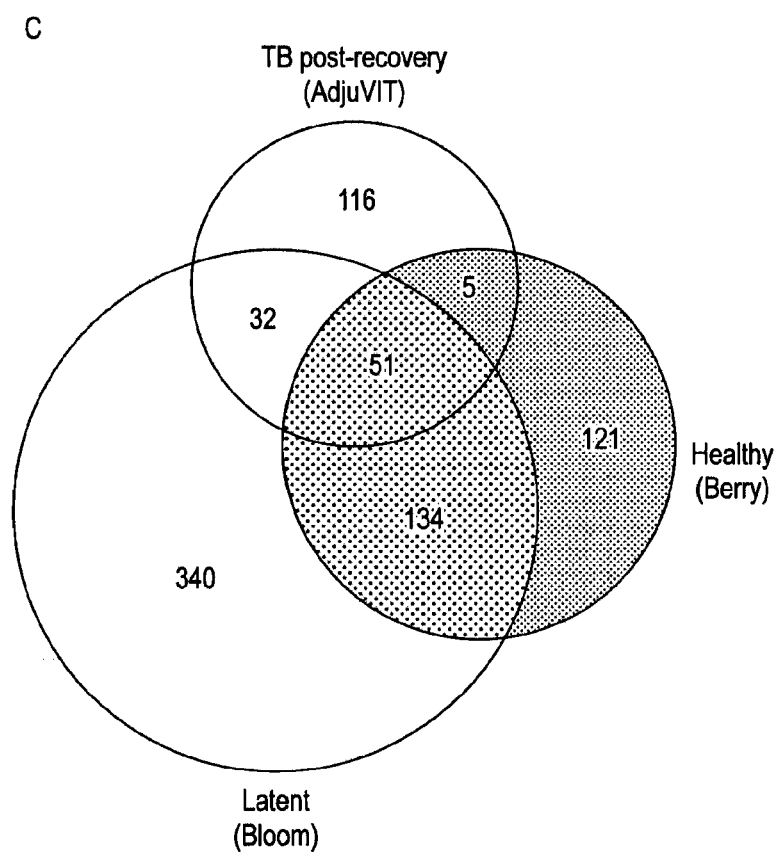

Blood samples were collected in Tempus or Paxgene tubes from healthy volunteers, patients with smear-positive pulmonary TB recruited to the AdjuVIT trial (Martineau et al., 2011) at diagnosis and >2 years post-recovery, patients with pulmonary or extrapulmonary TB in the North Central London TB service, and from patients presenting to University College London Hospital emergency department with fever >38° C. or a clinical diagnosis of pneumonia (based on fever >38° C. and chest radiographic changes) before receipt of antimicrobial treatment.

Peripheral Blood Transcriptional Profiling

RNA was extracted using the Tempus™ Spin RNA Isolation kit (Applied Biosystems) or PAXgene 96 Blood RNA Kit (PreAnalytiX). Genomic DNA was removed with the TURBO DNA-Free™ kit (Ambion). RNeasy MinElute Cleanup kit (Qiagen) was used to concentrate the RNA before globin mRNA depletion with GLOBINclear™ kit (Ambion) and RNA quality control was assessed using the Agilent 2100 Bioanalyzer (Agilent Technologies). Fluorophore labelled cRNA was then generated using the Low Input Quick Amp labelling kit, and hybridised to SurePrint G3 Human Gene Expression v3 8×60K or Human Gene Expression v2 4×44K whole genome microarrays (Agilent Technologies). Array images were acquired with Agilent's dual-laser microarray scanner G2565BA and analysed with Agilent Feature Extraction software (v9.5.1). $\log_2$ transformed median Cy3 and Cy5 signal intensities were normalized using LOESS local linear regression against the mean signal of all the samples using the R package agilp (Chain, *Agilent expression array processing package*; Chain et al., 2010).

Data Analysis

Analysis of all microarray data was conducted on $\log_2$ transformed data (Chain et al., 2010) and restricted to gene symbol annotated probes expressed above background negative control levels in at least one sample. Significant gene expression differences between data sets were identified using Mann Whitney tests for non-parametric data in MultiExperiment Viewer v4.9 (http://www.tm4.org/mev.html) with a false discovery rate of 0.05 and a filter for >two-fold difference in median normalised expression values. Gene ontology and pathway analyses were performed in innateDB (Breuer et al., 2013). Network graphics of gene and pathway association were generated using Gephi (http://gephi.github.io/).

Support vector machines (SVM), which learn an optimum hyperplane separating two sets of data in high dimensional space, were used to classify the transcriptome data from different samples (Cristianini et al., 2000). The R statistical computing platform (v3.0.2) was used to implement the SVM algorithms using the kernlab package with a linear kernel. The SVM was trained and tested on independent data sets. The package outputs either a binary classification, or a probability score for each sample by fitting a logistic regression model to the Euclidean distance of each case from the hyperplane (Platt et al., 1999). The package also outputs a weighting for the importance of each transcript in determining the overall classification. Classification performance was evaluated using receiver operating characteristic (ROC) curves, with the area under the curve (AUC) as a summary statistic. ROC curves were constructed from the output of the SVM using the R package pROC.

Example 1: Comparison of Blood Transcriptomes in Active TB and after Long Term Recovery The AdjuVIT study population comprised HIV-negative patients with smear and culture positive pulmonary TB, in whom we sought to identify the peripheral blood transcriptional signature of active TB by comparison with subjects sampled from the same cohort post-recovery, two to four years after completion of TB treatment (Table 1). This analysis revealed statistically significant and greater than two-fold gene expression differences in 204 unique protein coding transcripts (FIG. 1A). Consistent with other published data, active TB in this cohort was associated with increased expression of genes associated with immune responses (FIG. 1B). In order to evaluate the generalisability of this transcriptional signature in other cohorts of patients with active TB, we compared the differentially expressed gene list in AdjuVIT active TB cases to two other published blood transcriptional signatures in adult patients with active pulmonary TB compared to either healthy volunteers (Berry et al., 2010) or subjects with LTBI (Bloom et al., 2012). 51 unique protein coding transcripts were common to all three studies despite differences in demographic characteristics in each study population and use of different microarray platforms to evaluate the transcriptome (FIG. 1C). Consistent with previous studies (Berry et al., 2010), these transcripts showed significant enrichment for components of interferon (IFN)-associated pathways.

TABLE 1

AdjuVIT cohort

| Patient characteristic | | Active TB (N = 46) | Post-recovery (N = 31) |
|---|---|---|---|
| Median age, years (IQR) | | 30.8 (24.0-37.3) | 33.8 (26.7-39.5) |
| Male gender, N (%) | | 38 (83) | 28 (90) |
| Ethnicity, N (%) | Black/Black African | 13 (28) | 8 (26) |
| | South Asian | 22 (48) | 14 (45) |
| | East Asian | 4 (9) | 1 (3) |
| | European/American | 7 (15) | 8 (26) |
| Median serum 25(OH) vit D (nM) (IQR) | | 14 (0-22) | 17 (11-33) |
| Sputum AFB load, N (%) | Scanty or 1+ | 28 (61) | 12 (39) |
| | 2+ or 3+ | 18 (39) | 19 (61) |
| Cavitation on chest radiograph, N (%) | | 28 (61) | 17 (55) |
| Median TB treatment, days (IQR) | | 2 (0-4) | N/A |

(N = number, SD = standard deviation, AFB = acid fast bacilli.)

Figure 2:
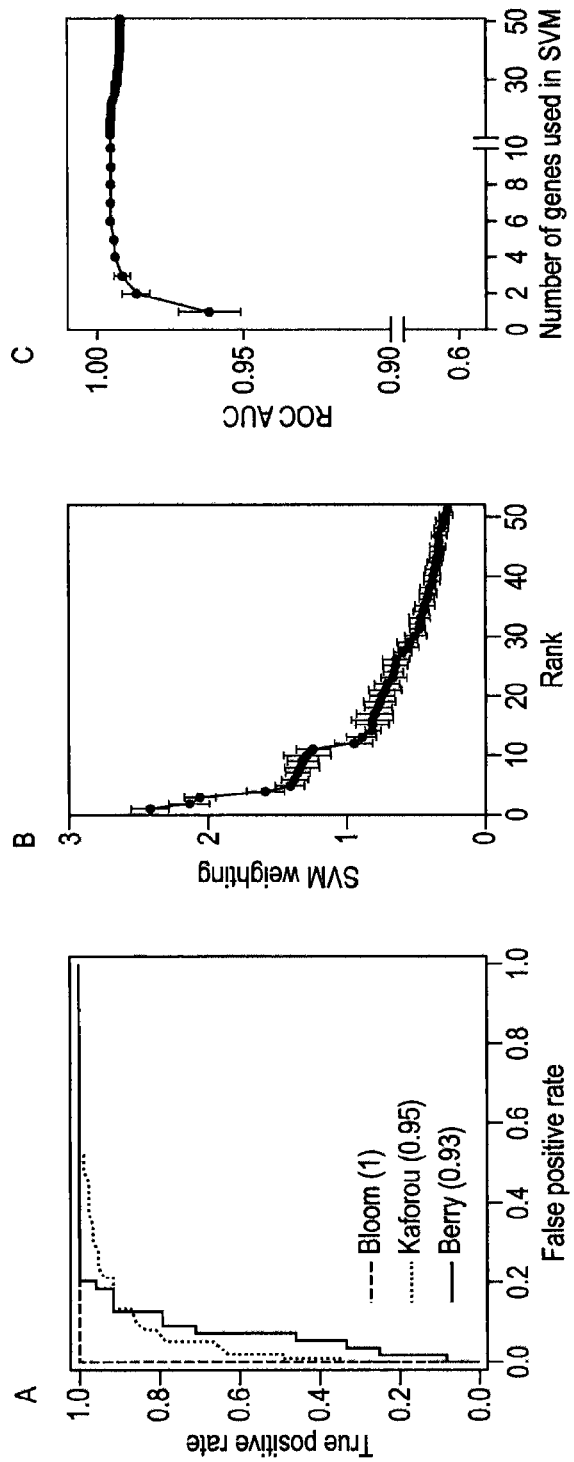
FIG. 2—Transcriptomic classification of active TB and healthy cases using SVM to identify most discriminating features. (A) Receiver operating curve (ROC) performance of support vector machine (SVM) classification of active TB in published data sets comparing HIV negative patients with active TB to healthy volunteers (Berry) or latent TB (Bloom and Kaforou), after training on patients with AdjuVIT active TB at diagnosis vs. post-recovery using 51 blood transcripts identified in FIG. 1C. ROC area under curve (AUC) is shown for each cohort in brackets. (B) Rank order of weightings for each gene in the SVM training model patients with active TB or post recovery. (C) ROC AUC of SVM classification of TB at diagnosis vs. post-recovery using a cumulative number of genes in rank order of weightings. In B-C, data points show mean±95% confidence intervals of SVM results obtained from 100 iterations in which the data set were randomly split into equal training and test sets.

Example 2: Support Vector Machine Classification of Active TB by Comparison with Healthy States In order to discriminate individual cases by their blood transcriptome, we used SVM to derive discriminating models from training data and classify subsequent test cases. Using the 51 transcripts differentially expressed in active TB compared to other healthy states in multiple cohorts (FIG. 1C), we trained an SVM to discriminate between active TB and post-recovery cases using the AdjuVIT study data set. We then evaluated the performance of this SVM model in classifying samples from three separate published studies in HIV negative subjects including a total of 325 cases. These comprised the two previous studies described above including data from active TB and healthy volunteers (Berry cohort) (Berry et al., 2010) or active and latent TB (Bloom cohort) (Bloom et al., 2012), and additional data from a multicentre African study (Kaforou cohort) of adult patients with active and latent TB (Kafourou et al., 2013). ROC curves were used to describe the trade-off between sensitivity and specificity. These showed AUCs of 0.93-1.00, representing excellent classification accuracies (FIG. 2A).

The SVM model calculates a 'weighting' for each dimension of the data, relative to its influence in the classification model. We ranked the 51 genes in order of average SVM weightings, after training on multiple random samples of half the transcriptional data from the AdjuVIT cohort of active TB and post-recovery cases (FIG. 2B). Our aim was to identify the fewest number of transcripts that may be used as a diagnostic biomarker for active TB. Therefore, we tested a cumulative number of genes in rank order of their weightings for their ability to discriminate between active TB and post-recovery cases, using the remaining data which had not been used for training. In order to mitigate against sampling error, we performed 100 random train/test sequences to give average ROC AUC scores (FIG. 2C). Remarkably, this analysis showed that the highest ranked transcript alone, representing expression of the IFN-inducible gene for basic leucine zipper transcription factor (BATF)2, consistently achieved ROC AUC scores>0.95.

Figure 3:
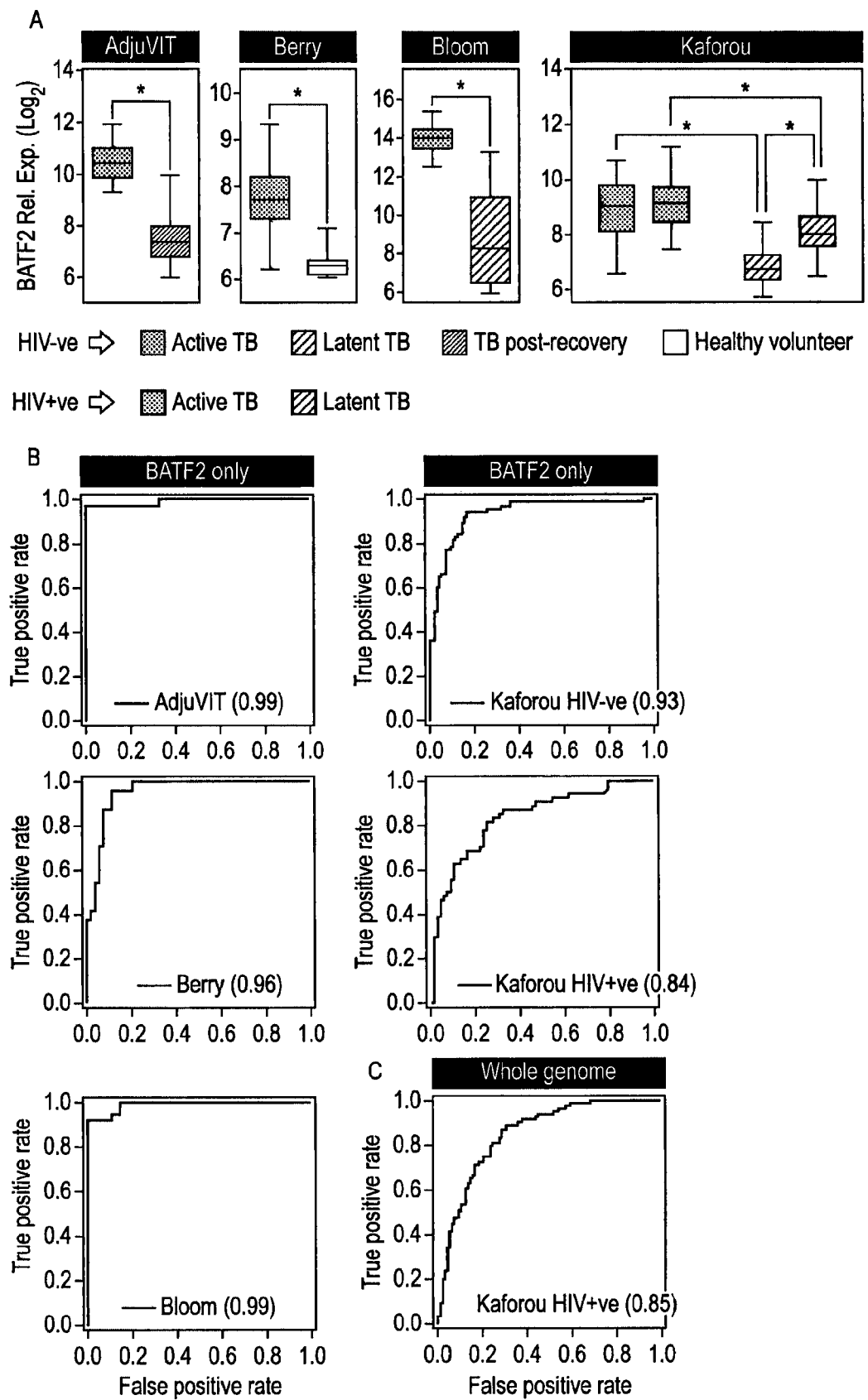
FIG. 3—Classification of active TB and healthy cases using blood BATF2 transcript expression levels. (A) Relative BATF2 gene expression in blood samples from separate HIV negative and HIV positive patient cohorts comparing active TB with either post-recovery patients (AdjuVIT), LTBI (Bloom and Kaforou) or healthy volunteers (Berry). Box and whisker plots represent median, interquartile and full range of data points. *denotes p<0.0001 (Mann-Whitney U test) (B) ROC analyses for discrimination of active TB in each of these cohorts using blood levels of BATF2 expression only. (C) ROC performance of SVM discrimination of active TB from LTBI in HIV positive patients using genome-wide blood transcriptional profiles after training on patients with active TB or post-recovery. In B-C, ROC area under curve is shown in brackets for each cohort.

Example 3: BATF2 Discriminates Active TB from Healthy States in Multiple Study Cohorts Having identified peripheral blood BATF2 transcript levels as a biomarker for active TB in the AdjuVIT cohort, we sought to test its performance in multiple independent cohorts. BATF2 expression in patients with active TB was significantly higher than that of healthy volunteers (Berry cohort) (Berry et al., 2010) and patients with LTBI (Bloom and Kaforou cohorts) (Bloom et al., 2012; Kafourou et al., 2013) irrespective of HIV status, representing data from 402 patients in total (FIG. 3A). Amongst HIV negative patients in these studies, peripheral blood BATF2 expression discriminated between active TB and the various healthy cases described in each cohort with ROC AUC scores of 0.93-0.99 (FIG. 3B). BATF2 levels discriminated less well between active TB and LTBI cases amongst HIV infected patients in the Kaforou cohort (ROC AUC of 0.84). In this cohort, high BATF2 expression in patients with active TB were not significantly affected by HIV co-infection, but LTBI cases with HIV co-infection had significantly higher BATF2 levels than HIV negative cases (FIG. 3A), partially confounding accurate discrimination between active and latent TB in HIV infected patients by this measurement. An SVM model trained using genome-wide data from the AdjuVIT trial to discriminate active TB and post-recovery cases, also achieved a ROC AUC of 0.85 for classification of active and latent TB amongst HIV infected patients from the Kaforou cohort (FIG. 3C).

In conclusion, discrimination of active TB and LTBI cases in HIV infected people using genome wide transcriptional data did not yield better ROC AUC than BATF2 by itself, suggesting that even combinations of other transcripts will not afford better classification accuracy using SVM. Therefore, in the context of HIV-1 infection, inclusion of additional parameters even up to genome-wide level, may not achieve better classification accuracy than BATF2 alone.

Figure 4:
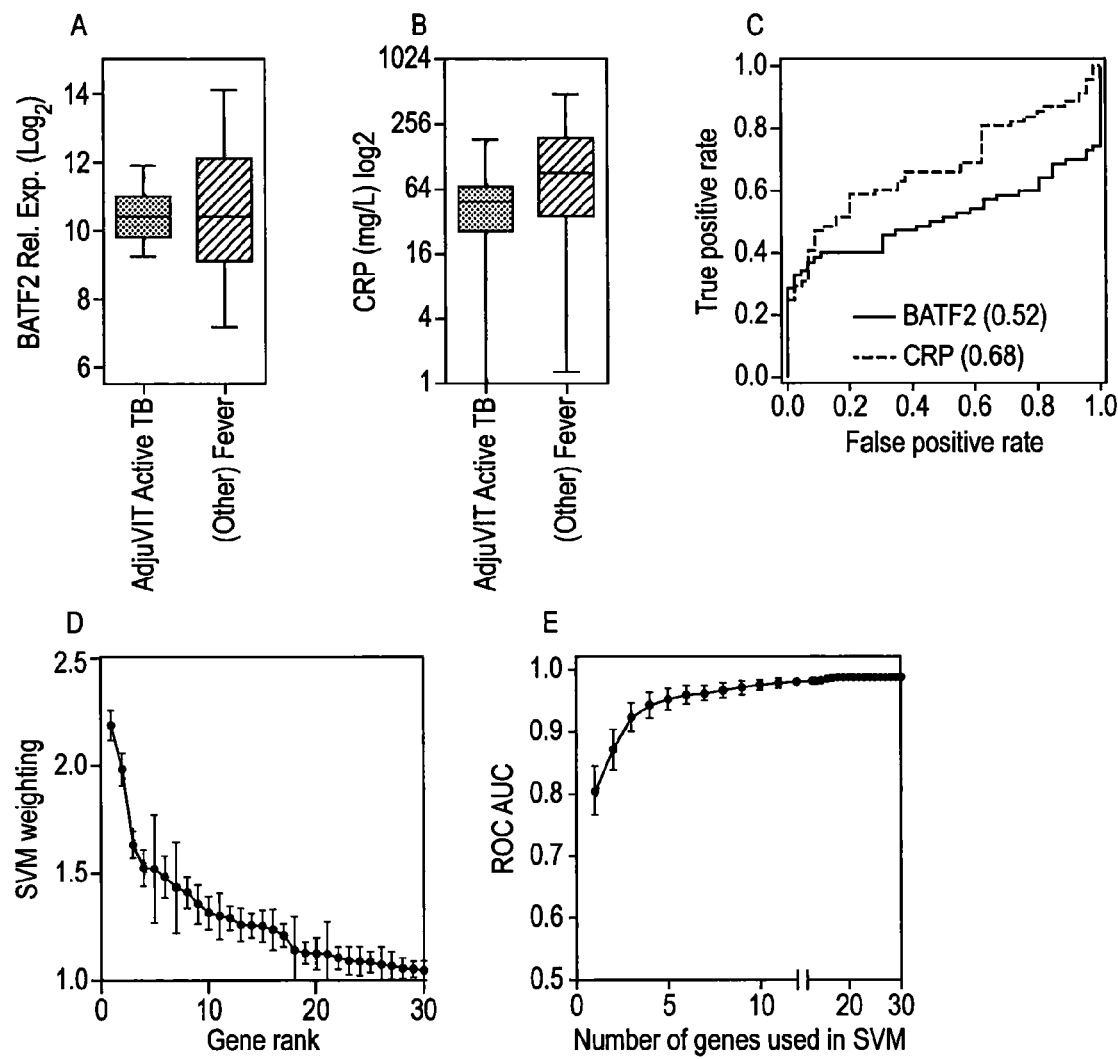
FIG. 4—Transcriptomic classification of active TB and other Fever cohort cases using SVM to identify most discriminating features. (A) Relative BATF2 gene expression and (B) serum C-reactive protein (CRP) levels in blood samples from patients with active TB in AdjuVIT cohort compared to patients with a spectrum of other infectious diseases presenting to hospital with fever. (C) ROC analyses for discrimination of active TB from other Fever cases using either blood levels of BATF2 gene expression or serum CRP only. ROC AUC are shown in brackets for each test. (D) Rank order of weightings for each gene in the SVM training model of patients with active TB or other Fever. (E) ROC AUC of SVM classification of active TB or other Fever using a cumulative number of genes in rank order of weightings. In D-E, data points show (mean±95% confidence intervals) obtained from 100 iterations in which one half of the data set were randomly separated into training and test sets for the SVM.
Figure 7:
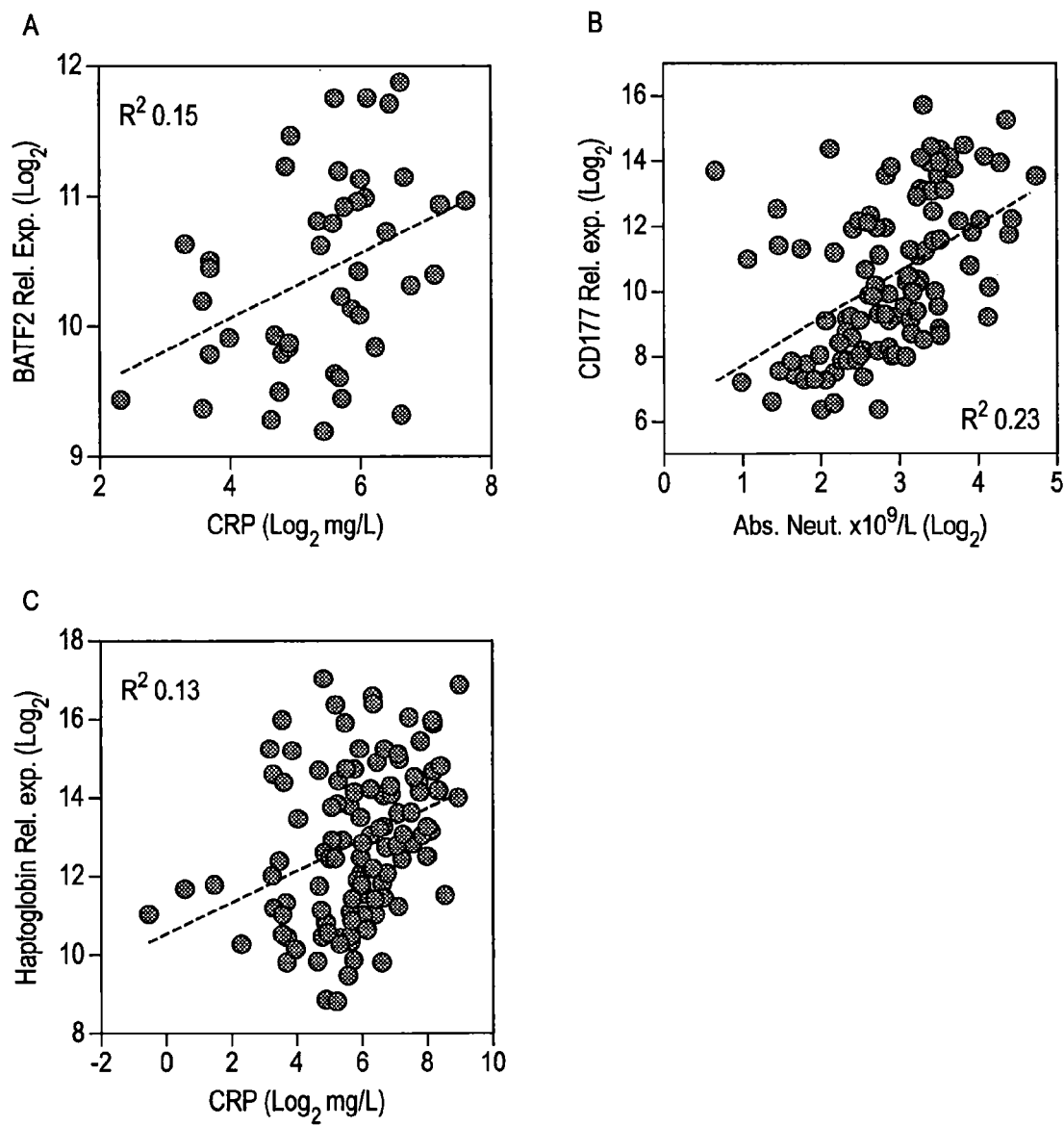
FIG. 7—Scatter plots of blood (A) BATF2 and serum CRP in patients with active TB (AdjuVIT cohort), (B) CD177 and blood neutrophil counts, and (C) blood haptoglobin transcripts and serum CRP concentrations in AdjuVIT active TB and Fever cohorts.

Example 4: Support Vector Machine Classification of Active TB by Comparison with Other Febrile Illnesses We compared BATF2 expression levels in the blood transcriptomes of the AdjuVIT cohort active TB cases to those of patients presenting to hospital with febrile illnesses (Fever cohort), representing a diverse spectrum of non-TB infectious diseases (Table 2). BATF2 levels amongst Fever cohort samples showed a wide range that overlapped with those of active TB cases (FIG. 4A, C). Serum C-reactive protein (CRP) that is widely used as a biomarker for infection and was also not significantly different between the two groups (FIG. 4B, C). BATF2 and CRP levels amongst these patients showed a relatively poor correlation coefficient suggesting that the two parameters were not co-regulated (FIG. 7A).

TABLE 2

| Fever cohort case mix | | | |
|---|---|---|---|
| System | N (%) | Syndrome | N (%) |
| Urinary Tract | 23 (32.9) | Urinary tract infection | 10 (14.3) |
| | | Pyelonephritis | 12 (17.1) |
| | | Epididymo-orchitis | 1 (1.4) |
| Respiratory | 17 (24.3) | Pneumonia | 10 (14.3) |
| | | Pharyngitis | 5 (7.1) |
| | | Infective exacerbation of COPD | 1 (1.4) |
| | | LRTI without CXR changes | 1 (1.4) |
| Systemic | 8 (11.4) | Malaria: non-falciparum | 2 (2.9) |
| | | Unspecified viral infection | 2 (2.9) |
| | | Neutropenic sepsis | 1 (1.4) |
| | | Septicaemia | 1 (1.4) |
| | | Unspecified | 1 (1.4) |
| | | Varicella | 1 (1.4) |
| Gastrointestinal | 6 (8.6) | Diverticulitis | 2 (2.9) |
| | | Gastroenteritis | 2 (2.9) |
| | | Appendicitis | 1 (1.4) |
| | | Intra-abdominal collection | 1 (1.4) |
| Skin and Soft Tissue | 5 (7.1) | Cellulitis | 2 (2.9) |
| | | Surgical wound infection | 2 (2.9) |
| | | Abscess | 1 (1.4) |
| Hepatobiliary | 4 (5.7) | Cholangitis | 2 (2.9) |
| | | Cholecystitis | 1 (1.4) |
| | | Liver abscess | 1 (1.4) |
| Other | 4 (5.7) | Unknown aetiology | 3 (4.3) |
| | | Rheumatological | 1 (1.4) |
| Gynaecological | 1 (1.4) | Pelvic collection | 1 (1.4) |
| Cardiovascular | 1 (1.4) | Infective endocarditis | 1 (1.4) |
| Dental and Perioral | 1 (1.4) | Dental abscess | 1 (1.4) |

(COPD = chronic obstructive pulmonary disease, LRTI = lower respiratory tract infection, CXR = chest x-ray)

Figure 5:
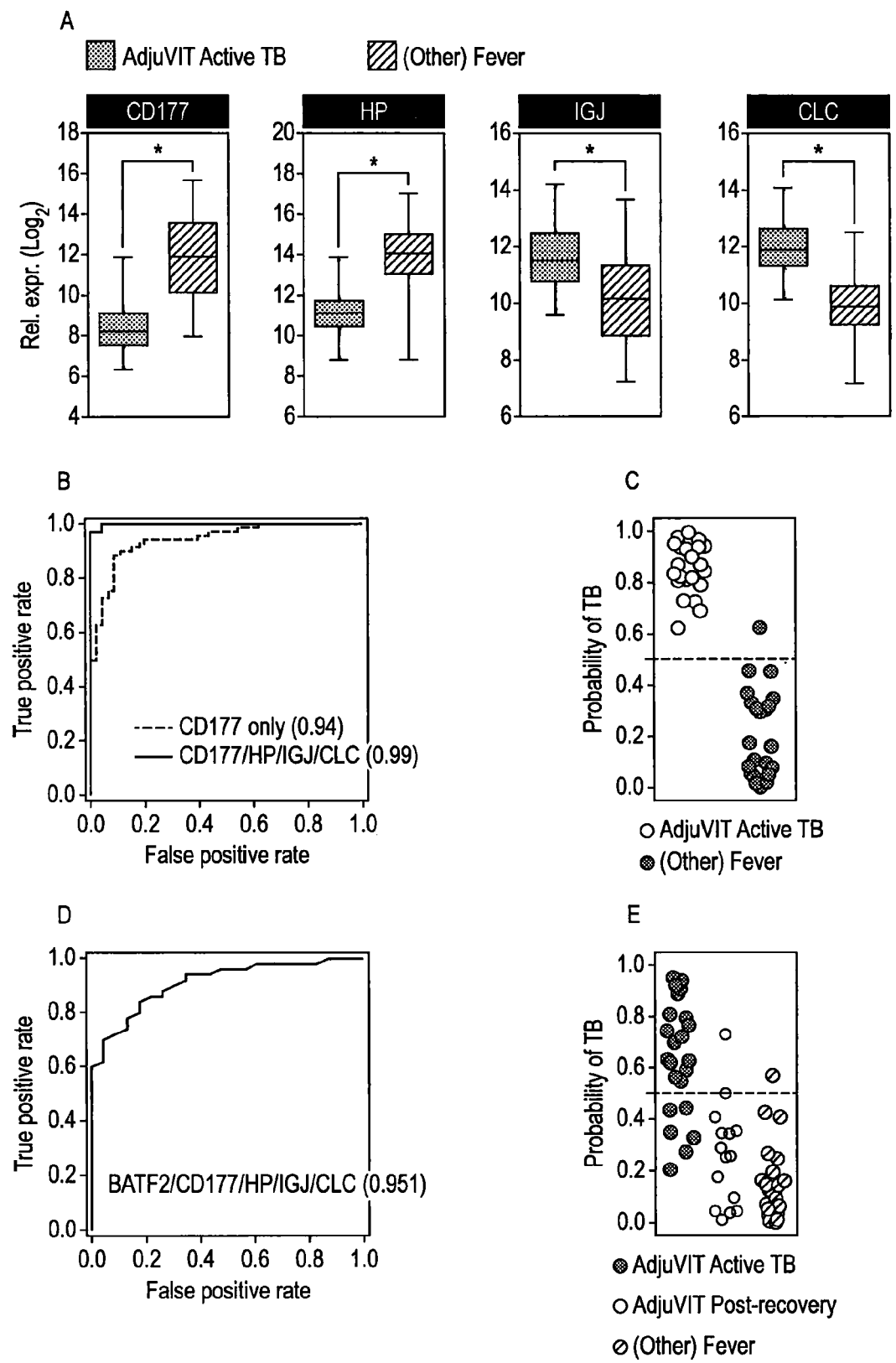
FIG. 5—Transcriptomic classification of active TB and other Fever cohort cases with four genes. (A) Relative expression of each of the genes indicated in peripheral blood of patients with active TB (AdjuVIT) and other Fever cohorts. (B) ROC analyses of SVM discrimination of active TB (AdjuVIT) from other Fever patients using expression levels of CD177 gene alone or all four of the genes indicated, by training one half of the data used to derive rank order of SVM weightings and then testing on the second half of the data. ROC AUC are shown in brackets for each test. (C) Transformation of the distance of each test case in (B) from the SVM separating hyperplane derived from the training half, using all four genes indicated, to give a case by case probability of TB. (D) ROC analyses of SVM discrimination of AdjuVIT active TB from AdjuVIT post-recovery and Fever cohort patients using expression levels of the genes indicated by training one half of the data used to derive rank order of SVM weightings and then testing on the second half of the data. ROC AUC are shown in brackets for each test. (E) Transformation of the distance of each test case in (D) from the SVM separating hyperplane derived from the training half, using all five genes indicated, to give a case by case probability of TB.

Next, we tested the hypothesis that alternative peripheral blood transcripts may differentiate active TB from other infections represented in the Fever cohort. We used half the combined AdjuVIT active TB and Fever cohort transcriptional data sets for SVM training on multiple random subsamples to identify their rank order of average weightings for discriminating active TB from Fever cases (FIG. 4D). Then we tested a cumulative number of genes in rank order of their weightings for their ability to discriminate between active TB and Fever cohort cases for their classification accuracy. We carried out 100 random train/test sequences in each case using half of the data for training and the other half for testing, and then calculated average ROC AUC scores. AUC scores increased from approximately 0.8 using the top-ranked gene alone, to 0.95 using the top four genes together, with only modest additional gains by the inclusion of further genes (FIG. 4E). Each of the four genes in this discriminating signature showed significantly different blood transcript levels in active TB compared to Fever cohort samples (FIG. 5A). CD177 and haptoglobin (HP) were expressed at higher levels in the Fever cohort samples, whereas Immunoglobulin J chain (IGJ) and galectin 10 (CLC) were expressed at higher levels in the active TB samples.

In order to validate their potential to discriminate between active TB and Fever cases, an SVM model was trained with transcriptional data for these four genes using all the first half of AdjuVIT active TB and Fever cohort cases, and tested on all the second half of the cases which had not been included in the identification of these genes (FIG. 5B). The four gene signature provided almost perfect classification of the test samples with a ROC AUC of 0.99. For comparison, we also tested the top-ranked gene, CD177, which discriminated between active TB and Fever cohort test cases with a ROC AUC of 0.94. CD177 is best characterised as surface glycoprotein expressed by subpopulations of neutrophils (Göhring et al., 2004; Stroncek et al., 1996; Matsuo et al., 2000), but the correlation coefficient with neutrophil counts in the AdjuVIT active TB and Fever cohort samples was only 0.23. This suggested that increased levels of CD177 in the Fever cohort samples are not simply a surrogate for increased frequency of circulating neutrophils, but may represent transcriptional upregulation of CD177 in these cases compared to active TB. We also noted that HP is recognised as an acute phase reactant and tested the correlation of HP transcript levels with levels of circulating CRP, but found very modest correlation between these two parameters also. These data suggested that increased levels of HP transcripts in non-TB infectious diseases cases reflected context specific transcriptional upregulation rather than a surrogate for non-specific acute phase responses.

Figure 8:
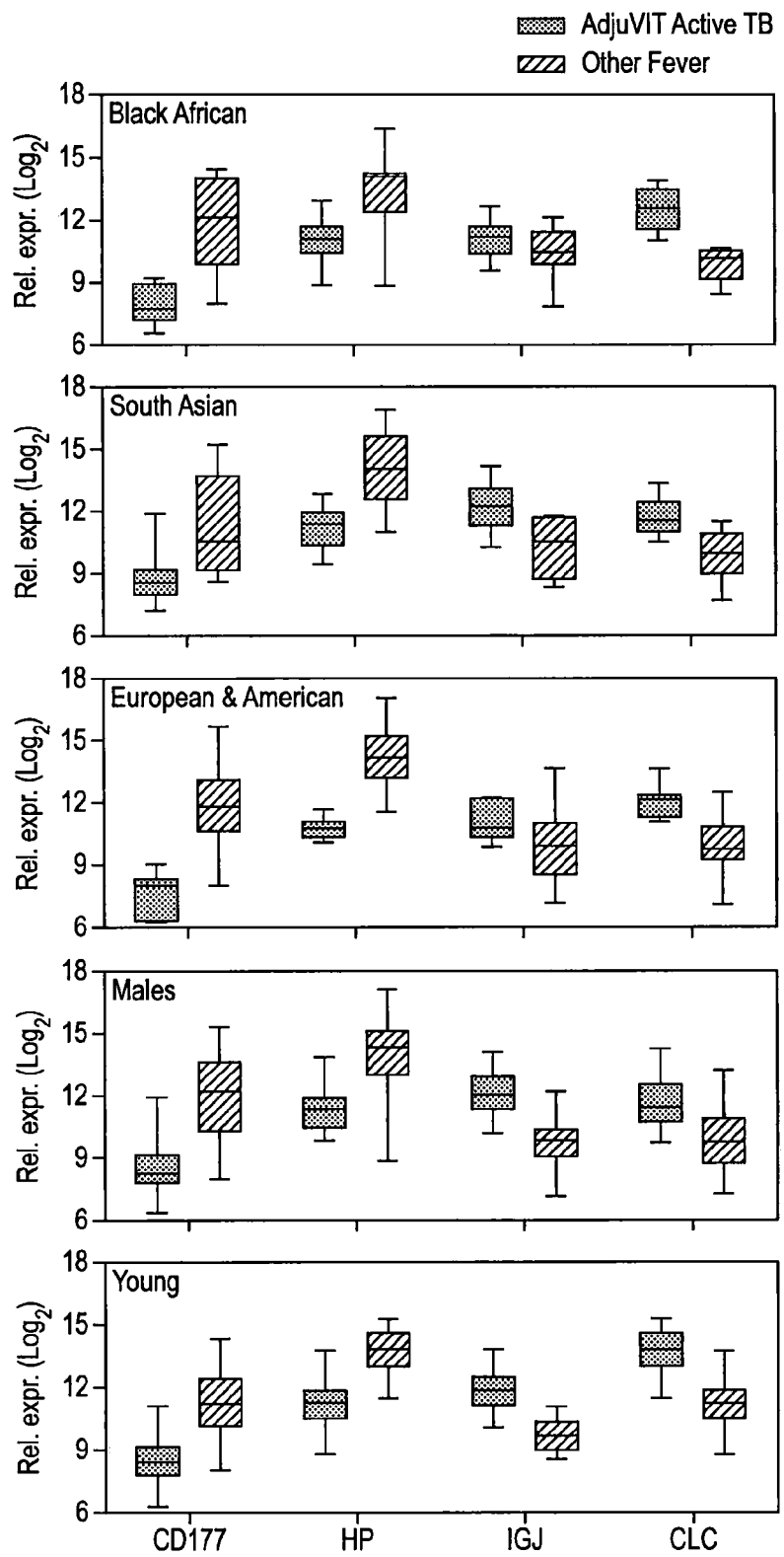
FIG. 8—Relative expression of each of the genes indicated in peripheral blood of patients of specific ethnicity, male gender or age <40 years, within AdjuVIT active TB and other Fever cohorts.
Figure 9:
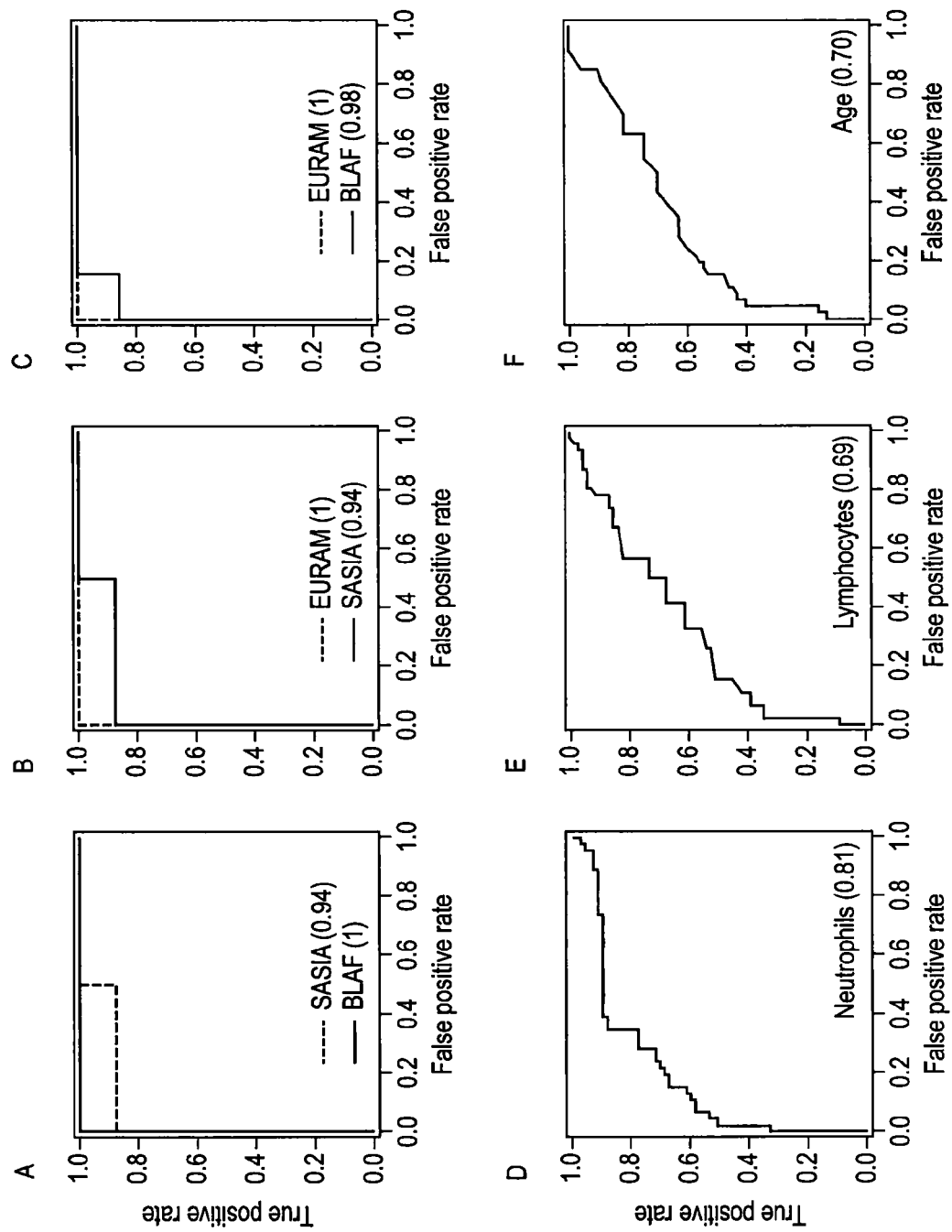
FIG. 9—(A-C) ROC analyses of SVM discrimination of active TB (AdjuVIT) from other Fever patients using expression levels of CD177, HP, IGJ and CLC in each of the ethnicities indicated, by training on (A) European and American (EURAM) patients, (B) Black African (BLAF) patients and (C) South Asian (SASIA) patients in each cohort. (D-F) ROC analyses for discrimination of active TB from other Fever cases using either blood (D) neutrophil, (E) lymphocyte counts, or (F) age. ROC AUC are shown in brackets for each test.

There were significant differences in ethnicity, age and gender between the AdjuVIT active TB and Fever cohort patients. However, the different patterns of gene expression that discriminate between the two cohorts were evident in all ethnic groups and not confounded by age or gender (FIG. 8). Moreover training the four gene signature SVM model using data from each ethnic group allowed accurate classification of cases in all other ethnic groups (FIG. 9A-C). In addition, significant differences in age and blood neutrophil or lymphocyte counts discriminated poorly between active TB and Fever cases (FIG. 9D-F).

Example 5: Derivation of a Single Risk Score for Test Cases

In order to achieve case-by-case confidence in the accuracy of the classification, we fitted the distance of each test case from the SVM separating hyperplane to a sigmoid logistic regression function to give a probability estimate between 0 and 1 (Platt et al., 1999), thereby generating a risk score for each of the test cases based on the SVM model derived from our four gene signature (FIG. 5C). Given that BATF2 can discriminate between active TB and healthy cases, and that an additional four genes can discriminate active TB from a wide range of other infectious diseases presenting with fever, we sought to combine the expression levels of BATF2 with CD177, HP, IGJ and CLC in a single SVM model to discriminate active TB from post-recovery cases in the AdjuVIT cohort, and from other diseases in the Fever cohort. The SVM model was trained using the five gene signature on one half of the AdjuVIT active TB cases in one group and one half of the AdjuVIT post-recovery TB cases pooled with one half of the Fever cohort cases in a second group. This model was then used to classify the remaining second half of the cases in all three groups providing a single risk score of active TB for each case and giving a ROC AUC of 0.95 (FIG. 5D-E).

Figure 6:
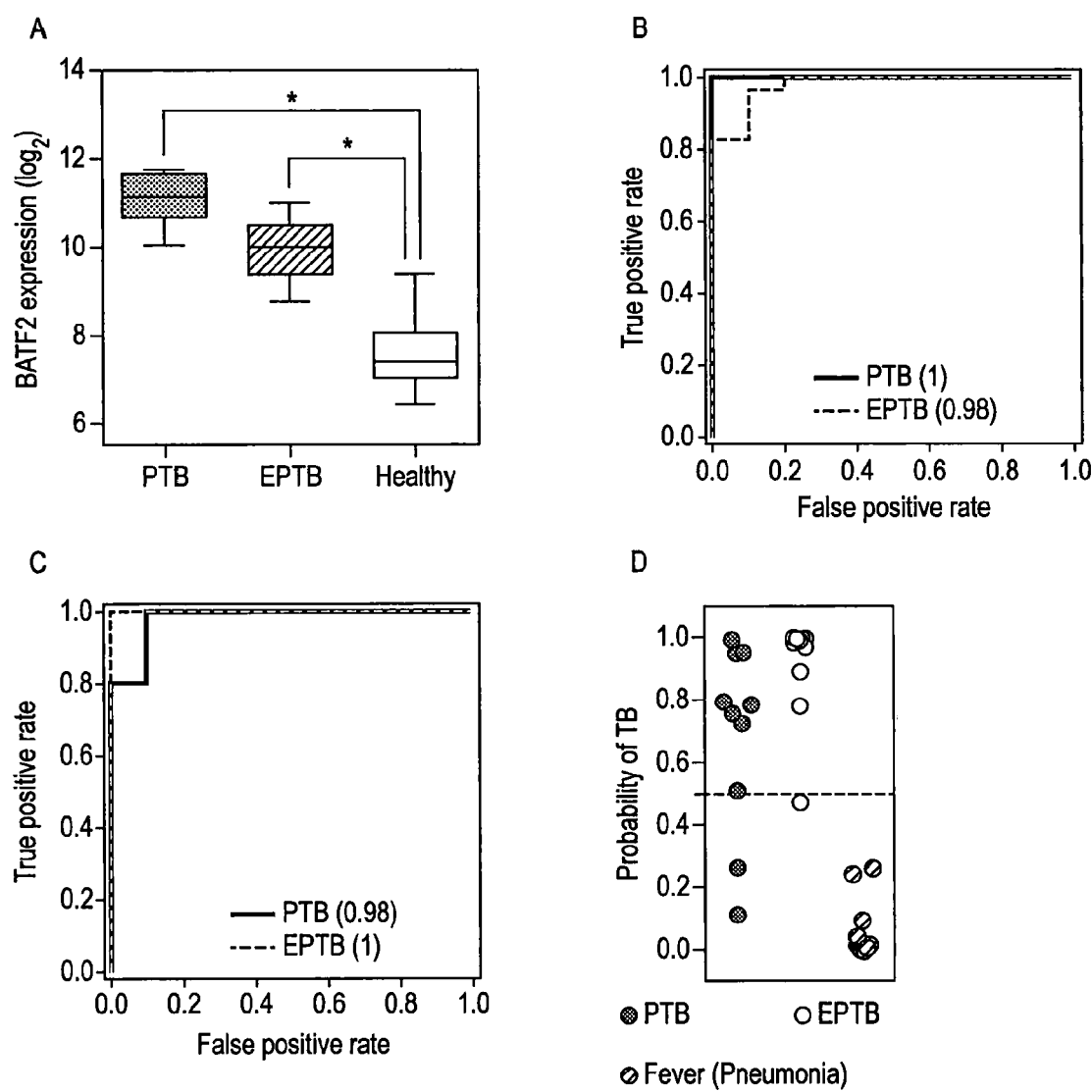
FIG. 6—Pulmonary and extrapulmonary TB discrimination from healthy cases and non-TB pneumonia. (A) Relative BATF2 gene expression in blood samples from a new independent cohort of patients with pulmonary TB (PTB), extrapulmonary TB (EPTB) or from healthy volunteers. (B) ROC analyses of SVM discrimination of PTB and ETB from healthy volunteers based on the BATF2 levels in (A). (C) ROC analyses of SVM discrimination of new PTB and ETB from new cohort of new non-TB pneumonia cases after training the SVM model on active TB (AdjuVIT) and other Fever cases using relative expression levels of CD177/HP/IGJ/CLC. (D) Transformation of the distance of each test case in (C) from the SVM separating hyperplane, using all four genes indicated, to give a case by case probability of TB.

Example 6: Blood Transcriptional Signatures for Active TB are Independent of the Site of Disease All the active TB cases in the AdjuVIT, Berry and Bloom cohorts were of pulmonary TB. Novel diagnostic biomarkers for TB are particularly needed for extrapulmonary TB in which existing microbiological diagnostics have the lowest sensitivity. Therefore, we obtained new blood transcriptomic data from additional cases to evaluate the utility of BATF2 and the four gene TB-specific transcriptional signature described above by comparison of healthy individuals, active pulmonary or extrapulmonary TB and non-TB pneumonia before any antibiotic treatment. By comparison with healthy volunteers, blood BATF2 transcript levels were significantly higher in both pulmonary and extrapulmonary TB cases (FIG. 6A). Elevated BATF2 classified cases of pulmonary TB with ROC AUC of 1 and extrapulmonary cases with ROC AUC of 0.98 (FIG. 6B). Finally, an SVM model trained with AdjuVIT active TB and all Fever cohort cases using the four gene TB specific signature of CD177, HP, IGJ and CLC, discriminated between new pulmonary or extrapulmonary TB cases and non-TB febrile pneumonia with ROC AUCs of 0.98 and 1 respectively (FIG. 6C-D). Therefore we concluded that BATF2 and the four gene TB blood transcriptional signatures performed equally well in classification of both pulmonary and extrapulmonary TB.

In brief summary, the above studies show that elevated blood transcript BATF2 levels discriminate active pulmonary and extrapulmonary TB disease from healthy states and that blood transcript levels of CD177, haptoglobin, immunoglobin J chain, and galectin 10 discriminate active pulmonary and extrapulmonary TB disease from other infectious diseases, summarised in Table 3.

TABLE 3

| Cohort name | Cases | Controls | Age group | HIV status | Study site | Genes | ROC AUC | Reference doi |
|---|---|---|---|---|---|---|---|---|
| Roe, 2016 | PTB | Treated TB | Adults | – | UK | BATF2 | 0.99 | 10.1172/jci.insight.87238DS1 |
| | PTB | LTBI | | | | | 0.98 | |
| | EPTB | HC | | | | | 0.96 | |
| | PTB | Fever | | | | CD177, | 0.99 | |
| | PTB | Pneumonia | | | | RP, IGJ, | 0.99 | |
| | EPTB | Pneumonia | | | | CLC | 1.0 | |

TABLE 3-continued

| Cohort name | Cases | Controls | Age group | HIV status | Study site | Genes | ROC AUC | Reference doi |
|---|---|---|---|---|---|---|---|---|
| Kaforou, 2013 | PTB & EPTB | LTBI | Adults | − | SA | BATF2 | 0.93 | 10.1371/journal.pmed.1001538 |
|  | PTB & EPTB | LTBI |  | + |  |  | 0.85 |  |
| Bloom, 2012 | PTB | LTBI | Adults | − | UK & SA | BATF2 | 0.99 | 10.1371/journal.pone.0046191 |
| Berry, 2010 | PTB | HC | Adults | − | UK & SA | BATF2 | 0.96 | 10.1038/nature09247 |

PTB = Pulmonary TB,
EPTB = Extrapulmonary TB,
LTBI = Latent TB infection,
HC = healthy controls,
UK = United Kingdom,
SA = Southern Africa,
USA = United States of America,
Numbers in brackets = Number of subjects in each group,
ROC AUC = receiver operation characteristic area under the curve.

Example 7: Extended Validation of Biomarkers for Active Tuberculosis

This Example is an extended validation of the use of blood BATF2 transcript levels to discriminate active tuberculosis (TB) from latent TB infection and healthy controls. These include data in children and individuals with and without HIV co-infection.

We show that significantly elevated levels of BATF2 are evident up to 3 months before the onset of active TB and reduce after 8 weeks of TB treatment. Hence BATF2 transcript levels may be used to predict onset of active TB within 3 months and predict successful treatment by 2 months of therapy.

Changes in transcriptional levels of BATF2 are detectable at the protein level, indicating that quantitative BATF2 protein assays may be used as an alternative to transcriptional assays.

In addition, we have undertaken extended validation of the use of blood CD177, haptoglobin, immunoglobin J chain, and galectin 10 to discriminate active from other non-TB infectious diseases, including patients with and without HIV co infection.

Experimental Methods

Patient Samples

The data presented was derived from previously published genome-wide transcriptional profiling data sets and RNA sequencing of samples from new patient cohorts (Table 4).

Gene Expression Analysis in Clinical Samples

All raw gene expression data was normalised as described above, before extracting expression data from the target genes. Expression of BATF2 was used to distinguish cases of active TB from healthy and expression of CD177, haptoglobin, immunoglobulin J chain, and galectin 10 was used as a four gene signature to discriminate active TB from pneumonia. In the latter, a support vector machine model derived from previously published cases of active TB and diverse infectious diseases presenting to hospital with fever, was used to classify novel cases of active TB and non-TB pneumonia as described in Roe et al., 2016.

TABLE 4

| Cohort name | Cases | Controls | Age group | HIV status | Study site | Genes | ROC AUC | Reference doi |
|---|---|---|---|---|---|---|---|---|
| Roe | PTB (11) | Non-TB (10) Pneumonia (10) | Adults | +/− | UK&SA | BATF2<br>CD177, RP, IGJ, CLC | 0.9<br>1.0 | N/A |
| Roe | PTB (46) | Treated PTB after 2 (46), 8 (44) & 52 (31) weeks | Adults | − | UK | BATF2 | N/A | N/A |
| Blankley | PTB (45)<br>EPTB (47) | HC (61) | Adults | − | UK | BATF2 | 0.99<br>0.96 | 10.1371/journal.pone.0162220 |
| Zak 2016 | PTB & EPTB at <3 m (12), 3-12 m (29) & >12 m (22) before TB diagnosis | HC (166) | Adults | − | SA | BATF2 | N/A | 10.1016/S0140-6736(15)01316-1 |
| Walter 2016 | PTB (35) | LTBI (35) | Adults | − | USA | BATF2 | 0.91 | 10.1128/JCM.01990-15 |
| Anderson 2014 | PTB (51)<br>PTB (95) | LTBI (68) | Children | −<br>+ | SA | BATF2 | 0.87<br>0.92 | 10.1056/NEJMoa1303657 |

TABLE 4-continued

| Cohort name | Cases | Controls | Age group | HIV status | Study site | Genes | ROC AUC | Reference doi |
|---|---|---|---|---|---|---|---|---|
| Bloom 2013 | PTB (35) | HC (113) | Adults | – | UK | BATF2 | 0.99 | 10.1371/journal.pone.0070630 |
| Bloom 2012 | PTB (29) | Treated PTB after 2 (25), 8 (24) & 52 (29) weeks | Adults | – | UK & SA | BATF2 | N/A | 10.1371/journal.pone.0046191 |

PTB = Pulmonary TB,
EPTB = Extrapulmonary TB,
LTBI = Latent TB infection,
HC = healthy controls.
UK = United Kingdom,
SA = Southern Africa,
USA = United States of America,
Numbers in brackets = Number of subjects in each group,
ROC AUC = receiver operation characteristic area under the curve.

BATF2 Transcript and Protein Measurements in Thp1 Cells

Thp1 cells were incubated ±IFNβ or IFNγ at 10 ng/mL for 24 hours before collecting cell lysates for RNA and protein extractions as previously described (Noursadeghi et al., 2009; Tomlinson et al., 2013). RNA was then subjected to genome-wide transcriptional profiling as previously described (Noursadeghi et al., 2009; Tomlinson et al., 2013), and the cellular proteins were subjected to western blotting for β actin (AC-15, abcam) and BATF2 (EPR10667, abcam) as previously described (Noursadeghi et al., 2009; Tomlinson et al., 2013). Immunoreactive bands were quantified with the Odyssey imaging system (LI-COR). Relative BATF2 protein expression was normalised to expression of β actin.

Example 7a: Extended Validation of BATF2, CD177, Haptoglobin, Immunoglobin J Chain, and Galectin 10 Transcript Levels to Discriminate Individuals with Active TB from Healthy Controls Patients with Latent TB Infection (LTBI) and Other Infectious Diseases In data derived from two previously published studies (Bloom et al., 2013; Blankley et al., 2014), blood BATF2 transcript levels at the time of diagnosis in adult patients with active pulmonary and extrapulmonary TB were significantly greater than those of healthy controls. In receiver operating characteristic curve (ROC) analysis BATF2 transcript levels accurately discriminated between active TB cases and healthy controls with area under the curve (AUC) of 0.96 0.99 (FIG. 10A-D).

Figure 10:
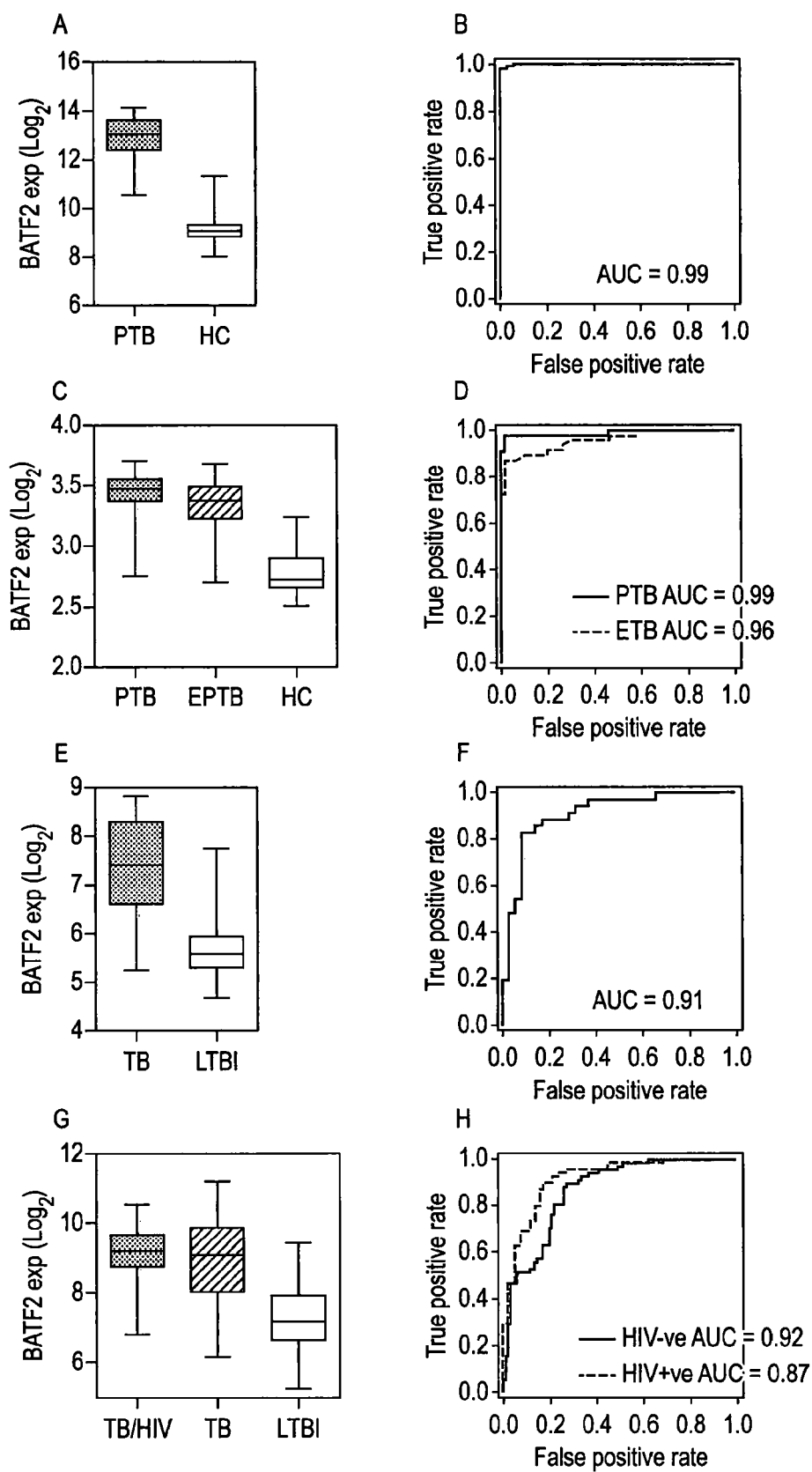
FIG. 10—Relative blood BATF2 transcript levels derived from genome-wide transcriptional profiles from whole blood (left hand panels) and receiver operating characteristic curve (ROC) analysis using BATF2 levels (right hand panels) to discriminate between, (A-B) adults with active pulmonary TB (PTB) and healthy controls (HC) (doi:10.1371/journal.pone.0070630), (C-D) adults with active PTB and active extrapulmonary TB (EPTB) and HC (doi:10.1371/journal.pone.0162220), (E-F) adults with active TB and latent TB infection (LTBI) (doi:10.1128/JCM.01990-15.) and (G-H) children with active TB with and without HIV coinfection, or LTBI. AUC=area under the curve for each ROC analysis.

In data derived from another published study in adults (Walter et al., 2015), blood BATF2 transcript levels at the time of diagnosis in adult patients with active pulmonary TB were significantly greater than those of adults with LTBI, and discriminated between active TB and LTBI with ROC AUC of 0.91 (FIG. 10E-F). Likewise, in a previously published study in children (Anderson et al., 2014), blood BATF2 transcript levels at the time of diagnosis of active pulmonary TB was significantly higher in both HIV positive and HIV negative children compared to those of children with LTBI. In these data blood BATF2 transcript levels discriminated between active TB and LTBI with ROC AUC of 0.87 0.92 (FIG. 10G-H).

Figure 11:
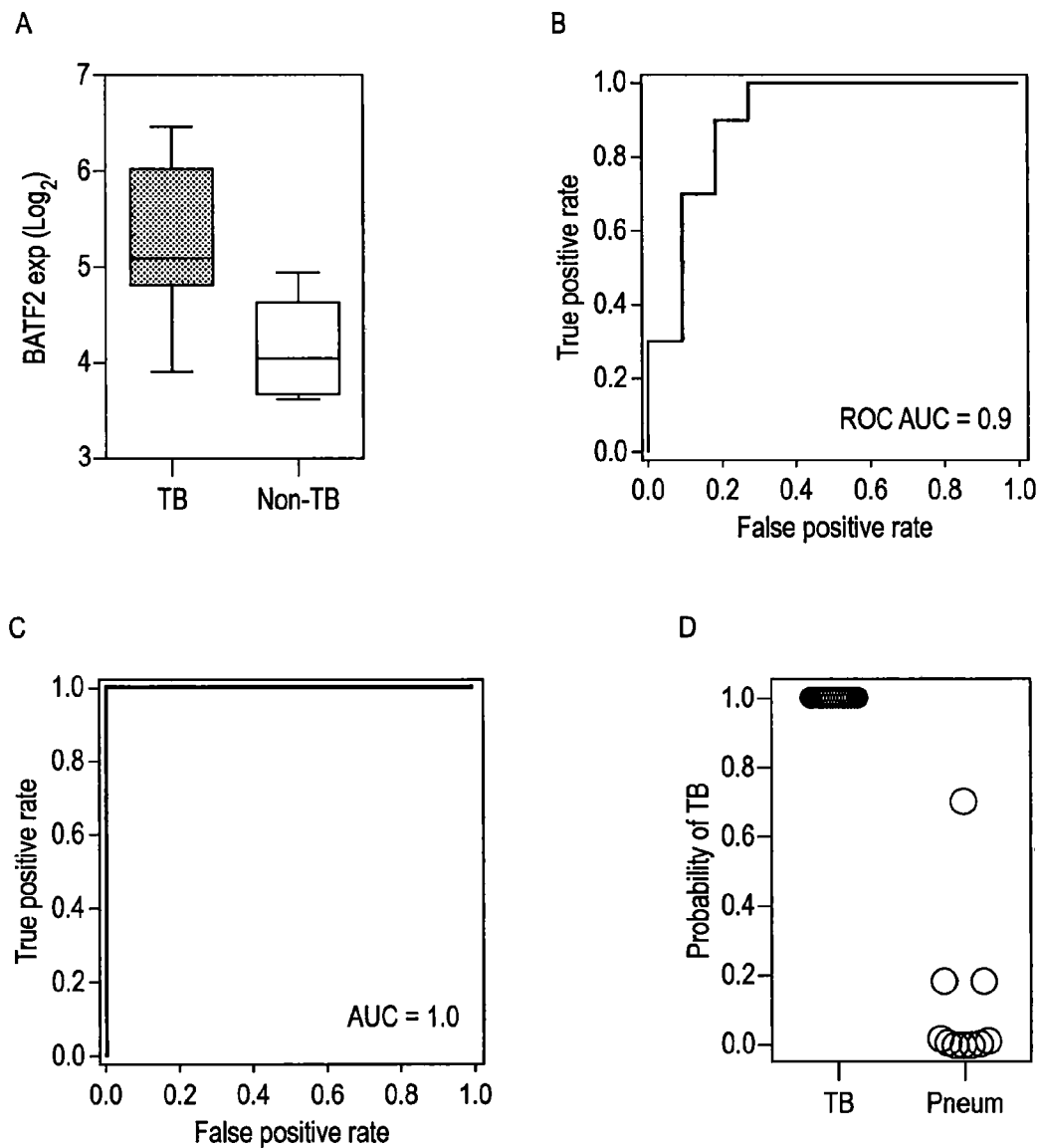
FIG. 11—(A) Relative blood BATF2 transcript levels derived from genome-wide transcriptional profiles from whole blood and (B) receiver operating characteristic curve (ROC) analysis using BATF2 levels to discriminate between adults with and without active TB in a previously unpublished South African cohort, all of whom are being investigated for active TB. (C) ROC analysis to discriminate active TB in the patients from the cohort above from patients presenting to hospital with non-TB pneumonia (AUC=area under the curve) with a support vector machine model used blood transcript levels of CD177, haptoglobin, immunoglobin J chain, and galectin 10. (D) Case specific probability of TB using a logistic regression function to plot the distance from the discriminating hyperplane within the SVM model in C.

In new (unpublished) data from adult HIV positive and HIV negative patients being investigated for active TB, blood BATF2 levels at the time of investigation were compared in patients with and without evidence of active TB on the basis of existing microbiological diagnoses and clinical criteria. Blood BATF2 transcript levels were significantly higher in patients with active TB compare to those who did not prove to have active TB, and discriminated between these groups with ROC AUC of 0.9 (FIG. 11A-B).

We have already shown that active TB can be differentiated using a support vector machine (SVM) learning model based on levels of CD177, haptoglobin, immunoglobin J chain, and galectin 10. To further validate our previous observations we tested the performance of this SVM model in discrimination of the new adult HIV positive and HIV negative patients, described above, from another new cohort of adult patients with non-TB lower respiratory tract infections (pneumonia). This four gene signature discriminated between active TB and pneumonia with ROC AUC of 1 (FIG. 11C-D).

Taken together, these data provide a new analysis of data derived from 626 patients in total. Importantly, our extended validation includes data from pulmonary and extrapulmonary TB, children as well as adults and patients with and without HIV co infection.

Figure 12:
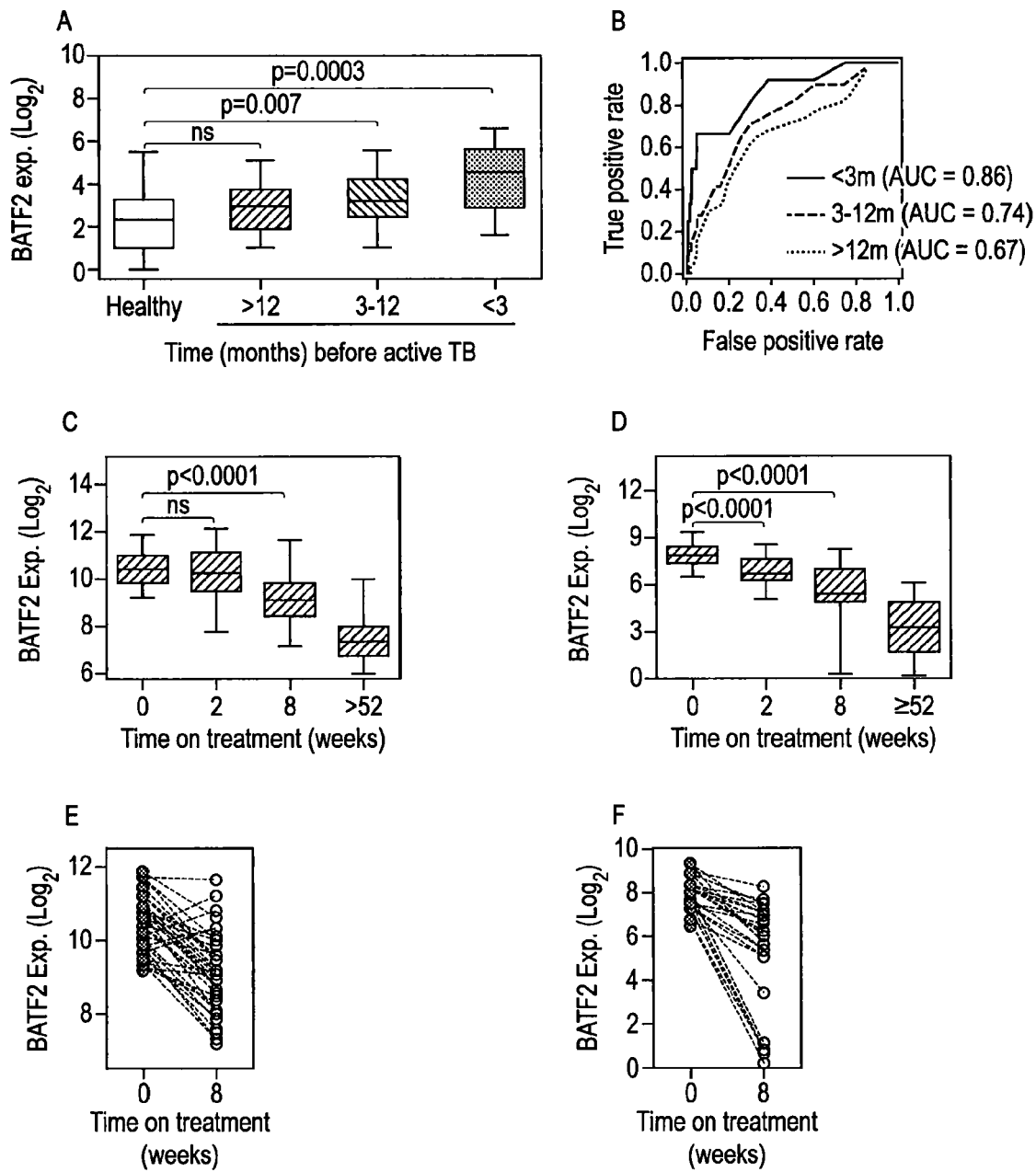
FIG. 12—(A) Relative blood BATF2 transcript levels derived from genome-wide transcriptional profiles from whole blood in Healthy control and patients who develop active TB>12 months, 2=3-12 months or <3 months after blood sampling. (B) Receiver operating characteristic curve (ROC) analysis using BATF2 levels to discriminate between healthy controls and cases which develop active TB in each of the time intervals indicated in A. (AUC=area under the curve). (C-D) Relative blood BATF2 transcript levels derived from genome-wide transcriptional profiles from whole blood of patients with active TB at different time points after initiation of TB treatment. P values indicated are derived from Mann-Whitney tests. (E-F) Paired blood BATF2 transcript levels where available from individual patients sampled at 0 and 8 weeks of TB treatment. Data in C and E are derived from doi: 10.1016/S0140-6736(10) 61889-2, and data in D and F are derived from doi: 0.1371/journal.pone.0046191.

Example 7b: Elevated Blood BATF2 Transcript Levels can Predict Active TB 3 Months Before the Onset of Disease Zak et al., 2016 show that blood transcripts may change before the onset of active TB. Therefore, we tested the hypothesis in these data that blood BATF2 transcript levels specifically, become elevated before the onset of active TB. In a longitudinal cohort of patients sampled over 2 years, we compared blood BATF2 transcript levels in at various time points before the onset of active TB disease in a proportion who developed active TB, with all measurements made in individuals who remained healthy. A significant increase in blood BATF2 transcript levels was evident in samples obtained at 3-12 months before the diagnosis of active TB and a further significant increase was evident in samples obtained within 3 months of presentation with active TB (FIG. 12A). Elevated blood BATF2 transcript levels discriminated patients who developed active TB within 3 months from those who remained healthy with ROC AUC of 0.83 (FIG. 12B).

Example 7c: Reduced Blood BATF2 Transcript Levels after 8 Weeks Treatment of Active TB TB treatment leads to a reduction in blood BATF2 transcript levels (Roe et al., 2016). We have now extended this analysis to investigate the earliest time point at which we can detect a fall in blood BATF2 transcript levels. We identified data from two cohorts of patients with drug sensitive active TB, which combined longitudinal blood sampling and follow up beyond 6 months TB treatment with no early recurrence of active disease suggestive of therapeutic failure (Bloom et al., 2012; Martineau et al., 2011). By comparison to pretreatment levels, blood BATF2 transcript levels reduced significantly in both studies by 8 weeks of TB treatment. In patients from these studies for whom paired data from pretreatment and 8 week blood samples were available, 95% showed a fall in their blood BATF2 transcript levels (FIG. 12E-F). These data suggest that blood BATF2 transcript levels can be used as a surrogate biomarker of response to treatment at 8 weeks of treatment. This is particularly important because no drug susceptibility data is available in approximately 50% of patients started on TB treatment. In this context our data suggest that the fall in BATF2 transcript levels can be used as evidence for therapeutic responses to empirical drug treatment.

Figure 13:
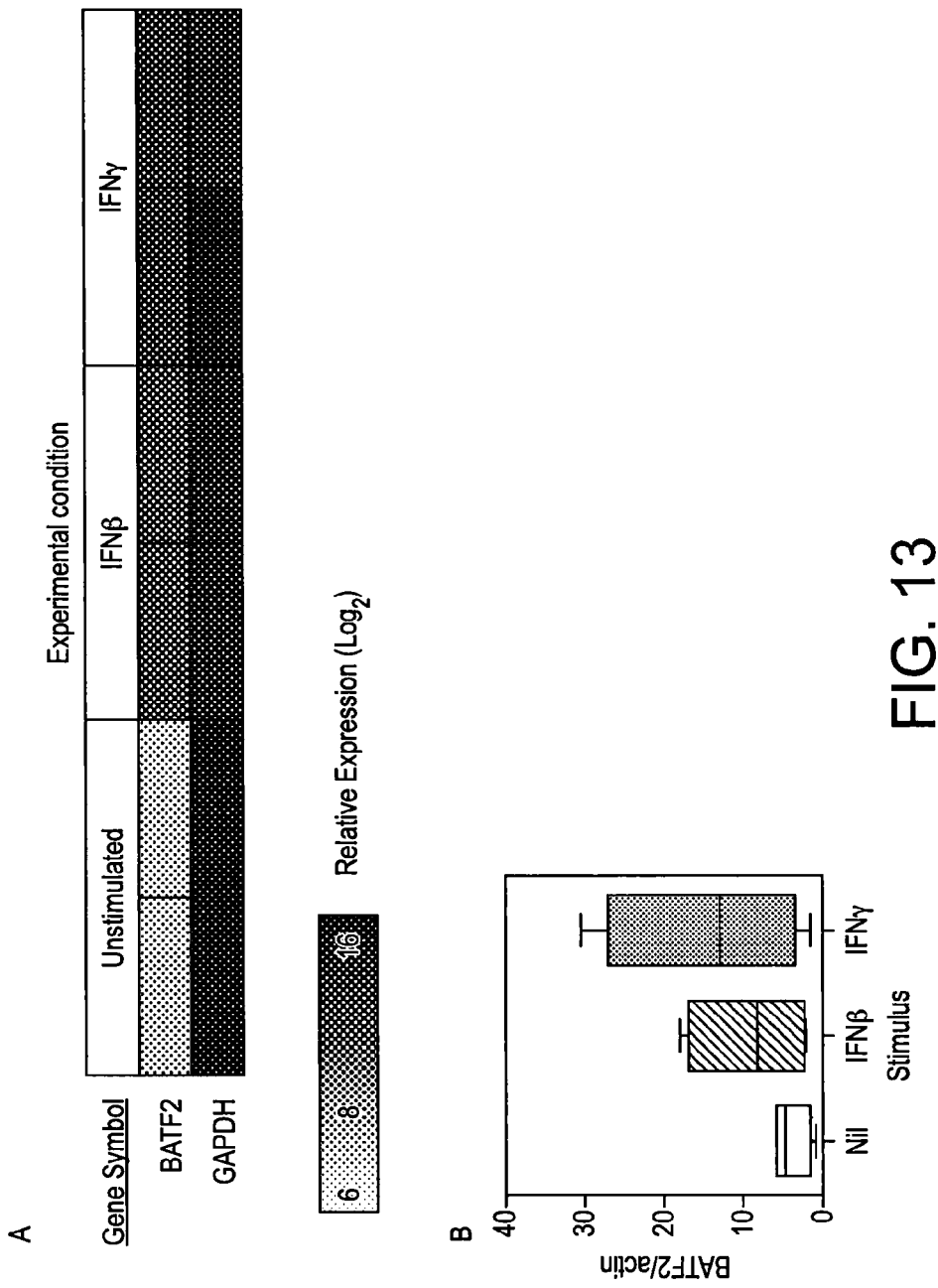
FIG. 13—(A) Relative expression of BATF2 and GAPDH in duplicate Thp1 cells ±interferon (IFN)β or IFNγ stimulation for 24 hours measured by gene expression arrays. (B) Relative BATF2:β-actin immunostaining in western blot analysis of Thp1 cells ±IFNβ or IFNγ stimulation for 24 hours (N=4).

Example 7d: Elevated BATF2 Transcript Levels are Associated with Increased Levels of BATF2 Protein BATF2 exhibits interferon (IFN) inducible transcription in mononuclear phagocytic cells (Murphy et al., 2013). Systemic IFN activity is widely recognised in active TB (Berry et al., 2010). We sought to test the hypothesis that IFN inducible upregulation of BATF2 in Thp1 mononuclear phagocytic cells was associated with increased expression at the protein level. We first confirmed that IFN stimulation of Thp1 cells induced transcriptional upregulation of BATF2 in Thp1 cells (FIG. 13A), and subsequently that we could also detect IFN inducible increase in BATF2 protein levels in these cells by quantitative Western blot analysis (FIG. 13B). These data suggest that increased levels of blood BATF2 transcripts in active TB may also be associated with increased BATF2 protein levels in blood cells.

```
SEQUENCES
(IGJ mRNA Homo sapiens)
                                                                SEQ ID NO: 1
    1 ttgtgattgt ttttagtttg ttagctgcct ggagtgttat tttaagaaag cagaagcacc 61 atcatttgca cactccttat agatcacaca ccttaacccct gactttttttt gctccagttt 121 ttcagaagaa gtgaagtcaa gatgaagaac catttgcttt tctggggagt cctggcggtt 181 tttattaagg ctgttcatgt gaaagcccaa gaagatgaaa ggattgttct tgttgacaac 241 aaatgtaagt gtgcccggat tacttccagg atcatccgtt cttccgaaga tcctaatgag 301 gacattgtgg agagaaacat ccgaattatt gttcctctga acaacaggga gaatatctct 361 gatcccacct caccattgag aaccagattt gtgtaccatt tgtctgacct ctgtaaaaaa 421 tgtgatccta cagaagtgga gctggataat cagatagtta ctgctaccca gagcaatatc 481 tgtgatgaag acagtgctac agagacctgc tacacttatg acagaaacaa gtgctacaca 541 gctgtggtcc cactcgtata tggtggtgag accaaaatgg tggaaacagc cttaacccca 601 gatgcctgct atcctgacta atttaagtca ttgctgactg catagctctt tttcttgaga 661 ggctctccat tttgattcag aaagttagca tatttattac caatgaattt gaaaccaggg 721 cttttttttt tttttgggtg atgtaaaacc aactccctgc caccaaaata attaaaatag 781 tcacattgtt atctttatta ggtaatcact tcttaattat atgttcatac tctaagtatc 841 aaaatcttcc aattatcatg ctcacctgaa agaggtatgc tctcttagga atacagtttc 901 tagcattaaa caaataaaca aggggagaaa ataaaactca aggactgaaa atcaggaggt 961 gtaataaaat gttcctcgca ttcccccccg ctttttttttt tttttttgac tttgccttgg 1021 agagccagag cttccgcatt ttctttacta ttctttttaa aaaaagtttc actgtgtaga 1081 gaacatatat gcataaacat aggtcaatta tatgtctcca ttagaaaaat aataattgga 1141 aaacatgttc tagaactagt tacaaaaata atttaaggtg aaatctctaa tatttataaa 1201 agtagcaaaa taaatgcata attaaaatat atttggacat aacagacttg gaagcagatg 1261 atacagactt cttttttttca taatcaggtt agtgtaagaa attgccattt gaaacaatcc 1321 attttgtaac tgaaccttat gaaatatatg tatttcatgg tacgtattct ctagcacagt 1381 ctgagcaatt aaatagattc ataagcataa aaa (HP mRNA Homo sapiens, transcript variant 1)
                                                                SEQ ID NO: 2
    1 agcataaaaa gaccagcaga tgccccacag cactgctctt ccagaggcaa gaccaaccaa 61 gatgagtgcc ctgggagctg tcattgccct cctgctctgg ggacagcttt ttgcagtgga
```

-continued

```
121  ctcaggcaat gatgtcacgg atatcgcaga tgacggctgc ccgaagcccc ccgagattgc
181  acatggctat gtggagcact cggttcgcta ccagtgtaag aactactaca aactgcgcac
241  agaaggagat ggagtataca ccttaaatga taagaagcag tggataaata aggctgttgg
301  agataaactt cctgaatgtg aagcagatga cggctgcccg aagcccccg agattgcaca
361  tggctatgtg gagcactcgg ttcgctacca gtgtaagaac tactacaaac tgcgcacaga
421  aggagatgga gtgtacacct aaacaatga gaagcagtgg ataaataagg ctgttggaga
481  taaacttcct gaatgtgaag cagtatgtgg gaagcccaag aatccggcaa acccagtgca
541  gcggatcctg ggtggacacc tggatgccaa aggcagcttt ccctggcagg ctaagatggt
601  ttcccaccat aatctcacca caggtgccac gctgatcaat gaacaatggc tgctgaccac
661  ggctaaaaat ctcttcctga accattcaga aaatgcaaca gcgaaagaca ttgcccctac
721  tttaacactc tatgtgggga aaagcagct tgtagagatt gagaaggttg ttctacaccc
781  taactactcc caggtagata ttgggctcat caaactcaaa cagaaggtgt ctgttaatga
841  gagagtgatg cccatctgcc taccttcaaa ggattatgca gaagtagggc gtgtgggtta
901  tgtttctggc tgggggcgaa atgccaattt taaatttact gaccatctga agtatgtcat
961  gctgcctgtg gctgaccaag accaatgcat aaggcattat gaaggcagca cagtccccga
1021 aaagaagaca ccgaagagcc tgtaggggt gcagcccata ctgaatgaac acacttctg
1081 tgctggcatg tctaagtacc aagaagacac ctgctatggc gatgcgggca gtgcctttgc
1141 cgttcacgac ctggaggagg acacctggta tgcgactggg atcttaagct ttgataagag
1201 ctgtgctgtg gctgagtatg gtgtgtatgt gaaggtgact tccatccagg actgggttca
1261 gaagaccata gctgagaact aatgcaaggc tggccggaag cccttgcctg aaagcaagat
1321 ttcagcctgg aagagggcaa agtggacggg agtggacagg agtggatgcg ataagatgtg
1381 gtttgaagct gatgggtgcc agccctgcat tgctgagtca atcaataaag agctttcttt
1441 tgacccataa aaaaaaaaaa aaaaaaaaaa aaaaaaaa
```

(HP mRNA *Homo sapiens*, transcript variant 2)

SEQ ID NO: 3

```
  1  agcataaaaa gaccagcaga tgccccacag cactgctctt ccagaggcaa gaccaaccaa
 61  gatgagtgcc ctgggagctg tcattgccct cctgctctgg ggacagcttt tgcagtggaa
121  ctcaggcaat gatgtcacgg atatcgcaga tgacggctgc ccgaagcccc ccgagattgc
181  acatggctat gtggagcact cggttcgcta ccagtgtaag aactactaca aactgcgcac
241  agaaggagat ggagtgtaca ccttaaacaa tgagaagcag tggataaata aggctgttgg
301  agataaactt cctgaatgtg aagcagtatg tgggaagccc aagaatccgg caaacccagt
361  gcagcggatc ctgggtggac acctggatgc caaaggcagc tttccctggc aggctaagat
421  ggtttcccac cataatctca ccacaggtgc cacgctgatc aatgaacaat ggctgctgac
481  cacggctaaa aatctcttcc tgaaccattc agaaaatgca acagcgaaag acattgcccc
541  tactttaaca ctctatgtgg ggaaaaagca gcttgtagag attgagaagg ttgttctaca
601  ccctaactac tcccaggtag atattgggct catcaaactc aaacagaagg tgtctgttaa
661  tgagagagtg atgcccatct gcctaccttc aaaggattat gcagaagtag ggcgtgtggg
721  ttatgtttct ggctgggggc gaaatgccaa ttttaaattt actgaccatc tgaagtatgt
781  catgctgcct gtggctgacc aagaccaatg cataaggcat tatgaaggca gcacagtccc
841  cgaaaagaag acaccgaaga gccctgtagg ggtgcagccc atactgaatg aacacacctt
901  ctgtgctggc atgtctaagt accaagaaga cacctgctat ggcgatgcgg gcagtgcctt
```

```
 961 tgccgttcac gacctggagg aggacacctg gtatgcgact gggatcttaa gctttgataa
1021 gagctgtgct gtggctgagt atggtgtgta tgtgaaggtg acttccatcc aggactgggt
1081 tcagaagacc atagctgaga actaatgcaa ggctggccgg aagcccttgc ctgaaagcaa
1141 gatttcagcc tggaagaggg caaagtggac gggagtggac aggagtggat gcgataagat
1201 gtggtttgaa gctgatgggt gccagccctg cattgctgag tcaatcaata aagagctttc
1261 ttttgaccca taaaaaaaaa aaaaaaaaaa aaaaaaaaa a
```

(HP mRNA *Homo sapiens*, transcript variant 3)

SEQ ID NO: 4

```
   1 agcataaaaa gaccagcaga tgccccacag cactgctctt ccagaggcaa gaccaaccaa
  61 gatgagtgcc ctgggagctg tcattgccct cctgctctgg gacagctttt tgcagtgga
 121 ctcaggcaat gatgtcacgg atatcgcaga tgacggctgc ccgaagcccc ccgagattgc
 181 acatggctat gtggagcact cggttcgcta ccagtgtaag aactactaca aactgcgcac
 241 agaaggagat ggagtataca ccttaaatga taagaagcag tggataaata aggctgttgg
 301 agataaactt cctgaatgtg aagcagtatg tgggaagccc aagaatccgg caaacccagt
 361 gcagcggatc ctgggtggac acctggatgc caaaggcagc tttccctggc aggctaagat
 421 ggtttcccac cataatctca ccacaggtgc cacgctgatc aatgaacaat ggctgctgac
 481 cacggctaaa aatctcttcc tgaaccattc agaaaatgca acagcgaaag acattgcccc
 541 tactttaaca ctctatgtgg ggaaaaagca gcttgtagag attgagaagg ttgttctaca
 601 ccctaactac tcccaggtag atattgggct catcaaactc aaacagaagg tgtctgttaa
 661 tgagagagtg atgcccatct gcctaccttc aaaggattat gcagaagtag ggcgtgtggg
 721 ttatgtttct ggctgggggc gaaatgccaa ttttaaattt actgaccatc tgaagtatgt
 781 catgctgcct gtggctgacc aagaccaatg cataaggcat tatgaaggca gcacagtccc
 841 cgaaaagaag acaccgaaga gccctgtagg ggtgcagccc atactgaatg aacacacctt
 901 ctgtgctggc atgtctaagt accaagaaga cacctgctat ggcgatgcgg gcagtgcctt
 961 tgccgttcac gacctggagg aggacacctg gtatgcgact gggatcttaa gctttgataa
1021 gagctgtgct gtggctgagt atggtgtgta tgtgaaggtg acttccatcc aggactgggt
1081 tcagaagacc atagctgaga actaatgcaa ggctggccgg aagcccttgc ctgaaagcaa
1141 gatttcagcc tggaagaggg caaagtggac gggagtggac aggagtggat gcgataagat
1201 gtggtttgaa gctgatgggt gccagccctg cattgctgag tcaatcaata aagagctttc
1261 ttttgaccca taaaaaaaaa aaaaaaaaaa aaaaaaaaa a
```

(CLC mRNA *Homo sapiens*)

SEQ ID NO: 5

```
   1 catttaaatt ctgcagctca gagattcaca cagaagtctg gacacaattc agaagagcca
  61 cccagaagga gacaacaatg tccctgctac ccgtgccata cacagaggct gcctctttgt
 121 ctactggttc tactgtgaca atcaaagggc gaccacttgc ctgtttcttg aatgaaccat
 181 atctgcaggt ggatttccac actgagatga aggaggaatc agacattgtc ttccatttcc
 241 aagtgtgctt tggtcgtcgt gtggtcatga cagccgtga gtatgggggcc tggaagcagc
 301 aggtggaatc caagaatatg ccctttcagg atggccaaga atttgaactg agcatctcag
 361 tgctgccaga taagtaccag gtaatggtca atggccaatc ctcttacacc tttgaccata
 421 gaatcaagcc tgaggctgtg aagatggtgc aagtgtggag agatatctcc ctgaccaaat
 481 ttaatgtcag ctatttaaag agataaccag acttcatgtt gccaaggaat ccctgtctct
 541 acgtgaactt gggattccaa agccagctaa cagcatgatc tttctcact tcaatccta
 601 ctcctgctca ttaaaactta atcaaacttc acaaaaaaaa aaaaaaaa
```

-continued (CD177 mRNA Homo sapiens)
SEQ ID NO: 6

```
   1 aaaggacttg tttcctgctg aaaaagcaga aagagattac cagccacaga cgggtcatga
  61 gcgcggtatt actgctggcc ctcctggggt tcatcctccc actgccagga gtgcaggcgc
 121 tgctctgcca gtttgggaca gttcagcatg tgtggaaggt gtccgacctg ccccggcaat
 181 ggaccccctaa gaacaccagc tgcgacagcg gcttggggtg ccaggacacg ttgatgctca
 241 ttgagagcgg accccaagtg agcctggtgc tctccaaggg ctgcacggag gccaaggacc
 301 aggagccccg cgtcactgag caccggatgg gccccggcct ctccctgatc tcctacacct
 361 tcgtgtgccg ccaggaggac ttctgcaaca acctcgttaa ctccctcccg ctttgggccc
 421 cacagccccc agcagaccca ggatccttga ggtgcccagt ctgcttgtct atggaaggct
 481 gtctggaggg gacaacagaa gagatctgcc ccaaggggac cacacactgt tatgatggcc
 541 tcctcaggct caggggagga ggcatcttct ccaatctgag agtccaggga tgcatgcccc
 601 agccagtttg caacctgctc aatgggacac aggaaattgg gcccgtgggt atgactgaga
 661 actgcgatat gaaagatttt ctgacctgtc atcggggac caccattatg acacacggaa
 721 acttggctca agaacccact gattggacca catcgaatac cgagatgtgc gaggtggggc
 781 aggtgtgtca ggagacgctg ctgctcctag atgtaggact cacatcaacc ctggtgggga
 841 caaaaggctg cagcactgtt ggggctcaaa attcccagaa gaccaccatc cactcagccc
 901 ctcctggggt gcttgtggcc tcctataccc acttctgctc ctcggacctg tgcaatagtg
 961 ccagcagcag cagcgttctg ctgaactccc tccctcctca agctgcccct gtcccaggag
1021 accggcagtg tcctacctgt gtgcagcccc ttggaacctg ttcaagtggc tccccccgaa
1081 tgacctgccc caggggcgcc actcattgtt atgatgggta cattcatctc tcaggaggtg
1141 ggctgtccac caaaatgagc attcagggct gcgtggccca accttccagc ttcttgttga
1201 accacaccag acaaatcggg atcttctctg cgcgtgagaa gcgtgatgtg cagcctcctg
1261 cctctcagca tgagggaggt ggggctgagg gcctggagtc tctcacttgg ggggtggggc
1321 tggcactggc cccagcgctg tggtggggag tggtttgccc ttcctgctaa ctctattacc
1381 cccacgattc ttcaccgctg ctgaccaccc acactcaacc tccctctgac ctcataaacct
1441 aatggccttg gacaccagat tctttcccat tctgtccatg aatcatcttc cccacacaca
1501 atcattcata tctactcacc taacagcaac actggggaga gcctggagca tccggacttg
1561 ccctatggga gaggggacgc tggaggagtg gctgcatgta tctgataata cagaccctgt
1621 cctttctccc agtgctggga tttctccatg tgagggggca gcaggacacc cagggatcta
1681 gcgtggggga ggagaggagc ctaatgagaa aatgaccatc taaagcctgc ccttcattgg
1741 tctggttcac gtctccaaac cagcttggat ggtagcagag acttcagggt gctccagcca
1801 aacgtatttg ggcatcacca tgacctggga gggaagatg cactgagacg tatgaggctt
1861 ccagcctagc agccagggcc ctagcacaaa caggaggctc gccccatctg agcaactgca
1921 ggagaggtta gtacagtcat gcattgctta acgacaggga cgtgtcgtta gaaatgtgtc
1981 gttaggtgat tttatgacca taggaacatt gtagcgtgca cttacaccaa cccagatggt
2041 acagcccaat acacacccag gatggacgct agagtcgact gctcctaggc tacaagcctg
2101 cagtgcatgt tatggtgtga atactgcagg caatcttaac accacggcaa gtatttgtgc
2161 atctacacac atctaaacat agaaaaggta cagcataaat acactattgt catctcagca
2221 gaaaaaaaaa aaaaaaaa
```

(BATF2 mRNA Homo sapiens, transcript variant 1)

SEQ ID NO: 7

```
   1 gaaactgaaa cttggccctc tggggcgga gtggccactg gggatttaaa gagctgccac
  61 ttccttaggc ctccagaggg cactgggaag tcacagctgc tgagggacca ctctgctccc
 121 ccgcctaagc catgcacctc tgtgggggca atgggctgct gacccagaca gaccccaagg
 181 agcaacaaag gcagctgaag aagcagaaga accgggcagc cgcccagcga agccggcaga
 241 agcacacaga caaggcagac gccctgcacc agcagcacga gtctctggaa aaagacaacc
 301 tcgccctgcg gaaggagatc cagtccctgc aggccgagct ggcgtggtgg agccggaccc
 361 tgcacgtgca tgagcgcctg tgccccatgg attgtgcctc ctgctcagct ccagggctcc
 421 tgggctgctg ggaccaggct gaggggctcc tgggccctgg cccacaggga caacatggct
 481 gccgggagca gctggagctg ttccagaccc cgggttcctg ttacccagct cagccgctct
 541 ctccaggtcc acagcctcat gattctccca gcctcctcca gtgcccctg ccctcactgt
 601 cccttggccc cgctgtggtt gctgaacctc ctgtccagct gtcccccagc cctctcctgt
 661 ttgcctcgca cactggttcc agcctgcagg ggtcttcctc taagctcagt gccctccagc
 721 ccagcctcac ggcccaaact gcccctccac agcccctcga gctggagcat cccaccagag
 781 ggaagctggg gtcctctccc gacaacccct tcctctgccct ggggcttgca cgtctgcaga
 841 gcagggagca caaacctgct ctctcagcag ccacttggca agggctggtt gtggatccca
 901 gccctcaccc tctcctggcc ttcctctgc tctcctctgc tcaagtccac ttctaacctg
 961 gtcttcggag ctgggttggc cccttctttg ggctcaggaa gcagccttag cacacgggcc
1021 tctcctccct cactactggg tgctgccctg cgtggctgac cagctggccc aggatttcac
1081 agtcgaaaag gaagccacca ctgatgcctc ccactgtgac aggccctgtc accaccaata
1141 tcttatttca acctcacagt tgacctgaga aatcgagatt atcactccac tttttcagac
1201 aaggaaactg aggctcaggg aagccaagtg acaagtccaa ggtcacgaag actttcttgg
1261 agcccgaaac accaccctct gctcctcctt ctcctgtcct ggcccaggca tcctaggggc
1321 tgaaatcctg gaaaccgtgg gctggtgtga aaggttttgc atgctcagag cagagaaggg
1381 ctctccccac tgcttcgtga ttccaggggcc agagccatgc agtcccagaa accccaacct
1441 agctggggca ggtccagagt ccaagccctg gtgggtagag gccaagcaga agccctgaag
1501 tggactcttg cttcccctag tagtgttttc agtgccaaga agctgaaact gtgagctgga
1561 gttggggaga ggtctggaag aggaccatct gggatttcta cagcctgggt acccatagcc
1621 acaccaaggc ttctgggaga ttctgcaggg tcagctttcc aggctgttcc caaatagctc
1681 cctgcctccc cactgccccct aaagccacag cagaagagcc attcatctca taaacaaaaa
1741 ggaagaggaa agaatgagga aggaccctgt gcaaggttat ttgcaggcag ggatgggctt
1801 gtacctgaca gcacccaccc ctgtgtggcc cccaggccct catcaccctc agacccctcc
1861 taagcagttc cctcattgct ctttggacta ggctgacagc aggaagagca gggcccatga
1921 ccgggtggaa gttcagtttt ggtgtctgct tcaagagggg gttttacact ctgattccag
1981 gacaagcact ctgaggcggg tggggagag aaaccctggc tcttcaccca ggtttcacac
2041 acatgtaaat gaaacactat gttagtatct aacacactcc tggatacaga acacaagtct
2101 tggcacatat gtgatggaaa taaagtgttt tgcaatcttt aa
```

(BATF2 mRNA Homo sapiens, transcript variant 2)

SEQ ID NO: 8

```
   1 agcaagaaag aaggcgagag agaggagacc ggaggtctga gctgcagcca ctacacaggc
  61 ctggaattct accacaggga atttggtggg tgcctctaaa gggctttaac ctgcaattaa
```

```
121 tgacatggtt gctgaatggc tcctgtgggc aagagaatag gtggtttggg ggacacacgg
181 gttggaggcc cgtgcatatc ccagcagcac gagtctctgg aaaaagacaa cctcgccctg
241 cggaaggaga tccagtccct gcaggccgag ctggcgtggt ggagccggac cctgcacgtg
301 catgagcgcc tgtgccccat ggattgtgcc tcctgctcag ctccagggct cctgggctgc
361 tgggaccagg ctgaggggct cctgggccct ggcccacagg gacaacatgg ctgccgggag
421 cagctggagc tgttccagac cccggggttcc tgttacccag ctcagccgct ctctccaggt
481 ccacagcctc atgattctcc cagcctcctc cagtgccccc tgccctcact gtcccttggc
541 cccgctgtgg ttgctgaacc tcctgtccag ctgtccccca gccctctcct gtttgcctcg
601 cacactggtt ccagcctgca ggggtcttcc tctaagctca gtgccctcca gcccagcctc
661 acggcccaaa ctgcccctcc acagcccctc gagctggagc atcccaccag agggaagctg
721 gggtcctctc ccgacaaccc ttcctctgcc ctggggcttg cacgtctgca gagcagggag
781 cacaaacctg ctctctcagc agccacttgg caagggctgg ttgtggatcc cagccctcac
841 cctctcctgg cctttcctct gctctcctct gctcaagtcc acttctaacc tggtcttcgg
901 agctgggttg gccccttctt tgggctcagg aagcagcctt agcacacggg cctctcctcc
961 ctcactactg ggtgctgccc tgcgtggctg accagctggc ccaggatttc acagtcgaaa
1021 aggaagccac cactgatgcc tcccactgtg acaggccctg tcaccaccaa tatcttattt
1081 caacctcaca gttgacctga gaaatcgaga ttatcactcc acttttttcag acaaggaaac
1141 tgaggctcag ggaagccaag tgacaagtcc aaggtcacga agactttctt ggagcccgaa
1201 acaccaccct ctgctcctcc ttctcctgtc ctggcccagg catcctaggg gctgaaatcc
1261 tggaaaccgt gggctggtgt gagaaggttt gcatgctcag agcagagaag gctctcccc
1321 actgcttcgt gattccaggg ccagagccat gcagtcccag aaacccccaac ctagctgggg
1381 caggtccaga gtccaagccc tggtgggtag aggccaagca gaagccctga gtggactct
1441 tgcttcccct agtagtgttt tcagtgccaa gaagctgaaa ctgtgagctg agttggggga
1501 gaggtctgga agaggaccat ctgggatttc tacagcctgg gtacccatag ccacaccaag
1561 gcttctggga gattctgcag ggtcagcttt ccaggctgtt cccaaatagc tccctgcctc
1621 cccactgccc ctaaagccac agcagaagag ccattcatct cataaacaaa aaggaagagg
1681 aaagaatgag gaaggaccct gtgcaaggtt atttgcaggc agggatgggc ttgtacctga
1741 cagcacccac ccctgtgtgg cccccaggcc ctcatcaccc tcagacccct cctaagcagt
1801 tccctcattg ctcttttggac taggctgaca gcaggaagag cagggcccat gacccgggtgg
1861 aagttcagtt ttggtgtctg cttcaagagg gggttttaca ctctgattcc aggacaagca
1921 ctctgaggcg ggtgggggag agaaaccctg gctcttcacc caggtttcac acacatgtaa
1981 atgaaacact atgttagtat ctaacacact cctggataca gaacacaagt cttggcacat
2041 atgtgatgga aataaagtgt tttgcaatct ttaa
```
(BATF2 mRNA Homo sapiens, transcript variant 3)
SEQ ID NO: 9
```
  1 agcaagaaag aaggcgagag agaggagacc ggaggtctga gctgcagcca ctacacaggc
 61 ctggaattct accacaggga atttgcagca cgagtctctg gaaaaagaca acctcgccct
121 gcggaaggag atccagtccc tgcaggccga gctggcgtgg tggagccgga ccctgcacgt
181 gcatgagcgc ctgtgcccca tggattgtgc ctcctgctca gctccagggc tcctgggctg
241 ctgggaccag gctgaggggc tcctgggccc tggcccacag ggacaacatg gctgccggga
301 gcagctggag ctgttccaga ccccggggttc ctgttaccca gctcagccgc tctctccagg
361 tccacagcct catgattctc ccagcctcct ccagtgcccc ctgccctcac tgtcccttgg
```

```
-continued 421 ccccgctgtg gttgctgaac ctcctgtcca gctgtccccc agccctctcc tgtttgcctc 481 gcacactggt tccagcctgc aggggtcttc ctctaagctc agtgccctcc agcccagcct 541 cacggcccaa actgccctc cacagcccct cgagctggag catcccacca gagggaagct 601 ggggtcctct cccgacaacc cttcctctgc cctggggctt gcacgtctgc agagcaggga 661 gcacaaacct gctctctcag cagccacttg gcaagggctg gttgtggatc ccagccctca 721 ccctctcctg gcctttcctc tgctctcctc tgctcaagtc cacttctaac ctggtcttcg 781 gagctgggtt ggcccttct ttgggctcag gaagcagcct tagcacacgg gcctctcctc 841 cctcactact gggtgctgcc ctgcgtggct gaccagctgg cccaggattt cacagtcgaa 901 aaggaagcca ccactgatgc ctcccactgt gacaggccct gtcaccacca atatcttatt 961 tcaacctcac agttgacctg agaaatcgag attatcactc cacttttca gacaaggaaa 1021 ctgaggctca gggaagccaa gtgacaagtc caaggtcacg aagactttct tggagcccga 1081 aacaccaccc tctgctcctc cttctcctgt cctggcccag gcatcctagg ggctgaaatc 1141 ctggaaaccg tgggctggtg tgagaaggtt tgcatgctca gagcagagaa gggctctccc 1201 cactgcttcg tgattccagg gccagagcca tgcagtccca gaaacccaa cctagctggg 1261 gcaggtccag agtccaagcc ctggtgggta gaggccaagc agaagccctg aagtggactc 1321 ttgcttcccc tagtagtgtt ttcagtgcca agaagctgaa actgtgagct ggagttgggg 1381 agaggtctgg aagaggacca tctgggattt ctacagcctg ggtacccata gccacaccaa 1441 ggcttctggg agattctgca gggtcagctt tccaggctgt tcccaaatag ctccctgcct 1501 ccccactgcc cctaaagcca cagcagaaga gccattcatc tcataaacaa aaaggaagag 1561 gaaagaatga ggaaggaccc tgtgcaaggt tatttgcagg cagggatggg cttgtacctg 1621 acagcaccca cccctgtgtg gcccccaggc cctcatcacc ctcagacccc tcctaagcag 1681 ttccctcatt gctctttgga ctaggctgac agcaggaaga gcagggccca tgaccgggtg 1741 gaagttcagt tttggtgtct gcttcaagag ggggttttac actctgattc caggacaagc 1801 actctgaggc gggtggggga gagaaaccct ggctcttcac ccaggtttca cacacatgta 1861 aatgaaacac tatgttagta tctaacacac tcctggatac agaacacaag tcttggcaca 1921 tatgtgatgg aaataaagtg ttttgcaatc tttaa
```

SELECTED REFERENCES

Anderson, S. T. et al. Diagnosis of childhood tuberculosis and host RNA expression in Africa. *N. Engl. J. Med.* 370, 1712-1723 (2014).

Berry M P R, Graham C M, McNab F W, Xu Z, Bloch S A A, Oni T, Wilkinson K A, Banchereau R, Skinner J, Wilkinson R J, Quinn C, Blankenship D, Dhawan R, Cush J J, Mejias A, Ramilo O, Kon O M, Pascual V, Banchereau J, Chaussabel D, O'Garra A. An interferon-inducible neutrophil-driven blood transcriptional signature in human tuberculosis. *Nature* 2010; 466:973-977.

Blankley, S. et al. A 380-gene meta-signature of active tuberculosis compared with healthy controls. *Eur. Respir. J.* (2016). doi:10.1183/13993003.02121-2015

Bloom C I, Graham C M, Berry M P R, Rozakeas F, Redford P S, Wang Y, Xu Z, Wilkinson K A, Wilkinson R J, Kendrick Y, Devouassoux G, Ferry T, Miyara M, Bouvry D, Valeyre D, Dominique V, Gorochov G, Blankenship D, Saadatian M, Vanhems P, Beynon H, Vancheeswaran R, Wickremasinghe M, Chaussabel D, Banchereau J, Pascual V, Ho L-P, Lipman M, O'Garra A. Transcriptional blood signatures distinguish pulmonary tuberculosis, pulmonary sarcoidosis, pneumonias and lung cancers. *PloS One* 2013; 8:e70630.

Bloom C I, Graham C M, Berry M P R, Wilkinson K A, Oni T, Rozakeas F, Xu Z, Rossello-Urgell J, Chaussabel D, Banchereau J, Pascual V, Lipman M, Wilkinson R J, O'Garra A. Detectable changes in the blood transcriptome are present after two weeks of antituberculosis therapy. *PloS One* 2012; 7.

Boehme C C, Saacks S, O'Brien R J. The changing landscape of diagnostic services for tuberculosis. *Semin Respir Crit Care Med* 2013; 34:17-31.

Breuer K, Foroushani A K, Laird M R, Chen C, Sribnaia A, Lo R, Winsor G L, Hancock R E W, Brinkman F S L, Lynn D J. InnateDB: systems biology of innate immunity and beyond—recent updates and continuing curation. *Nucleic Acids Res* 2013; 41:D1228-1233.

Chain B. agilp: Agilent expression array processing package. at <http://www.bioconductor.org/packages/release/bioc/html/agilp.html>.

Chain B, Bowen H, Hammond J, Posch W, Rasaiyaah J, Tsang J, Noursadeghi M. Error, reproducibility and sensitivity: a pipeline for data processing of Agilent oligonucleotide expression arrays. *BMC Bioinformatics* 2010; 11.

Chua J C, Douglass J A, Gillman A, O'Hehir R E, Meeusen E N. Galectin-10, a potential biomarker of eosinophilic airway inflammation. *PloS One* 2012; 7:e42549.

Cliff J M, Lee J-S, Constantinou N, Cho J-E, Clark T G, Ronacher K, King E C, Lukey P T, Duncan K, Van Helden P D, Walzl G, Dockrell H M. Distinct phases of blood gene expression pattern through tuberculosis treatment reflect modulation of the humoral immune response. *J Infect Dis* 2013; 207:18-29.

Cristianini N, Shawe-Taylor J. *An Introduction to Support Vector Machines and Other Kernel-based Learning Methods*. Cambridge University Press; 2000.

Denkinger C M, Schumacher S G, Boehme C C, Dendukuri N, Pai M, Steingart K R. Xpert MTB/RIF assay for the diagnosis of extrapulmonary tuberculosis: a systematic review and meta-analysis. *Eur Respir J* 2014; 44:435-446.

Dinnes J, Deeks J, Kunst H, Gibson A, Cummins E, Waugh N, Drobniewski F, Lalvani A. A systematic review of rapid diagnostic tests for the detection of tuberculosis infection. *Health Technol Assess Winch Engl* 2007; 11:1-196.

Göhring K, Wolff J, Doppl W, Schmidt K L, Fenchel K, Pralle H, Sibelius U, Bux J. Neutrophil CD177 (NB1 gp, HNA-2a) expression is increased in severe bacterial infections and polycythaemia vera. *Br J Haematol* 2004; 126:252-254.

Kaforou M, Wright V J, Oni T, French N, Anderson S T, Bangani N, Banwell C M, Brent A J, Crampin A C, Dockrell H M, Eley B, Heyderman R S, Hibberd M L, Kern F, Langford P R, Ling L, Mendelson M, Ottenhoff T H, Zgambo F, Wilkinson R J, Coin L J, Levin M. Detection of tuberculosis in HIV-infected and -uninfected African adults using whole blood RNA expression signatures: a case-control study. *PLoS Med* 2013; 10:e1001538.

Maertzdorf J, Weiner J, Kaufmann S H E. Enabling biomarkers for tuberculosis control. *Int J Tuberc Lung Dis Off J Int Union Tuberc Lung Dis* 2012a; 16:1140-1148.

Maertzdorf J, Weiner J, Mollenkopf H-J, TBornotTB Network, Bauer T, Prasse A, Müller-Quernheim J, Kaufmann S H E. Common patterns and disease-related signatures in tuberculosis and sarcoidosis. *Proc Natl Acad Sci USA* 2012b; 109:7853-7858.

Maertzdorf J, McEwen G, Weiner J, Tian S, Lader E, Schriek U, Mayanja-Kizza H, Ota M, Kenneth J, Kaufmann S H. Concise gene signature for point-of-care classification of tuberculosis. *EMBO Mol Med* 2015; doi:10.15252/emmm.201505790.

Martineau A R, Timms P M, Bothamley G H, Hanifa Y, Islam K, Claxton A P, Packe G E, Moore-Gillon J C, Darmalingam M, Davidson R N, Milburn H J, Baker L V, Barker R D, Woodward N J, Venton T R, Barnes K E, Mullett C J, Coussens A K, Rutterford C M, Mein C A, Davies G R, Wilkinson R J, Nikolayevskyy V, Drobniewski F A, Eldridge S M, Griffiths C J. High-dose vitamin D(3) during intensive-phase antimicrobial treatment of pulmonary tuberculosis: a double-blind randomised controlled trial. *Lancet* 2011; 377:242-250.

Matsuo K, Lin A, Procter J L, Clement L, Stroncek D. Variations in the expression of granulocyte antigen NB1. *Transfusion (Paris)* 2000; 40:654-662.

McHugh L, Seldon T A, Brandon R A, Kirk J T, Rapisarda A, Sutherland A J, Presneill J J, Venter D J, Lipman J, Thomas M R, Klein Klouwenberg P M C, van Vught L, Scicluna B, Bonten M, Cremer O L, Schultz M J, van der Poll T, Yager T D, Brandon R B. A Molecular Host Response Assay to Discriminate Between Sepsis and Infection-Negative Systemic Inflammation in Critically Ill Patients: Discovery and Validation in Independent Cohorts. *PLoS Med* 2015; 12:e1001916.

Murphy T L, Tussiwand R, Murphy K M. Specificity through cooperation: BATF-IRF interactions control immune-regulatory networks. *Nat Rev Immunol* 2013; 13:499-509.

Norbis L, Alagna R, Tortoli E, Codecasa L R, Migliori G B, Cirillo D M. Challenges and perspectives in the diagnosis of extrapulmonary tuberculosis. *Expert Rev Anti Infect Ther* 2014; 12:633-647.

Noursadeghi, M. et al. Genome-wide innate immune responses in HIV-1-infected macrophages are preserved despite attenuation of the NF-kappa B activation pathway. *J. Immunol. Baltim. Md.* 1950 182, 319-328 (2009).

Platt J, others. Probabilistic outputs for support vector machines and comparisons to regularized likelihood methods. *Adv Large Margin Classif* 1999; 10:61-74.

Roe, J. K. et al. Blood transcriptomic diagnosis of pulmonary and extrapulmonary tuberculosis. *JCI Insight* 1, (2016).

Roy S, Guler R, Parihar S P, Schmeier S, Kaczkowski B, Nishimura H, Shin J W, Negishi Y, Ozturk M, Hurdayal R, Kubosaki A, Kimura Y, de Hoon M J L, Hayashizaki Y, Brombacher F, Suzuki H. Batf2/Irf1 induces inflammatory responses in classically activated macrophages, lipopolysaccharides, and mycobacterial infection. *J Immunol Baltim Md.* 1950 2015; 194:6035-6044.

Stroncek D F, Shankar R A, Noren P A, Herr G P, Clement L T. Analysis of the expression of NB1 antigen using two monoclonal antibodies. *Transfusion (Paris)* 1996; 36:168-174.

Tomlinson, G. S. et al. HIV-1 infection of macrophages dysregulates innate immune responses to *Mycobacterium tuberculosis* by inhibition of interleukin 10. *J. Infect. Dis.* (2013). doi:10.1093/infdis/jit621

Towers G J, Noursadeghi M. Interactions between HIV-1 and the cell-autonomous innate immune system. *Cell Host Microbe* 2014; 16:10-18.

Walter N D, Miller M A, Vasquez J, Weiner M, Chapman A, Engle M, Higgins M, Quinones A M, Roselli V, Canono E, Yoon C, Cattamanchi A, Davis J L, Phang T, Stearman R S, Datta G, Garcia B J, Daley C L, Strong M, Kechris K, Fingerlin T E, Reves R, Geraci M W. Blood transcriptional biomarkers for active T B among U S patients: A case-control study with systematic cross-classifier evaluation. *J Clin Microbiol* 2015; doi:10.1128/JCM.01990-15.

WHO|Global tuberculosis report 2015.

WHO at http://www.who.int/tb/publications/global_report/en/

Zak, D. E. et al. A blood RNA signature for tuberculosis disease risk: a prospective cohort study. *Lancet Lond. Engl.* (2016). doi:10.1016/S0140-6736(15)01316-1

The invention claimed is:

1. A method for processing a blood sample from a human subject who is not already showing symptoms of active tuberculosis to predict onset of symptoms of active tuberculosis in the subject within 12 months and treating the subject before the onset of symptoms of active tuberculosis, the method comprising:

determining a level of a biomarker consisting of basic leucine zipper transcription factor ATF-like 2 (BATF2) by determining the level of a mRNA transcript of BATF2 in the sample comparing the level of BATF2 in the sample to a reference value, and predicting the onset of symptoms of active tuberculosis in the subject when the level of BATF2 in the sample is increased by at least 2-fold as compared to the reference value, wherein the reference value is a reference range or mean of a reference value range derived from:
(i) more than one healthy subject
   (a) with no prior tuberculosis exposure;
   (b) having a latent tuberculosis infection (LTBI);
   (c) who has recovered from tuberculosis; or
   (d) who suffers from no illness whatsoever;
or
(ii) the same subject: and administering a therapeutically effective amount of an anti-tuberculosis agent to the subject predicted to develop symptoms of active tuberculosis, wherein said anti-tuberculosis agent is one or more anti-tuberculosis agent selected from the group consisting of: an antibiotic, a corticosteroid, a chemotherapeutic agent, and a TNF inhibitor.

2. The method according to claim 1, further comprising testing the sample for the presence or absence of *Mycobacterium tuberculosis* using a microbiological technique.

3. The method of claim 1, wherein active tuberculosis is pulmonary tuberculosis or extrapulmonary tuberculosis.

4. The method of claim 1, wherein the subject is HIV-negative or the reference value is derived from a HIV-negative subject.

5. The method of claim 1, wherein the level of the BATF2 biomarker in the sample differs by at least 3-fold, at least 4-fold, at least 5-fold, at least 6-fold, at least 8-fold or at least 10-fold as compared to the reference value.

6. The method of claim 1, wherein the method is carried out up to 3 months before the onset of symptoms of active tuberculosis in the subject.

7. The method of claim 1, wherein:
(a) the antibiotic or chemotherapeutic agent is selected from the group consisting of: isoniazid, rifampicin, pyrazinamide, streptomycin, para-aminosalicylic acid (PAS), moxifloxacin, ciprofloxacin, ethambutol, and combinations thereof;
(b) the corticosteroid is selected from the group consisting of: prednisolone, dexamethasone and combinations thereof; and/or
(c) the TNF inhibitor is selected from the group consisting of infliximab, adalimumbab, certolizumab, etanercept, and combinations thereof.

* * * * *